(12) United States Patent
van Duzer et al.

(10) Patent No.: US 10,464,906 B2
(45) Date of Patent: Nov. 5, 2019

(54) CRYSTALLINE FORMS OF A HISTONE DEACETYLASE INHIBITOR

(71) Applicant: Acetylon Pharmaceuticals, Inc., Boston, MA (US)

(72) Inventors: John H. van Duzer, Georgetown, MA (US); Farzaneh Seyedi, Mansfield, MA (US); Gui Liu, Lexington, MA (US)

(73) Assignee: ACETYLON PHARMACEUTICALS, INC., Boston, MA (US)

( * ) Notice: Subject to any disclaimer, the term of this patent is extended or adjusted under 35 U.S.C. 154(b) by 0 days.

(21) Appl. No.: 15/176,788

(22) Filed: Jun. 8, 2016

(65) Prior Publication Data

US 2017/0001965 A1 Jan. 5, 2017

Related U.S. Application Data

(60) Provisional application No. 62/172,629, filed on Jun. 8, 2015.

(51) Int. Cl.
*C07D 239/42* (2006.01)

(52) U.S. Cl.
CPC ........ *C07D 239/42* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 6,777,217 B1 | 8/2004 | Schreiber et al. | |
| 7,244,853 B2 | 7/2007 | Schreiber et al. | |
| 7,250,504 B2 | 7/2007 | Grozinger et al. | |
| 7,994,362 B2 | 8/2011 | Schreiber et al. | |
| 8,148,526 B1 | 4/2012 | Van Duzer et al. | |
| 8,394,810 B2 | 3/2013 | Van Duzer et al. | |
| 8,609,678 B2 * | 12/2013 | Van Duzer | C07C 259/06 514/256 |
| 8,614,223 B2 | 12/2013 | Van Duzer et al. | |
| 8,999,289 B2 | 4/2015 | Anderson et al. | |
| 9,096,549 B2 | 8/2015 | Van Duzer et al. | |
| 9,139,583 B2 | 9/2015 | Van Duzer et al. | |
| 9,145,412 B2 | 9/2015 | Van Duzer et al. | |
| 9,278,963 B2 | 3/2016 | Van Duzer et al. | |
| 9,421,212 B2 | 3/2016 | Van Duzer et al. | |
| 9,403,779 B2 | 8/2016 | Tamang et al. | |

(Continued)

FOREIGN PATENT DOCUMENTS

| WO | 2001/070675 A2 | 9/2001 |
|---|---|---|
| WO | 2002/074298 A1 | 9/2002 |

(Continued)

OTHER PUBLICATIONS

Morissette, High-throughput crystallization: polymorphs, salts, co-crystals, and solvates of pharmaceutical solids, Advanced Drug Delivery Reviews, 2004, 56, pp. 275-300.*

(Continued)

*Primary Examiner* — Melenie L Gordon
*Assistant Examiner* — Andrew P Lee
(74) *Attorney, Agent, or Firm* — Lathrop Gage LLP; Brian C. Trinque; Benjamin A. Vaughan

(57) ABSTRACT

This disclosure provides solid forms of 2-((2-chlorophenyl)(phenyl)amino)-N-(7-(hydroxyamino)-7-oxoheptyl)pyrimidine-5-carboxamide, and methods of manufacturing and using these forms.

4 Claims, 48 Drawing Sheets

(56) References Cited

U.S. PATENT DOCUMENTS

| | | |
|---|---|---|
| 9,409,890 B2 | 8/2016 | Van Duzer et al. |
| 9,464,073 B2 | 10/2016 | Mazitschek et al. |
| 9,562,013 B2 | 2/2017 | Van Duzer et al. |
| 2004/0266769 A1 | 12/2004 | Bressi et al. |
| 2005/0119305 A1 | 6/2005 | Naka et al. |
| 2006/0239909 A1 | 10/2006 | Anderson et al. |
| 2007/0093413 A1 | 4/2007 | Schreiber et al. |
| 2007/0149495 A1 | 6/2007 | Bressi et al. |
| 2009/0023786 A1 | 1/2009 | Miller et al. |
| 2009/0209590 A1 | 8/2009 | Mazitschek et al. |
| 2009/0305384 A1 | 12/2009 | Grozinger et al. |
| 2009/0312363 A1 | 12/2009 | Bradner et al. |
| 2010/0137196 A1 | 6/2010 | Schreiber et al. |
| 2010/0330197 A1 | 12/2010 | Higashiguchi et al. |
| 2011/0218154 A1 | 9/2011 | Schreiber et al. |
| 2013/0225543 A1 | 8/2013 | Jones et al. |
| 2014/0011767 A1 | 1/2014 | Yang et al. |
| 2014/0142117 A1 | 5/2014 | Van Duzer et al. |
| 2014/0357512 A1 | 12/2014 | Yang et al. |
| 2015/0045380 A1 | 2/2015 | Van Duzer et al. |
| 2015/0105358 A1 | 4/2015 | Quayle et al. |
| 2015/0105383 A1 | 4/2015 | Quayle et al. |
| 2015/0105409 A1 | 4/2015 | Quayle et al. |
| 2015/0119413 A1 | 4/2015 | Gradilone et al. |
| 2015/0150871 A1 | 6/2015 | Quayle et al. |
| 2015/0176076 A1 | 6/2015 | Yang et al. |
| 2015/0250786 A1 | 9/2015 | Berton et al. |
| 2015/0359794 A1 | 12/2015 | Benz et al. |
| 2016/0030458 A1 | 2/2016 | Jones et al. |
| 2016/0137630 A1 | 5/2016 | Shearstone et al. |
| 2016/0158231 A1 | 6/2016 | Jarpe et al. |
| 2016/0158232 A1 | 6/2016 | Pozzi et al. |
| 2016/0168093 A1 | 6/2016 | Van Duzer et al. |
| 2016/0228434 A1 | 8/2016 | Reilly et al. |
| 2016/0279128 A1 | 9/2016 | Van Duzer et al. |
| 2016/0339022 A1 | 11/2016 | Tamang et al. |
| 2016/0346279 A1 | 12/2016 | Kavelaars et al. |
| 2016/0355486 A1 | 12/2016 | Seyedi et al. |
| 2016/0375021 A1 | 12/2016 | Van Duzer et al. |
| 2017/0020872 A1 | 1/2017 | Tamang et al. |
| 2017/0044144 A1 | 2/2017 | Van Duzer et al. |
| 2017/0096403 A1 | 4/2017 | Van Duzer et al. |

FOREIGN PATENT DOCUMENTS

| | | |
|---|---|---|
| WO | 2003/037869 A1 | 5/2003 |
| WO | 2006/102557 A2 | 9/2006 |
| WO | 2007/022638 A1 | 3/2007 |
| WO | 2007/130429 A2 | 11/2007 |
| WO | 2007/144341 A1 | 12/2007 |
| WO | 2008/003801 A1 | 1/2008 |
| WO | 2008/033746 A2 | 3/2008 |
| WO | 2008/091349 A1 | 7/2008 |
| WO | 2010/011296 A2 | 1/2010 |
| WO | 2010/131922 A2 | 11/2010 |
| WO | 2011/019393 A2 | 2/2011 |
| WO | 2011/084991 A2 | 7/2011 |
| WO | 2011/091213 A2 | 7/2011 |
| WO | 2011/146855 A1 | 11/2011 |
| WO | 2013/013113 A2 | 1/2013 |
| WO | 2015/054197 A1 | 4/2015 |
| WO | 2015/061684 A1 | 4/2015 |

OTHER PUBLICATIONS

Butler et al. (2000) "Suberoylanilide Hydroxamic Acid, an Inhibitor of Histone Deacetylase, Suppresses the Growth of Prostate Cancer Cells in Vitro and in Vivo," Cancer Research. 60:5165-5170.

Costello et al. (Dec. 2012) "Evidence for Changes in RREB-1, ZIP3, and Zinc in the Early Development of Pancreatic Adenocarcinoma," J. Gastrointest. Canc. 43:570-578.

Dokmanovic et al. (2007) "Histone Deacetylase Inhibitors: Overview and Perspectives," Mol. Cancer Res. 5 (10):981-989.

Giannini et al. (Jul. 2012) "Histone Deacetylase Inhibitors in the Treatment of Cancer: Overview and Perspectives," Future Med. Chem. 4(11):1439-1460.

Haggarty et al. (2003) "Domain-selective Small-molecule Inhibitor of Histone Deacetylase 6 (HDAC6)-mediated Tubulin Deacetylation," Proc. Natl. Acad. Sci. USA. 100(8):4389-4394.

Kozikowski et al. (2008) "Use of the Nitrile Oxide Cycloaddition (NOC) Reaction for Molecular Probe Generation: A New Class of Enzyme Selective Histone Deacetylase Inhibitors (HDACIs) Showing Picomolar Activity at HDAC6," Journal of Medicinal Chemistry. 51:4370-4373.

Lane et al. (2009) "Histone Deacetylase Inhibitors in Cancer Therapy," J. Clin. Oncol. 27:5459-5468.

Loudni et al. (2007) "Design, synthesis and biological evaluation of 1, 4-benzodiazepine-2, 5-dione-based HDAC Inhibitors," Bioorganic and Medicinal Chemistry Letters. 17:4819-4823.

Mazitschek et al. (2008) "Development of a Fluorescence Polarization Based Assay for Histone Deacetylase Ligand Discovery," Bioorganic and Medicinal Chemistry Letters. 18(9):2809-2812.

Miller et al. (1998) "Paclitaxel as the Initial Treatment of Multiple Myeloma: An Eastern Cooperative Oncology Group Study (E1A93)," Am. J. Clin. Oncol. 21(6):553-556.

Perez (1998) "Paclitaxel in Breast Cancer," The Oncologist. 3:373-389.

Ropero et al. (2007) "The Role of Histone Deacetylases (HDACs) in Human Cancer," Molecular Oncology. 1:19-25.

Smil et al. (2009) "Novel HDAC6 Isoform Selective Chiral Small Molecule Histone Deacetylase Inhibitors," Bioorganic and Medicinal Chemistry Letters. 19:688-692.

Sporn et al. (2000) "Chemoprevention of Cancer," Carcinogenesis. 21(3):525-530.

Thoppil et al. (Sep. 2011) "Terpenoids as Potential Chemopreventive and Therapeutic Agents in Liver Cancer," World J. Hepatol. 3(9):228-249.

International Search Report with Written Opinion corresponding to International Patent Application No. PCT/US2011/021982, dated Oct. 10, 2011.

International Search Report with Written Opinion corresponding to International Patent Application No. PCT/US2016/036422, dated Jul. 28, 2016.

Search Opinion corresponding to European Patent Application No. 11735212, dated Jun. 26, 2014.

Written Opinion corresponding to Singapore Patent Application No. Application No. 201205393-0, dated Nov. 15, 2013.

\* cited by examiner

CRYSTALLINE FORMS OF A HISTONE DEACETYLASE INHIBITOR

RELATED APPLICATION

This application claims priority to U.S. Provisional Application Ser. No. 62/172,629 filed Jun. 8, 2015, the content of which is incorporated herein in its entirety.

TECHNICAL FIELD

This disclosure relates to crystalline forms of 2-((2-chlorophenyl)(phenyl)amino)-N-(7-(hydroxyamino)-7-oxoheptyl)pyrimidine-5-carboxamide and related compositions and methods.

BACKGROUND

The crystal state of a compound can be important when the compound is used for pharmaceutical purposes. Compared with an amorphous solid, the solid physical properties of a crystalline compound can change, which can affect its suitability for pharmaceutical use. For example, a particular crystalline compound can overcome the disadvantage of other solid forms of the compound that, for example, readily absorb moisture (high hygroscopicity).

SUMMARY

Crystalline forms of 2-((2-chlorophenyl)(phenyl)amino)-N-(7-(hydroxyamino)-7-oxoheptyl)pyrimidine-5-carboxamide or hydrates or solvates thereof and compositions comprising these solid forms are provided herein, in addition to various methods of preparing these compositions. Crystalline forms of 2-((2-chlorophenyl)(phenyl)amino)-N-(7-(hydroxyamino)-7-oxoheptyl)pyrimidine-5-carboxamide have shown advantageous characteristics that are beneficial to the preparation of various drug formulations. Several crystalline forms have been identified and characterized herein (e.g., Form I, Form II, Form III, Form IV, Form V, Form VII, and Form IX). These crystalline forms can have good stability in the process of preparation, packing, transportation, and storage.

Thus, in an aspect, provided herein is crystalline 2-((2-chlorophenyl)(phenyl)amino)-N-(7-(hydroxyamino)-7-oxoheptyl)pyrimidine-5-carboxamide.

In another aspect, provided herein is a pharmaceutical composition comprising a crystalline form of 2-((2-chlorophenyl)(phenyl)amino)-N-(7-(hydroxyamino)-7-oxoheptyl)pyrimidine-5-carboxamide, and a pharmaceutically acceptable carrier.

In another aspect, provided herein is a method of treating cancer comprising administering to a subject in need thereof a therapeutically effective amount of a crystalline form of 2-((2-chlorophenyl)(phenyl)amino)-N-(7-(hydroxyamino)-7-oxoheptyl)pyrimidine-5-carboxamide.

In yet another aspect, provided herein is method of treating cancer comprising administering to a subject in need thereof a therapeutically effective amount of a pharmaceutical composition comprising a crystalline form of 2-((2-chlorophenyl)(phenyl)amino)-N-(7-(hydroxyamino)-7-oxoheptyl)pyrimidine-5-carboxamide.

In another aspect, provided herein is a composition comprising Form I of 2-((2-chlorophenyl)(phenyl)amino)-N-(7-(hydroxyamino)-7-oxoheptyl)pyrimidine-5-carboxamide formed by a process comprising:

(a) suspending a composition comprising 2-((2-chlorophenyl)(phenyl)amino)-N-(7-(hydroxyamino)-7-oxoheptyl)pyrimidine-5-carboxamide in a solvent to form a slurry;
(b) heating the slurry until the solids are dissolved;
(c) seeding the solution formed in step (b) with of crystals of Form I of 2-((2-chlorophenyl)(phenyl)amino)-N-(7-(hydroxyamino)-7-oxoheptyl)pyrimidine-5-carboxamide;
(d) cooling the solution until a precipitate forms; and
(e) filtering the precipitate,
wherein Form I is characterized by an X-ray powder diffraction pattern having peaks expressed in degrees-2-theta at angles 8.3±0.2°, 10.6±0.2°, 16.6±0.2°, 21.3±0.2°, and 25.0±0.2°.

In another aspect, provided herein is a pharmaceutical composition comprising 2-((2-chlorophenyl)(phenyl)amino)-N-(7-(hydroxyamino)-7-oxoheptyl)pyrimidine-5-carboxamide of Form I and a pharmaceutically acceptable carrier, wherein Form I is characterized by an X-ray powder diffraction pattern having peaks expressed in degrees-2-theta at angles 8.3±0.2°, 10.6±0.2°, 16.6±0.2°, 21.3±0.2°, and 25.0±0.2°.

DETAILED DESCRIPTION

Figure 1:
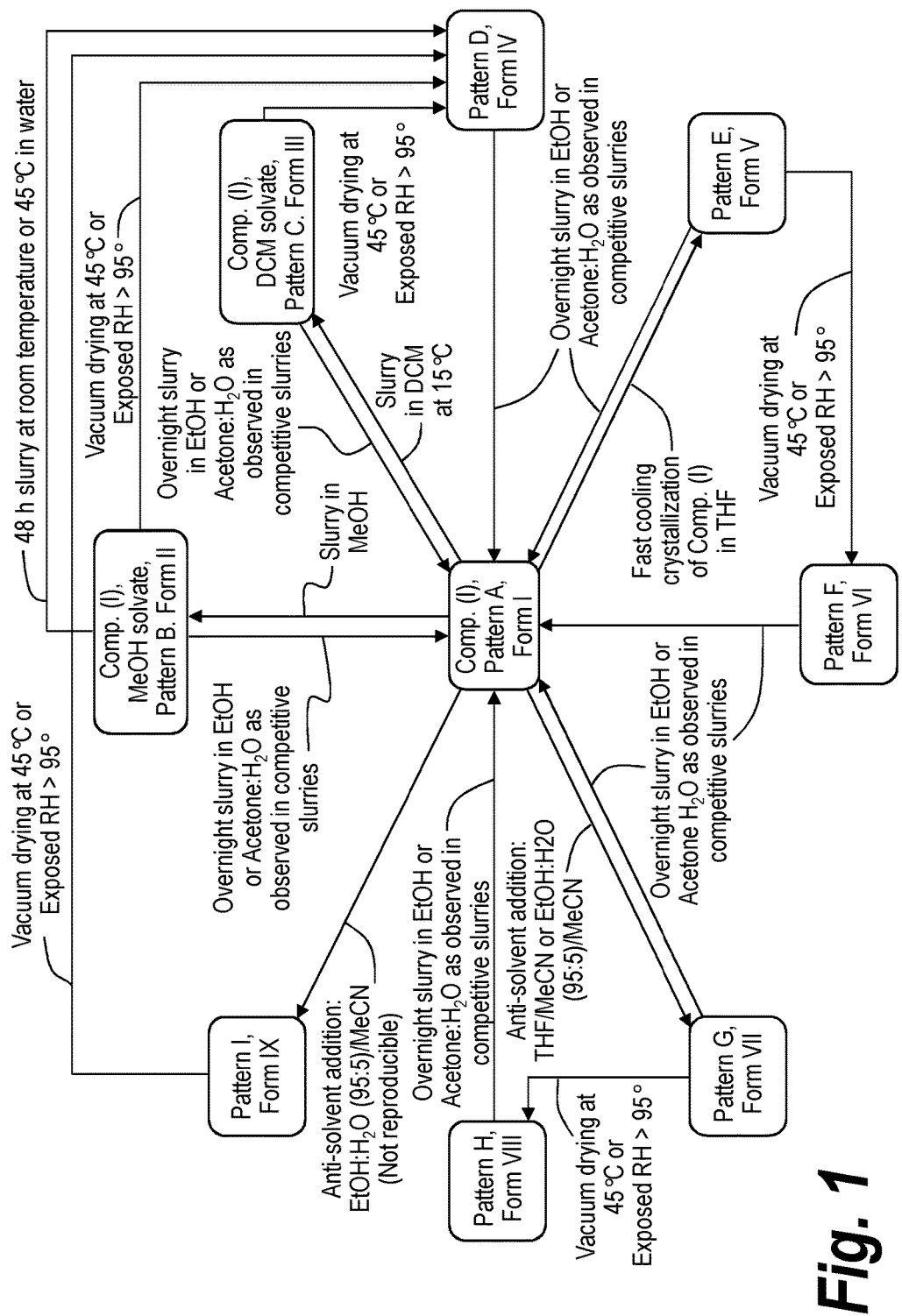
FIG. 1 is a flowchart showing the interconversion of polymorphs of Compound (I).

Provided herein are crystalline forms of 2-((2-chlorophenyl)(phenyl)amino)-N-(7-(hydroxyamino)-7-oxoheptyl)pyrimidine-5-carboxamide (CAS No. 1316215-12-9), shown as Compound (I) (and referred to herein as "Compound (I)"):

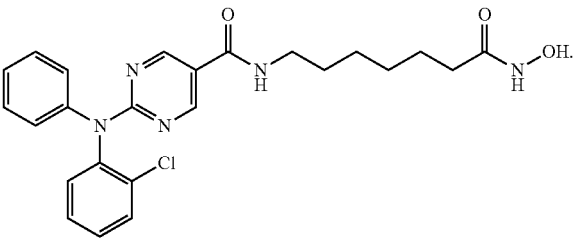

Compound (I)

Compound (I) is disclosed in International Patent Application No. PCT/US2011/021982 and U.S. Pat. No. 8,609,678, the entire contents of which are incorporated herein by reference.

Accordingly, provided herein are crystalline forms of 2-((2-chlorophenyl)(phenyl)amino)-N-(7-(hydroxyamino)-7-oxoheptyl)pyrimidine-5-carboxamide. In particular, provided herein are the following crystalline forms of Compound (I): Form I, Form II, Form III, Form IV, Form V, Form VI, Form VII, Form VIII, and Form IX. Each of these forms have been characterized by XRPD analysis. In an embodiment, the crystalline form of 2-((2-chlorophenyl)(phenyl)amino)-N-(7-(hydroxyamino)-7-oxoheptyl)pyrimidine-5-carboxamide can be a hydrate or solvate (e.g., dichloromethane or methanol).

Polymorphism

The ability of a substance to exist in more than one crystal form is defined as polymorphism; the different crystal forms of a particular substance are referred to as "polymorphs." In general, polymorphism is affected by the ability of a molecule of a substance to change its conformation or to form different intermolecular or intra-molecular interactions, particularly hydrogen bonds, which is reflected in different atom arrangements in the crystal lattices of different polymorphs. In contrast, the overall external form of a substance is known as "morphology," which refers to the external shape of the crystal and the planes present, without reference to the internal structure. Crystals can display different morphology based on different conditions, such as, for example, growth rate, stirring, and the presence of impurities.

The different polymorphs of a substance can possess different energies of the crystal lattice and, thus, in solid state they can show different physical properties such as form, density, melting point, color, stability, solubility, dissolution rate, etc., which can, in turn, affect the stability, dissolution rate and/or bioavailability of a given polymorph and its suitability for use as a pharmaceutical and in pharmaceutical compositions.

Access to different polymorphs of 2-((2-chlorophenyl)(phenyl)amino)-N-(7-(hydroxyamino)-7-oxoheptyl)pyrimidine-5-carboxamide is desirable for several reasons. One such reason is that different polymorphs of a compound can incorporate different impurities or chemical residues upon crystallization. Certain polymorphs incorporate very little, or no, chemical residues. Accordingly, the formation of certain polymorph forms of a compound may result in purification of the compound.

Certain crystalline forms of Compound (I) provided herein exhibit favorable properties. For example, Form I of crystalline Compound (I) exhibits low hygroscopicity. Low hygroscopicity is particularly desirable for pharmaceutical compounds. This is because highly hygroscopic compounds may be chemically unstable or unsuitable for formulating as a drug product due to changes of the drug form's physical characteristics (e.g., bulk density, dissolution rate, etc.) when stored under conditions of high humidity. Hygroscopicity can also affect large-scale manufacturing and handling of a compound. For example, it can be difficult to accurately determine the true weight of a hygroscopic active agent when preparing, for example, pharmaceutical compositions or formulations.

Figure 6:
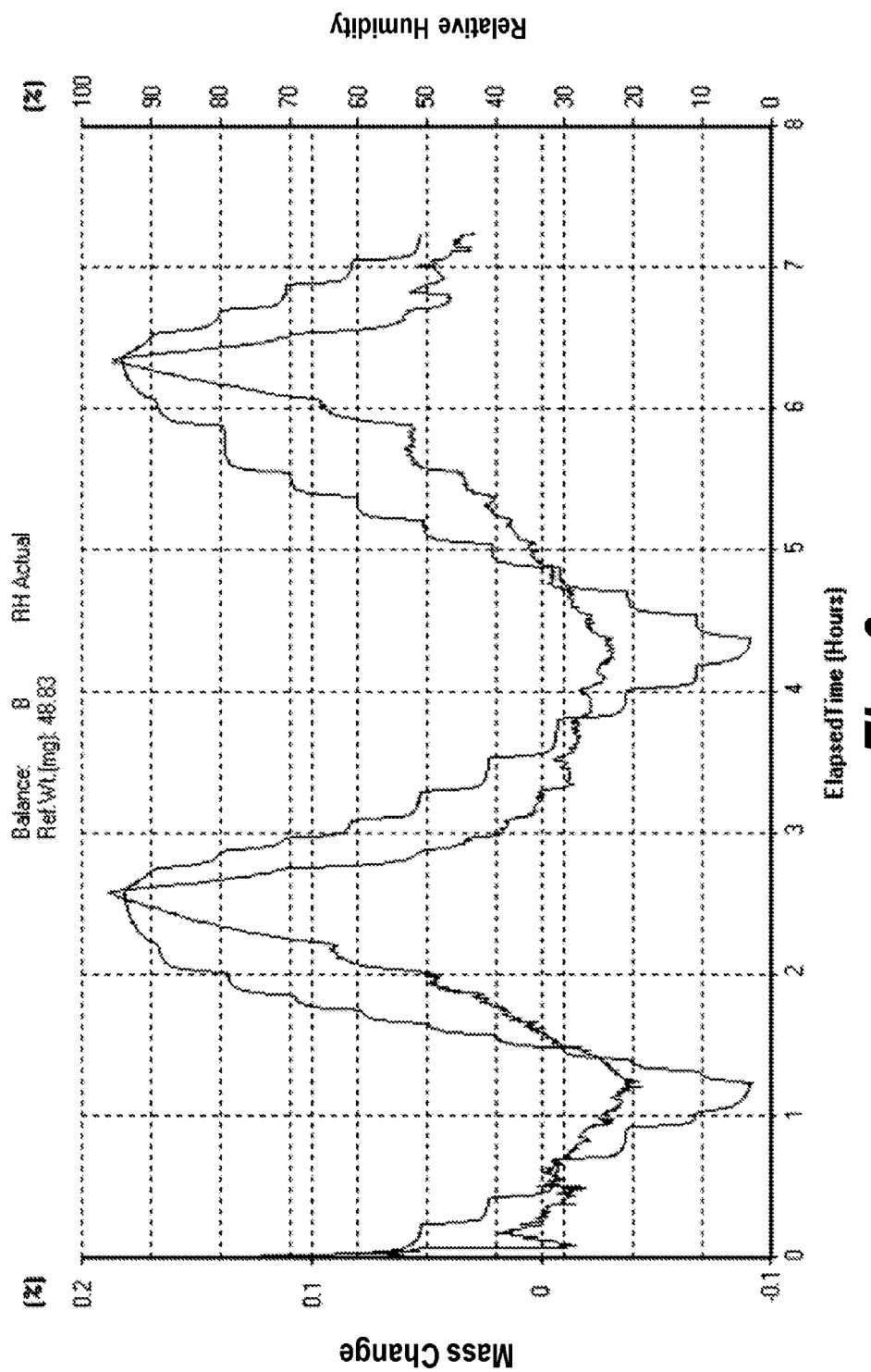
FIG. 6 shows the DVS-Kinetic graph of Form I.

FIG. 6 depicts the dynamic vapor sorption (DVS) graph of Form I of Compound (I). This DVS experiment revealed less than 0.2% of moisture uptake by Form I when subjected to relative humidity between 0-95% and no change in the crystalline form was observed (see, e.g., Example 3 and FIG. 7). Form I also demonstrated favorable stability. For example, stability of Form I up to seven days under high humidity was demonstrated by XRPD analysis.

While several polymorphs other than Form I of Compound (I) were identified, it was also discovered that subjecting these forms to certain conditions (e.g., drying), resulted in controlled conversion among the forms (see FIG. 1).

Characterization of Polymorphs

In certain embodiments, the compounds of the invention are identifiable on the basis of characteristic peaks in an X-ray powder diffraction analysis. X-ray powder diffraction, also referred to as XRPD, is a scientific technique using X-ray, neutron, or electron diffraction on powder, microcrystalline, or other solid materials for structural characterization of the materials.

1. Form I

In one aspect, provided herein is 2-((2-chlorophenyl)(phenyl)amino)-N-(7-(hydroxyamino)-7-oxoheptyl)pyrimidine-5-carboxamide of Form I (referred to herein as "Form I"). Form I (of Compound (I)) was observed under a polarized microscope and its crystalline nature was determined by using X-ray powder diffraction (XRPD) and Pattern A was assigned to it for identification (See Example 3). The chemical structure of the material was confirmed by proton-nuclear magnetic resonance ($^1$H-NMR) and the thermal characterization of the material was carried out by differential scanning calorimetry (DSC) and thermal gravimetric analysis (TGA) (see Examples 2 and 3). The dynamic vapor sorption (DVS) experiment revealed less than 0.2% of moisture uptake by Compound (I), Form I, Pattern A, when subjected to relative humidity between 0-95 percent and no change in the crystalline form was observed (see FIGS. 6 and 7). Karl Fischer (KF) titration also revealed less than 1% of water content. A solid form stability test (up to 7 days) under high humidity was performed on Compound (I), Form I, Pattern A. The XRPD analysis also revealed that the physical form of the material is stable under high humidity up to a week. The XRPD analysis of this form including peak identification is found in Example 11 (See FIG. 40).

The solubility of Form I, Pattern A was determined in 15 solvent/solvent mixtures (see Example 3, part II). The material was found to be freely soluble (>100 mg/mL) in MeOH, TFE and DMA; moderately soluble (between 10-55 mg/mL) in EtOH, THF, acetone:$H_2O$ (1:1) and EtOH:$H_2O$ (1:1) and slightly soluble (≈2 mg/mL) in acetone and IPA. In acetonitrile, water, heptane, DCM, TBME and EtOAc the API was less soluble (<1 mg/mL).

In an embodiment, Form I is characterized by X-ray powder diffraction pattern having peaks expressed in degrees-2-theta at angles 8.3±0.2°, 10.6±0.2°, 16.6±0.2°, 21.3±0.2°, and 25.0±0.2°.

In an embodiment, Form I is characterized by an X-ray powder diffraction pattern having peaks expressed in degrees 2-Theta at angles 8.31±0.2°, 10.62±0.2°, 16.60±0.2°, 19.99±0.2°, 21.33±0.2°, and 24.95±0.2°.

In an embodiment, Form I is characterized by an X-ray powder diffraction pattern having peaks expressed in degrees 2-Theta at angles 8.31±0.2°, 10.00±0.2°, 10.62±0.2°, 16.60±0.2°, 19.99±0.2°, 20.64±0.2°, 21.08±0.2°, 21.33±0.2°, and 24.95±0.2°.

In an embodiment, Form I is characterized by an X-ray powder diffraction pattern having peaks expressed in degrees 2-Theta at angles 8.31±0.2°, 10.00±0.2°, 10.62±0.2°, 12.82±0.2°, 15.62±0.2°, 16.60±0.2°, 17.20±0.2°, 17.67±0.2°, 19.63±0.2°, 19.99±0.2°, 20.64±0.2°, 21.08±0.2°, 21.33±0.2°, 24.41±0.2°, 24.95±0.2°, and 26.08±0.2°.

Figure 40:
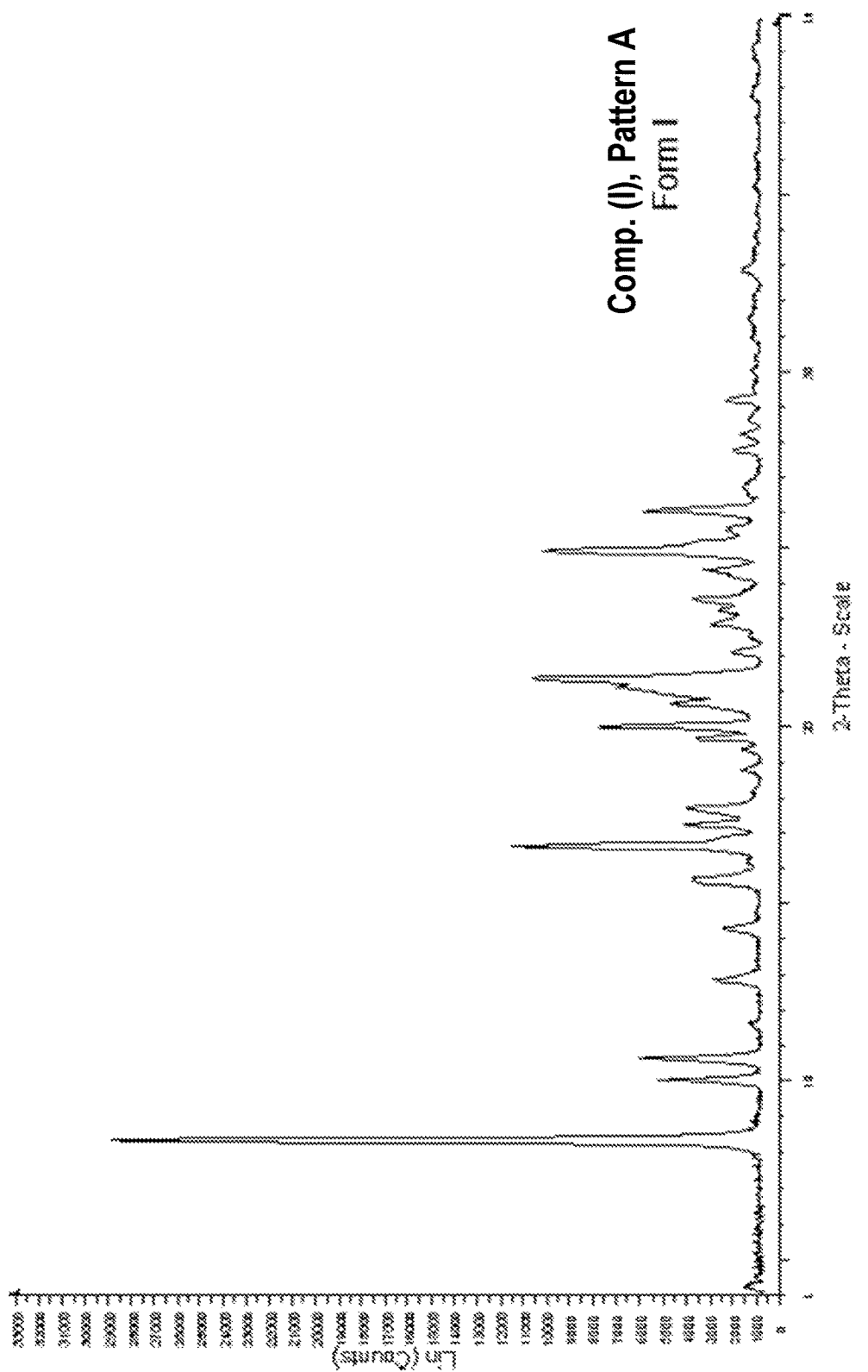
FIG. 40 shows the XRPD pattern of Pattern A, Form I.

In an embodiment, Form I is characterized by an X-ray powder diffraction pattern that is substantially the same as that of FIG. 40.

Figure 4:
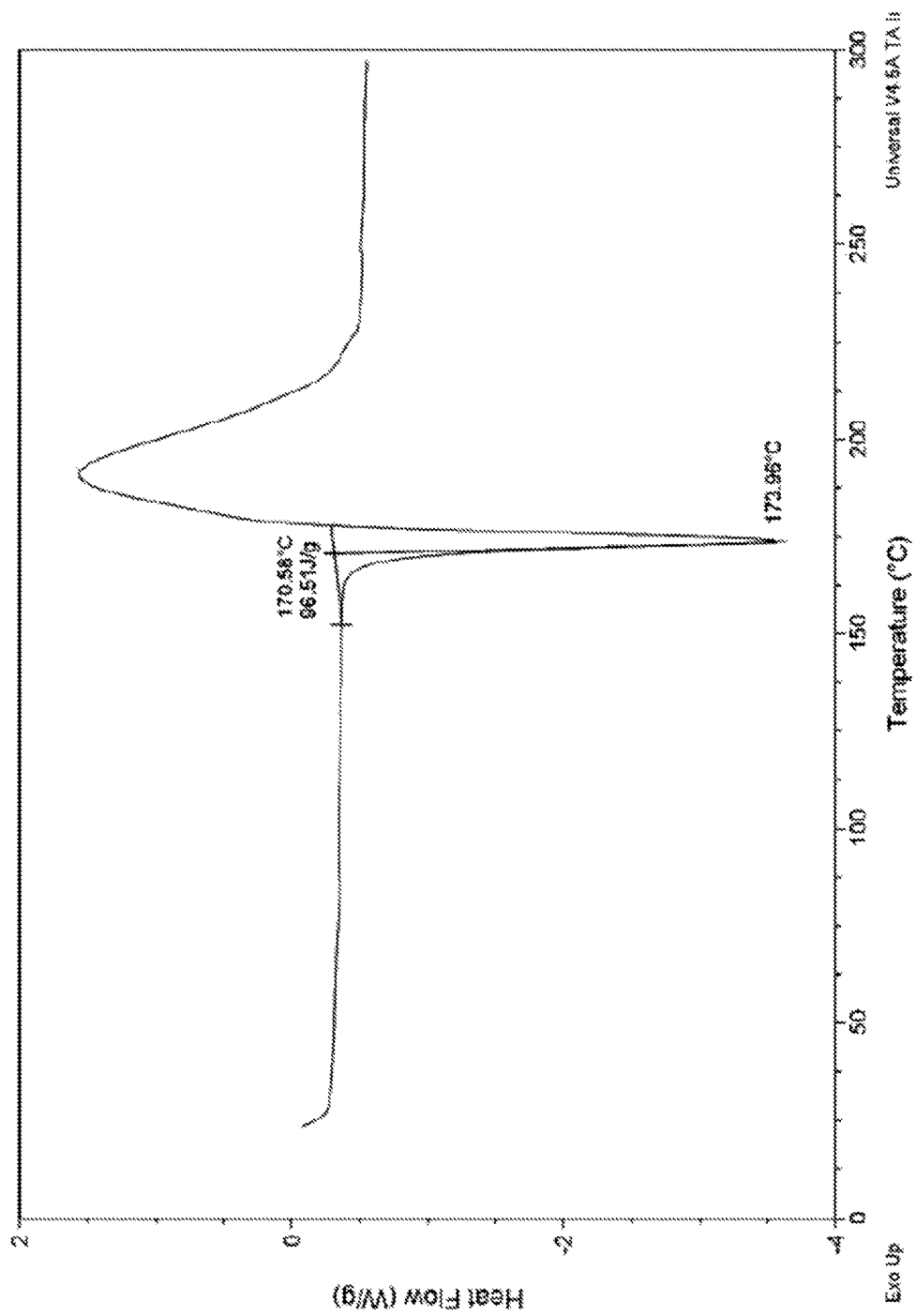
FIG. 4 shows the DSC thermogram of Form I.

In another embodiment, Form I is characterized by a melting point at about 173° C. In a further embodiment, Form I is characterized by a melting point at 173±2° C. In a further embodiment, this melting point is determined by DSC. In yet a further embodiment, Form I is characterized by a DSC thermogram that is substantially the same as that of FIG. 4.

In another embodiment, Form I is substantially free of other crystalline forms of 2-((2-chlorophenyl)(phenyl)amino)-N-(7-(hydroxyamino)-7-oxoheptyl)pyrimidine-5-carboxamide (e.g., Forms II, III, IV, V, VI, VII, VIII, and/or IX). As used herein, the term "substantially free" means that Form I contains no significant amount of Forms II, III, IV, V, VI, VII, VIII, and/or IX. In an embodiment, provided herein is a composition comprising Compound (I) of Form I, wherein the composition is substantially free of any other crystalline forms of Compound (I).

2. Form II

Figure 16:
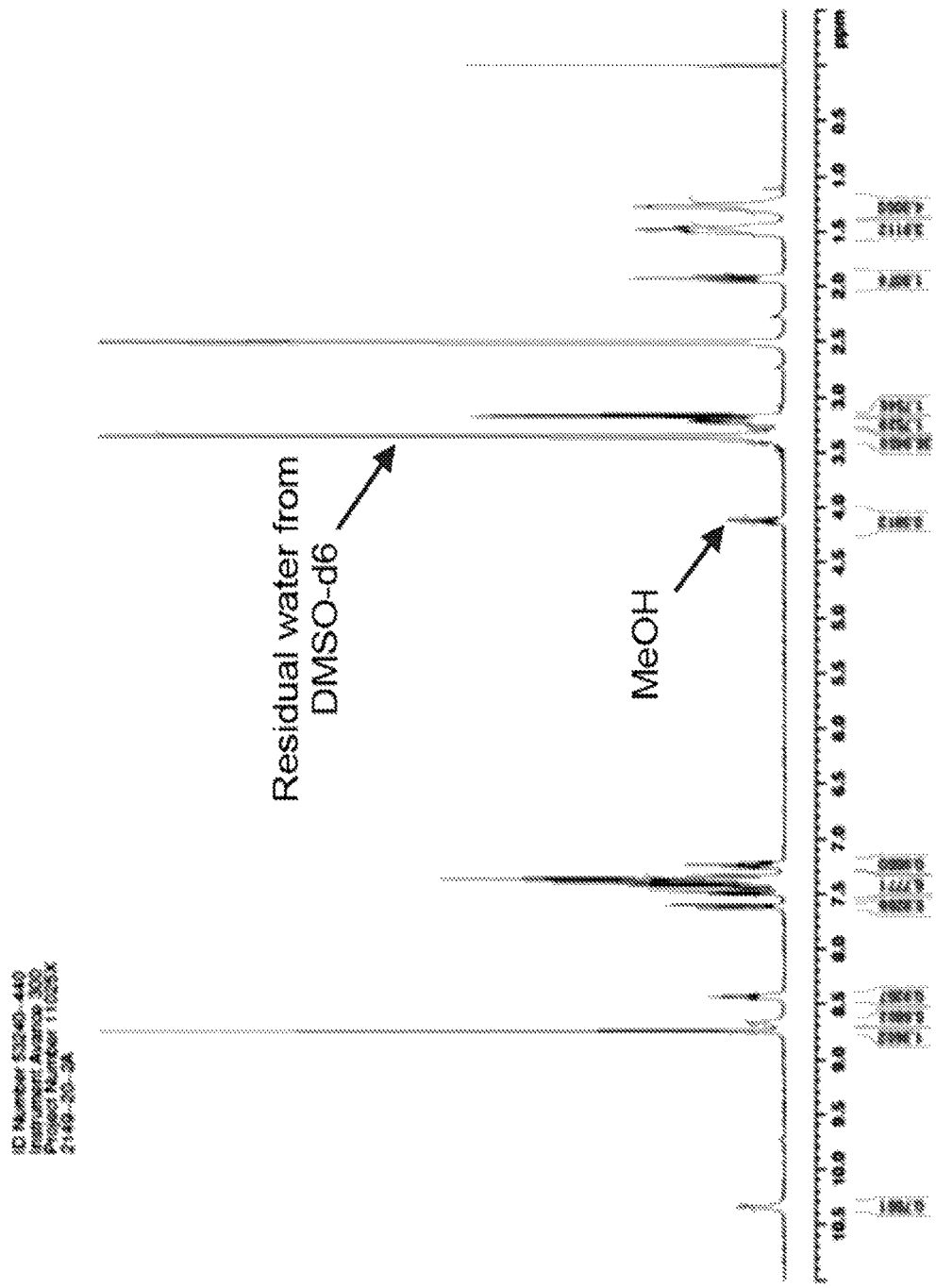
FIG. 16 shows the $^1$H-NMR data of Form II (Pattern B).

In one aspect, provided herein is 2-((2-chlorophenyl)(phenyl)amino)-N-(7-(hydroxyamino)-7-oxoheptyl)pyrimidine-5-carboxamide of Form II (referred to herein as "Form II"). Slurry experiments of Compound (I) in MeOH at 15° C. resulted in the isolation of a new XRPD pattern, namely, Pattern B or Form II (See, e.g., Example 4). Slow evaporation of Compound (I) in MeOH (75 mg in 0.75 mL) also resulted in Pattern B or Form II. $^1$H-NMR analysis on Pattern B was performed to identify the chemical structure of the new forms obtained (see FIG. 16). Pattern B was found to be a hemi-methanol solvate.

It has also been found that in MeOH, Pattern B (Form II) was found to be the stable form after 24 h slurry at 15° C. and 60° C. (see Example 9).

Figure 8:
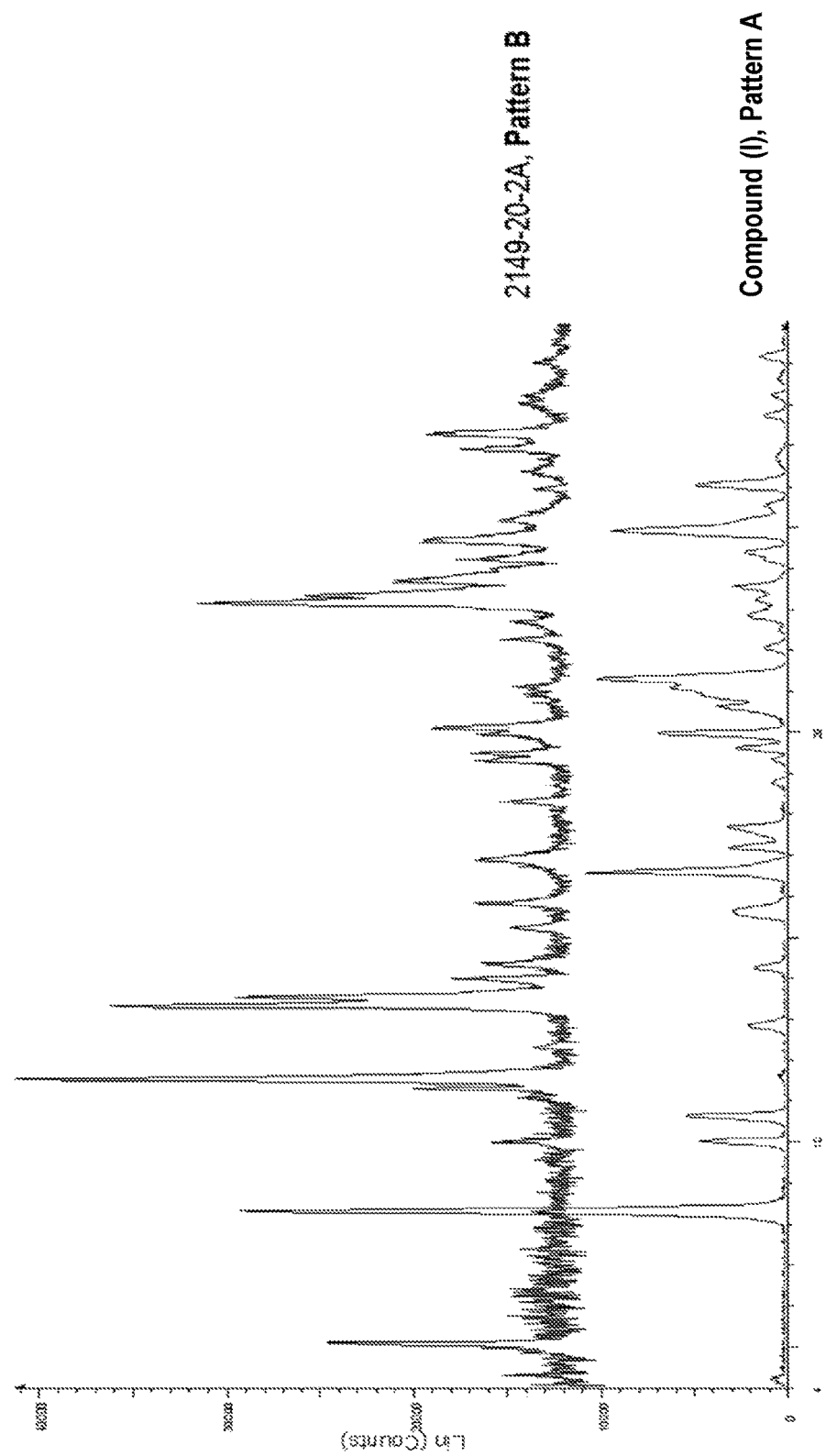
FIG. 8 shows a comparison of XRPD patterns of Form I (Pattern A) and Form II (Pattern B).
Figure 41:
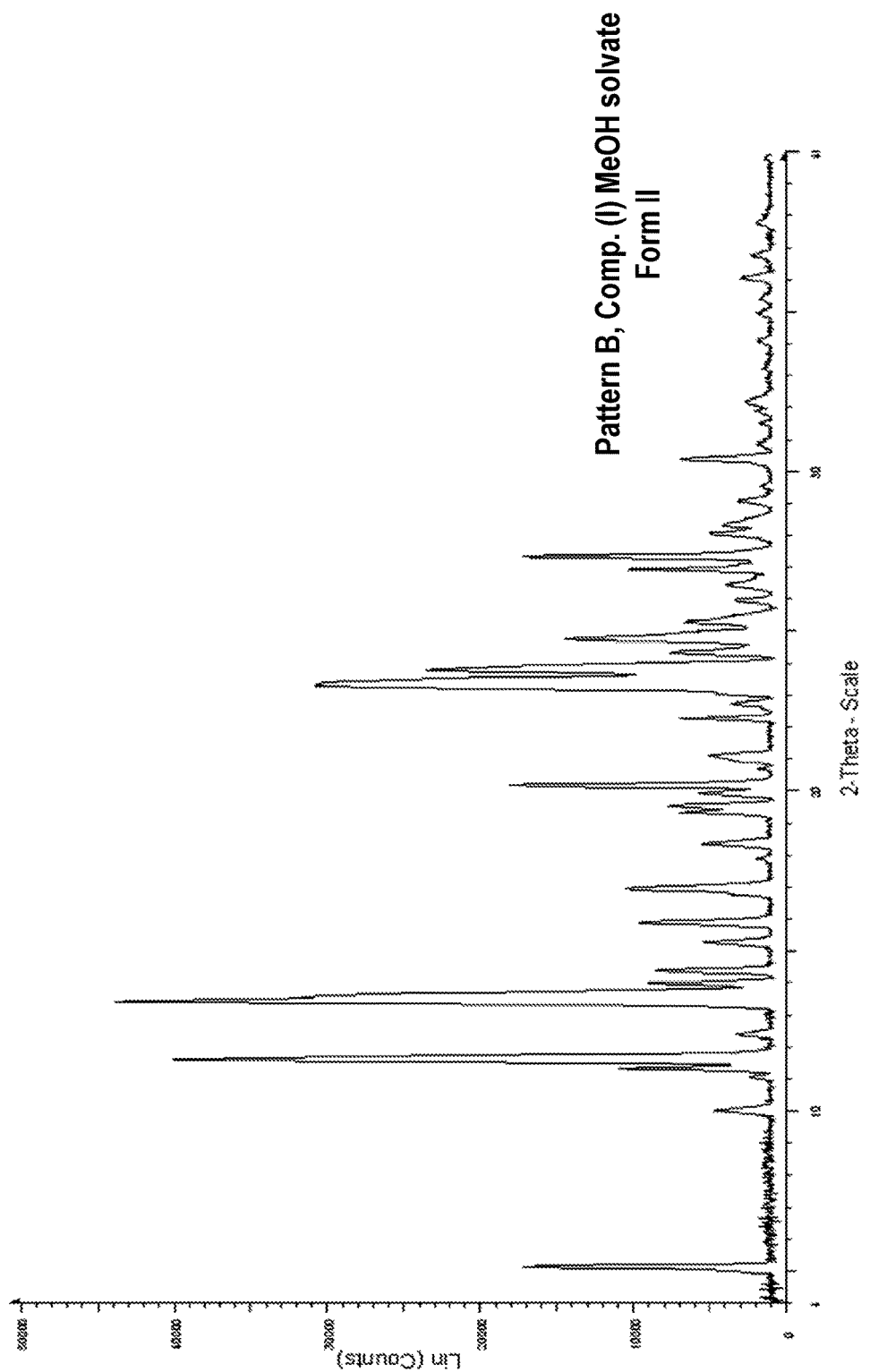
FIG. 41 shows the XRPD pattern of Pattern B, Form II.

The XRPD analysis of this form (Form II, Pattern B) in comparison with Form I (Pattern A) is shown in FIG. 8, and the XRPD analysis including peak identification is found in Example 12 (see FIG. 41).

In an embodiment, Form II is characterized by an X-ray powder diffraction pattern having peaks expressed in degrees 2-Theta at angles 11.6±0.2°, 19.5±0.2°, 20.2±0.2°, 23.3±0.2°, and 23.8±0.2°.

In an embodiment, Form II is characterized by an X-ray powder diffraction pattern having peaks expressed in degrees 2-Theta at angles 5.07±0.2°, 11.58±0.2°, 15.86±0.2°, 16.93±0.2°, 19.52±0.2°, 20.16±0.2°, 23.33±0.2°, 23.80±0.2°, 24.78±0.2°, 26.94±0.2° and 27.35±0.2°.

In an embodiment, Form II is characterized by an X-ray powder diffraction pattern having peaks expressed in degrees 2-Theta at angles 5.07±0.2°, 11.58±0.2°, 13.96±0.2°, 14.37±0.2°, 15.86±0.2°, 16.93±0.2°, 19.33±0.2°, 19.53±0.2°, 20.16±0.2°, 22.28±0.2°, 23.33±0.2°, 23.80±0.2°, 24.78±0.2°, 25.31±0.2°, 26.94±0.2° and 27.35±0.2°.

In an embodiment, Form II is characterized by an X-ray powder diffraction pattern that is substantially the same as that of FIG. 41.

3. Form III

Figure 9:
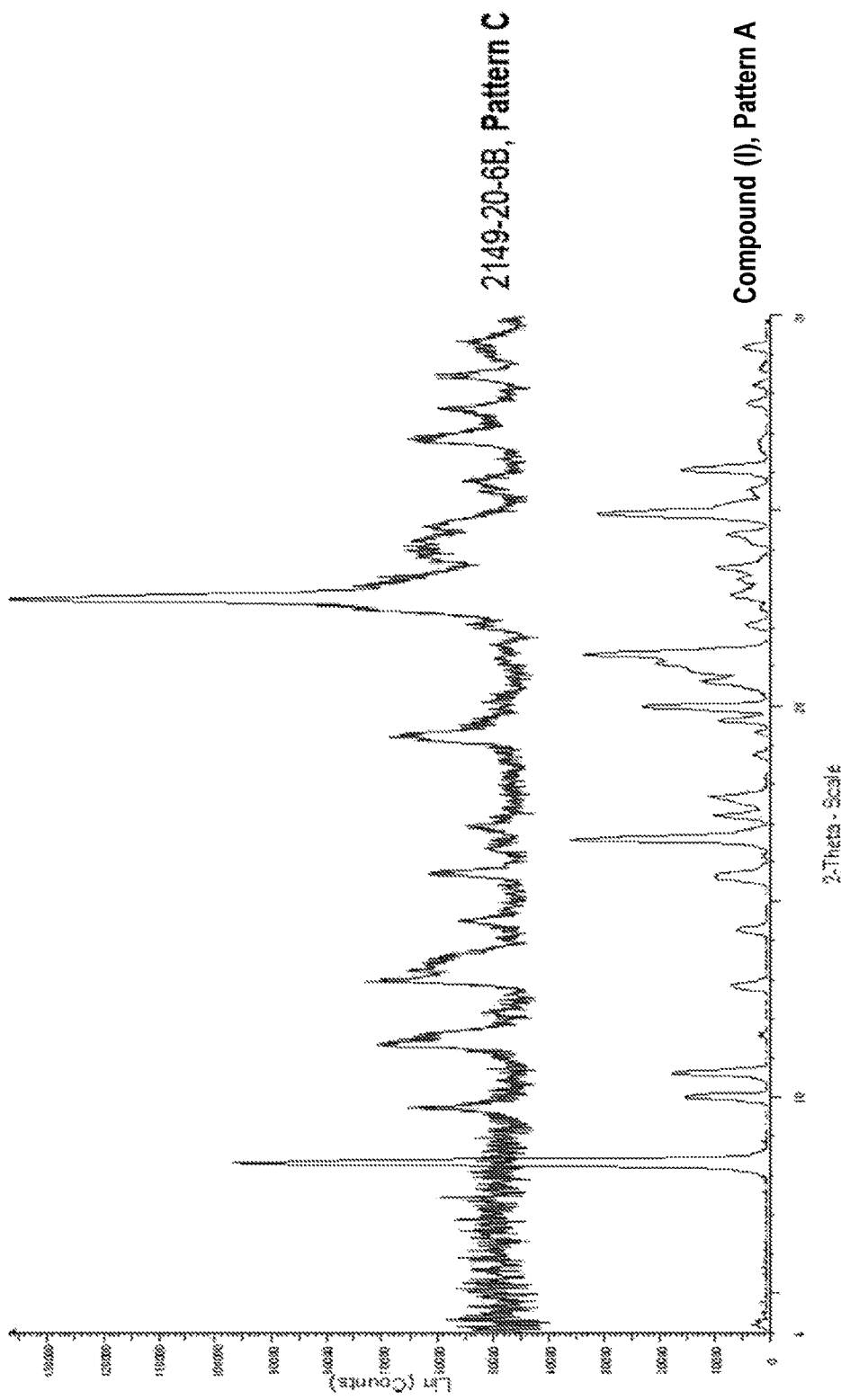
FIG. 9 shows a comparison of XRPD patterns of Form I (Pattern A) and Form III (Pattern C).

In one aspect, provided herein is 2-((2-chlorophenyl)(phenyl)amino)-N-(7-(hydroxyamino)-7-oxoheptyl)pyrimidine-5-carboxamide of Form III (referred to herein as "Form III"). Slurry experiments of Compound (I) in DCM at 15° C. resulted in the isolation of a new XRPD pattern, namely, Pattern C or Form III (See, e.g., Example 4). $^1$H-NMR analysis on Pattern C was performed to identify the chemical structure of the new forms obtained. Pattern C was found to be a hemi-DCM solvate. The XRPD analysis of this form (Form III, Pattern C) in comparison with Form I (Pattern A) is shown in FIG. 9, and the XRPD analysis including peak identification is found in Example 13 (see FIG. 42).

In an embodiment, Form III is characterized by an X-ray powder diffraction pattern having peaks expressed in degrees 2-Theta at angles 8.3±0.2°, 11.7±0.2°, 13.5±0.2°, 13.7±0.2°, and 23.6±0.2°.

In an embodiment, Form III is characterized by an X-ray powder diffraction pattern having peaks expressed in degrees 2-Theta at angles 5.07±0.2°, 8.3±0.2°, 11.69±0.2°, 13.52±0.2°, 13.69±0.2°, 23.57±0.2°, and 23.99±0.2°.

In an embodiment, Form III is characterized by an X-ray powder diffraction pattern having peaks expressed in degrees 2-Theta at angles 5.07±0.2°, 8.3±0.2°, 11.69±0.2°, 13.52±0.2°, 13.69±0.2°, 15.91±0.2°, 17.05±0.2°, 20.26±0.2°, 23.57±0.2°, 23.99±0.2°, 24.58±0.2°, 25.04±0.2°, 26.89±0.2°, and 27.3±0.2°.

In an embodiment, Form III is characterized by an X-ray powder diffraction pattern having peaks expressed in degrees 2-Theta at angles 5.07±0.2°, 8.31±0.2°, 11.69±0.2°, 13.52±0.2°, 13.69±0.2°, 14.45±0.2°, 15.91±0.2°, 17.05±0.2°, 20.26±0.2°, 21.10±0.2°, 23.57±0.2°, 23.99±0.2°, 24.58±0.2°, 25.04±0.2°, 26.89±0.2°, and 27.3±0.2°.

Figure 42:
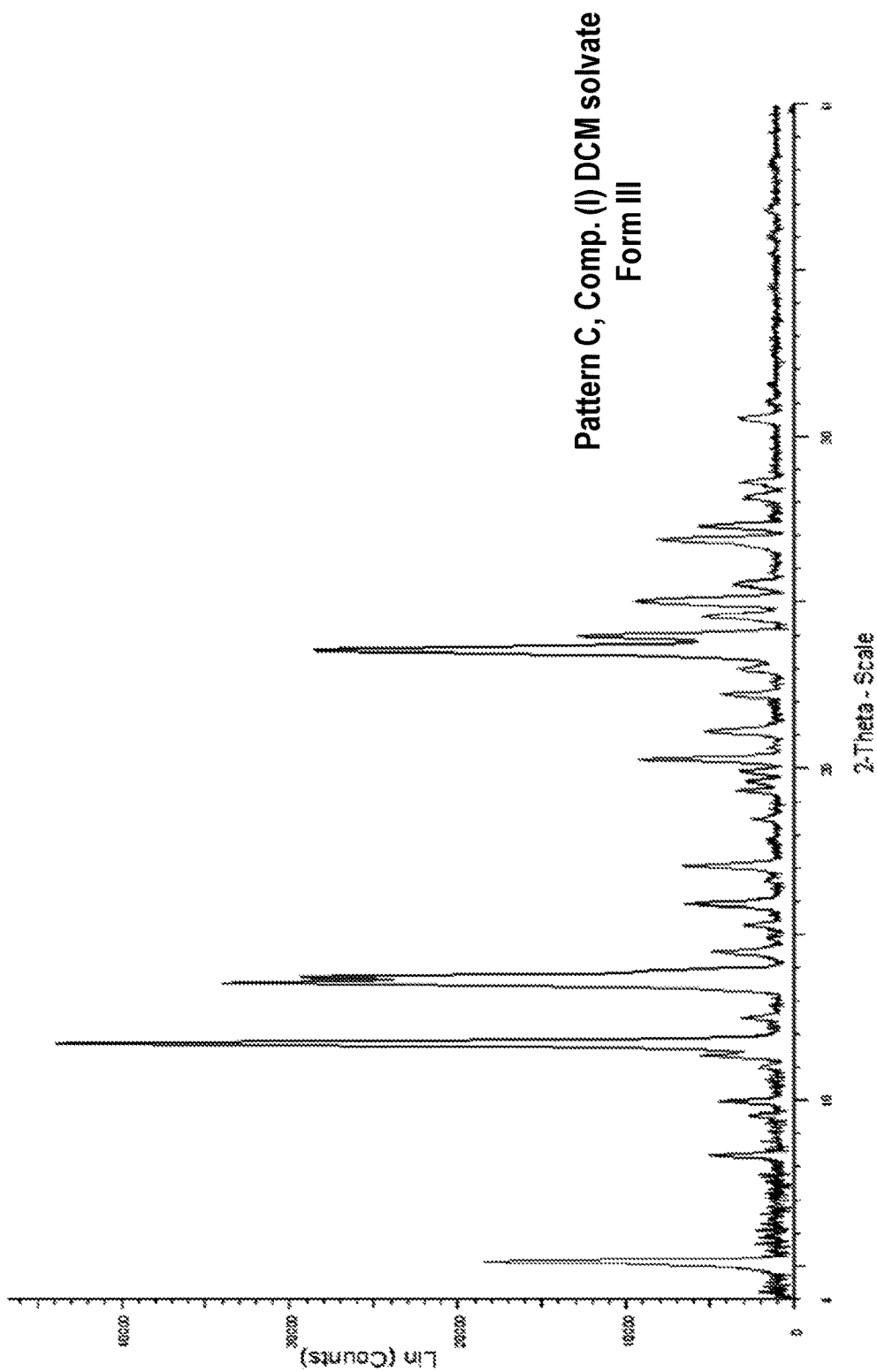
FIG. 42 shows the XRPD pattern of Pattern C, Form III.

In an embodiment, Form III is characterized by an X-ray powder diffraction pattern that is substantially the same as that of FIG. 42.

4. Form IV

Figure 20:
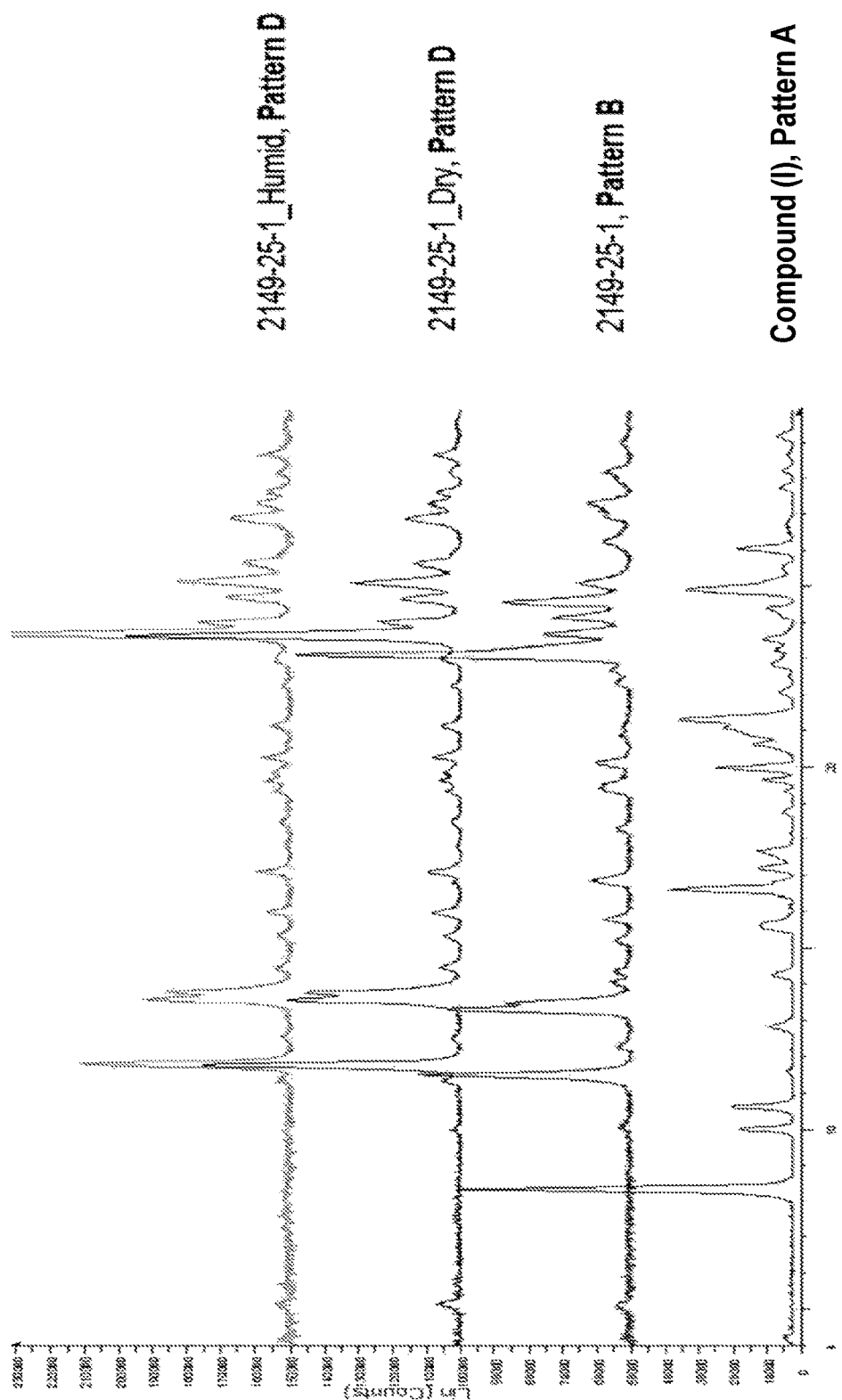
FIG. 20 shows a comparison of XRPD patterns of Form I (Pattern A) with Form II (Pattern B), dry (Pattern D) and humid (Pattern D) samples.
Figure 21:
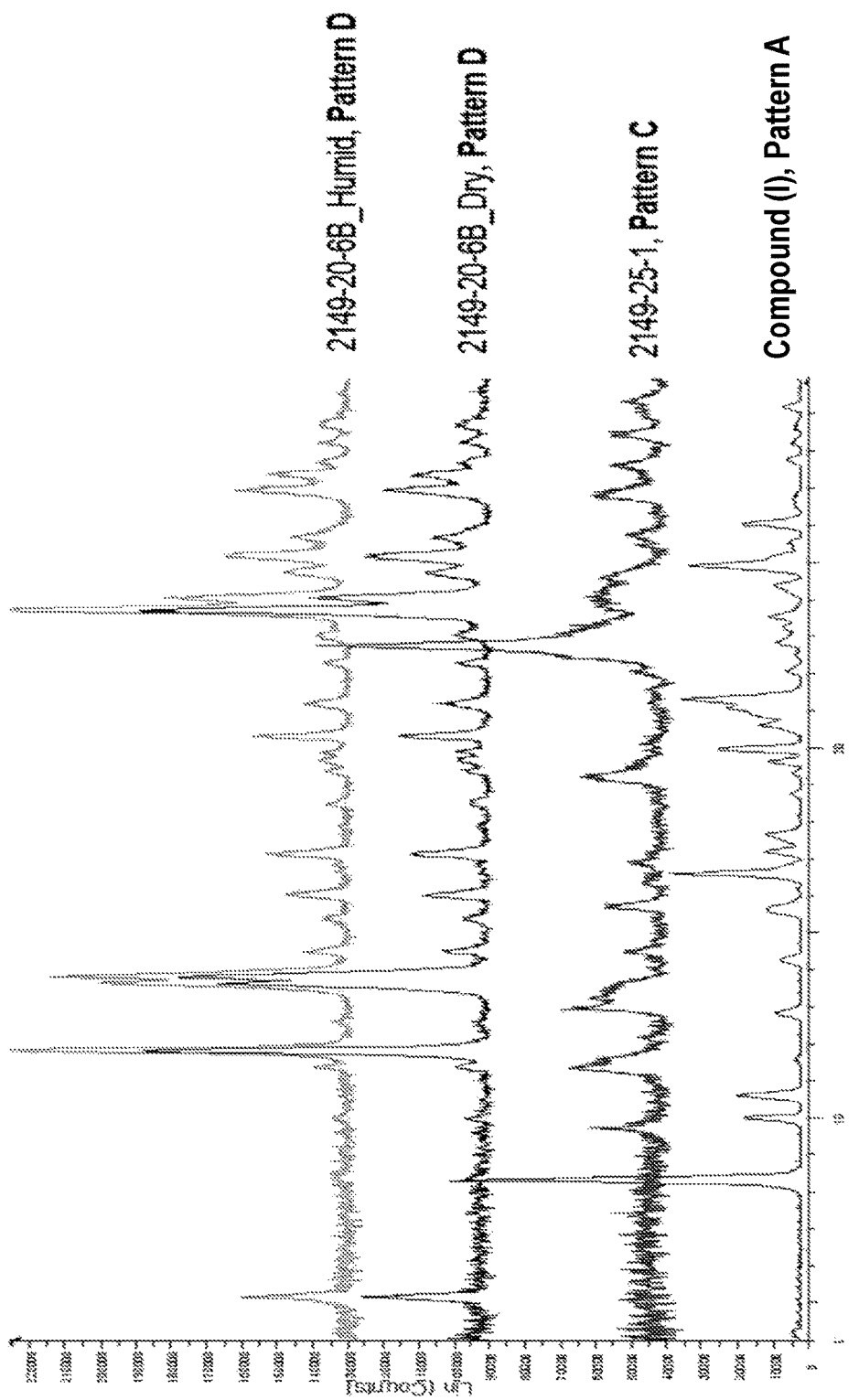
FIG. 21 shows a comparison of XRPD patterns of Form I (Pattern A) with Form III (Pattern C), dry (Pattern D) and humid (Pattern D) samples.

In one aspect, provided herein is 2-((2-chlorophenyl)(phenyl)amino)-N-(7-(hydroxyamino)-7-oxoheptyl)pyrimidine-5-carboxamide of Form IV (referred to herein as "Form IV"). Form IV can be formed by drying Forms II or III of Compound (I) under vacuum (see, e.g., Example 8). The XRPD analysis of the transformation (formation of Form IV, Pattern D) from Form II (Pattern B) is shown in FIG. 20. The XRPD analysis of the transformation (formation of Form IV, Pattern D) from Form III (Pattern C) is shown in FIG. 21. An XRPD analysis including peak identification is found in Example 14 (see FIG. 43).

In an embodiment, Form IV is characterized by an X-ray powder diffraction pattern having peaks expressed in degrees 2-Theta at angles 11.8±0.2°, 13.6±0.2°, 13.8±0.2°, 23.7±0.2°, and 30.6±0.2°.

In an embodiment, Form IV is characterized by an X-ray powder diffraction pattern having peaks expressed in degrees 2-Theta at angles 5.13±0.2°, 11.78±0.2°, 13.60±0.2°, 13.80±0.2°, 20.30±0.2°, 23.69±0.2°, 24.05±0.2°, 25.16±0.2°, and 30.61±0.2°.

In an embodiment, Form IV is characterized by an X-ray powder diffraction pattern having peaks expressed in degrees 2-Theta at angles 5.13±0.2°, 11.78±0.2°, 13.60±0.2°, 13.80±0.2°, 14.48±0.2°, 16.01±0.2°, 17.13±0.2°, 20.30±0.2°, 21.16±0.2°, 23.69±0.2°, 24.05±0.2°, 24.70±0.2°, 25.16±0.2°, 26.95±0.2°, 27.36±0.2°, and 30.61±0.2°.

In an embodiment, Form IV is characterized by an X-ray powder diffraction pattern having peaks expressed in degrees 2-Theta at angles 5.13±0.2°, 11.78±0.2°, 13.60±0.2°, 13.80±0.2°, 14.48±0.2°, 16.01±0.2°, 17.13±0.2°, 20.30±0.2°, 21.16±0.2°, 23.69±0.2°, 24.05±0.2°, 24.70±0.2°, 25.16±0.2°, 26.95±0.2°, 27.36±0.2°, and 30.61±0.2°.

Figure 43:
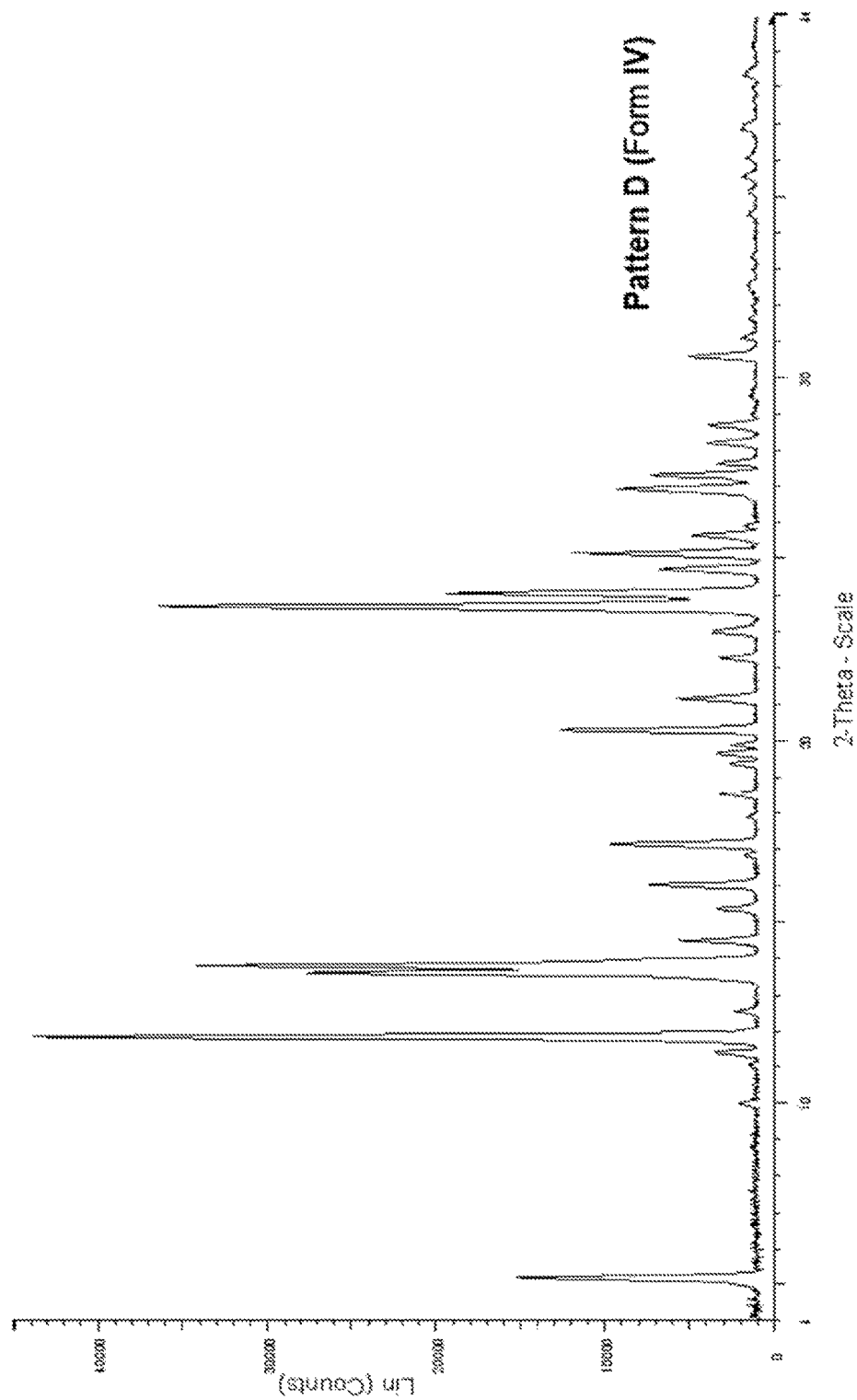
FIG. 43 shows the XRPD pattern of Pattern D, Form IV.

In an embodiment, Form IV is characterized by an X-ray powder diffraction pattern that is substantially the same as that of FIG. 43.

In another embodiment, Form IV is substantially free of Forms I, II, III, V, VI, VII, VIII, and/or IX.

5. Form V

Figure 10:
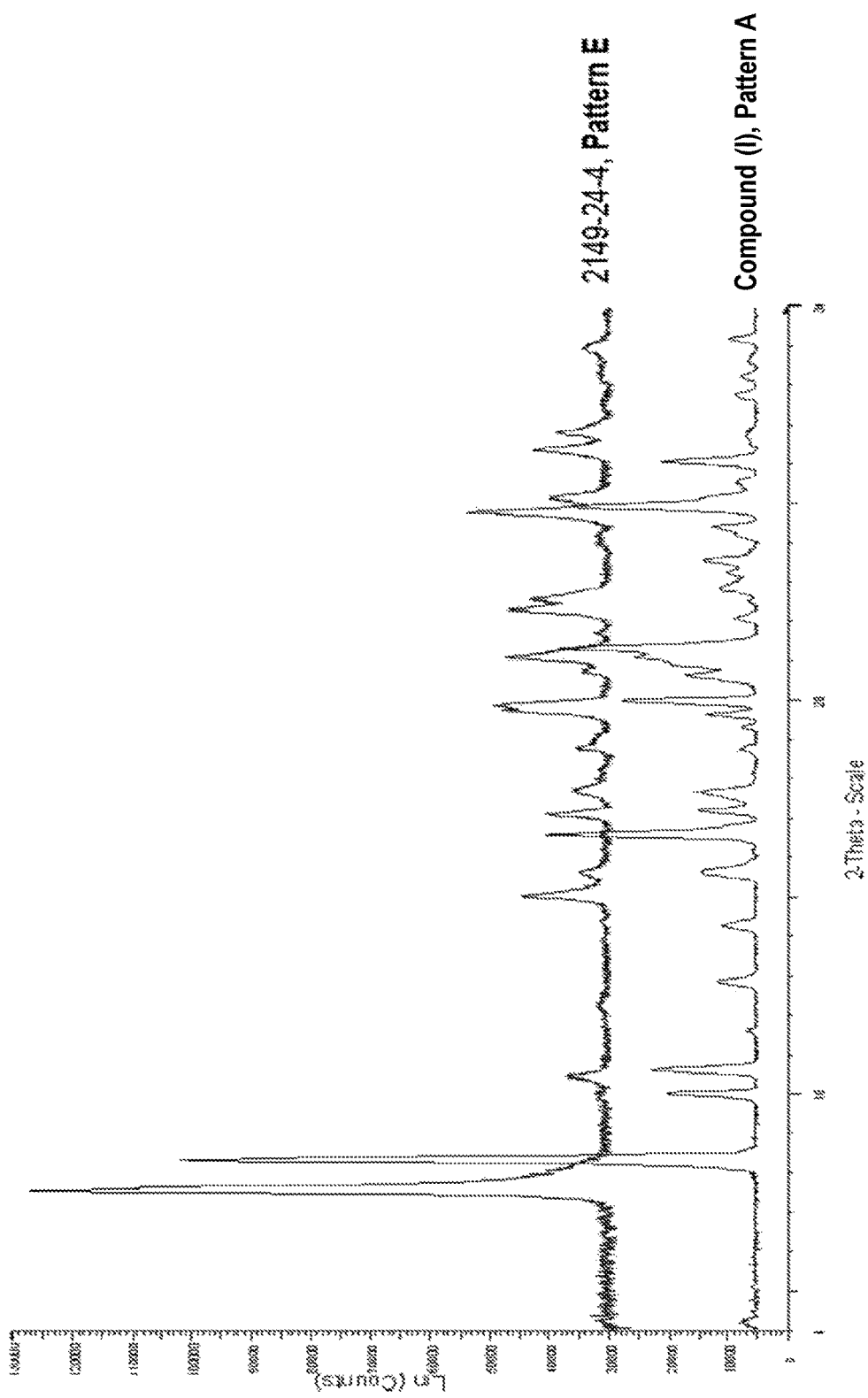
FIG. 10 shows a comparison of XRPD patterns of Form V (Pattern E) with Form I (Pattern A).

In one aspect, provided herein is 2-((2-chlorophenyl)(phenyl)amino)-N-(7-(hydroxyamino)-7-oxoheptyl)pyrimidine-5-carboxamide of Form V (referred to herein as "Form V"). Form V can be formed by, for example, the fast cooling experiment described in Example III, part III (see Table 5, sample no. 4). Scale-up and characterization of Form V, Pattern E is described in Example 5. The XRPD analysis of this form (Form V, Pattern E) in comparison with Form I (Pattern A) is shown in FIG. 10, and the XRPD analysis including peak identification is found in Example 15 (see FIG. 44).

In an embodiment, Form V is characterized by an X-ray powder diffraction pattern having peaks expressed in degrees 2-Theta at angles 7.6±0.2°, 15.1±0.2°, 21.1±0.2°, and 24.8±0.2°.

In an embodiment, Form V is characterized by an X-ray powder diffraction pattern having peaks expressed in degrees 2-Theta at angles 7.55±0.2°, 15.05±0.2°, 19.80±0.2°, 21.14±0.2°, 22.33±0.2°, 22.59±0.2°, 24.82±0.2°, and 25.20±0.2°.

In an embodiment, Form V is characterized by an X-ray powder diffraction pattern having peaks expressed in degrees 2-Theta at angles 7.55±0.2°, 10.48±0.2°, 15.05±0.2°, 15.66±0.2°, 17.14±0.2°, 17.73±0.2°, 18.80±0.2°, 19.80±0.2°, 21.14±0.2°, 21.76±0.2°, 22.33±0.2°, 22.59±0.2°, 24.82±0.2°, 25.20±0.2°, 26.40±0.2° and 26.86±0.2°.

Figure 44:
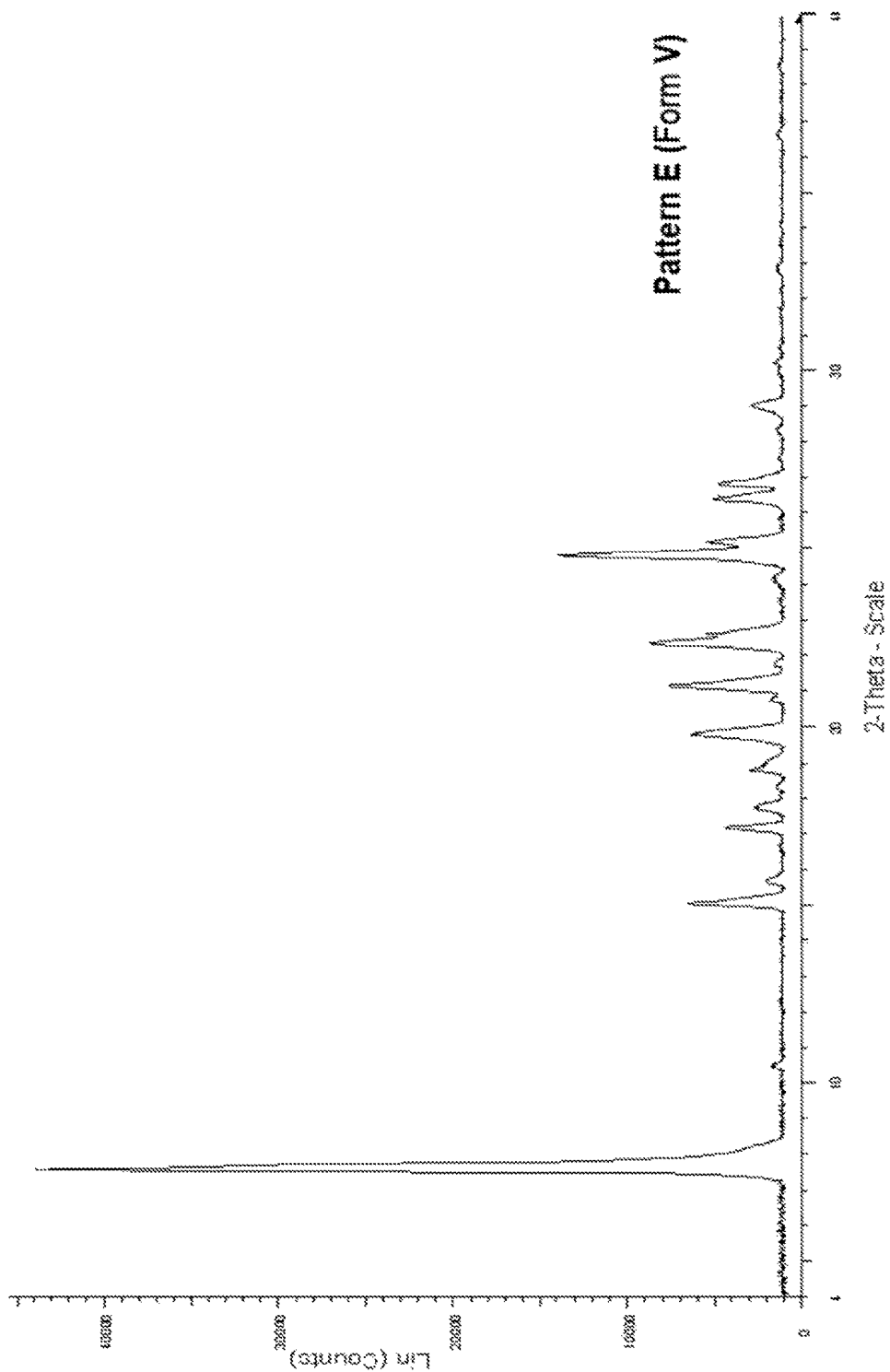
FIG. 44 shows the XRPD pattern of Pattern E, Form V.

In an embodiment, Form V is characterized by an X-ray powder diffraction pattern that is substantially the same as that of FIG. 44.

6. Form VI

Figure 26:
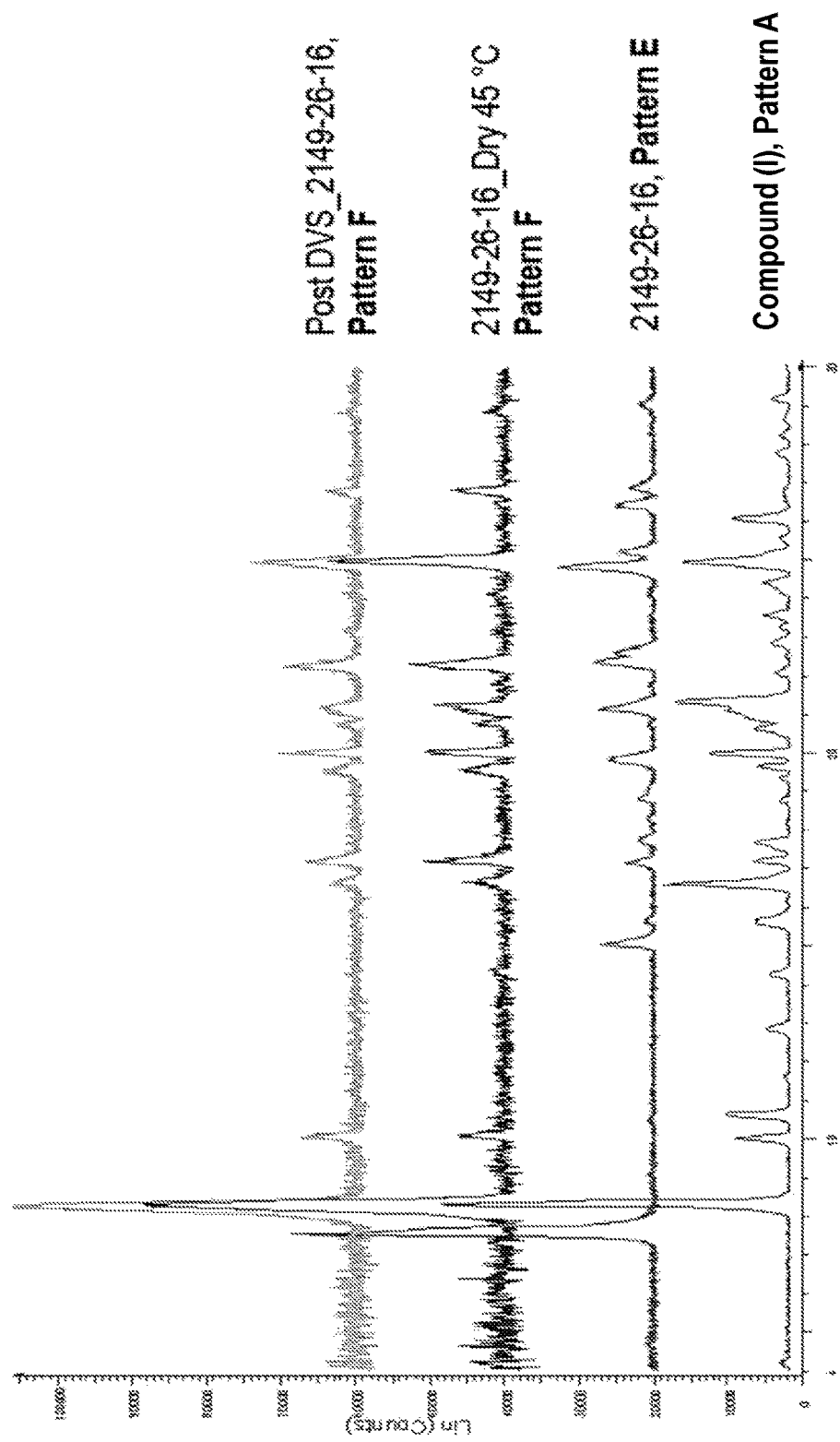
FIG. 26 shows a comparison of XRPD patterns of Form I, with pre- and post-DVS of Form V, Pattern E.

In one aspect, provided herein is 2-((2-chlorophenyl)(phenyl)amino)-N-(7-(hydroxyamino)-7-oxoheptyl)pyrimidine-5-carboxamide of Form VI (referred to herein as "Form VI"). It was found that drying Form V, Pattern E under vacuum at 45° C. results in the form change to Form VI, Pattern F. The XRPD analysis of this transformation (formation of Form VI, Pattern F) from Form V (Pattern E) is shown in FIG. 26. XRPD analysis including peak identification is found in Example 16 (see FIG. 45).

In an embodiment, Form VI is characterized by an X-ray powder diffraction pattern having peaks expressed in degrees 2-Theta at angles 8.2±0.2°, 20.0±0.2°, 22.2±0.2°, and 24.9±0.2°.

In an embodiment, Form VI is characterized by an X-ray powder diffraction pattern having peaks expressed in degrees 2-Theta at angles 8.24±0.2°, 10.00±0.2°, 17.14±0.2°, 19.96±0.2°, 21.16±0.2°, 22.22±0.2°, and 24.91±0.2°.

In an embodiment, Form VI is characterized by an X-ray powder diffraction pattern having peaks expressed in degrees 2-Theta at angles 8.24±0.2°, 10.00±0.2°, 14.26±0.2°, 15.86±0.2°, 16.59±0.2°, 17.14±0.2°, 19.48±0.2°, 19.96±0.2°, 20.70±0.2°, 21.16±0.2°, 22.22±0.2°, 23.14±0.2°, 24.91±0.2°, 26.74±0.2°, and 28.79±0.2°.

Figure 45:
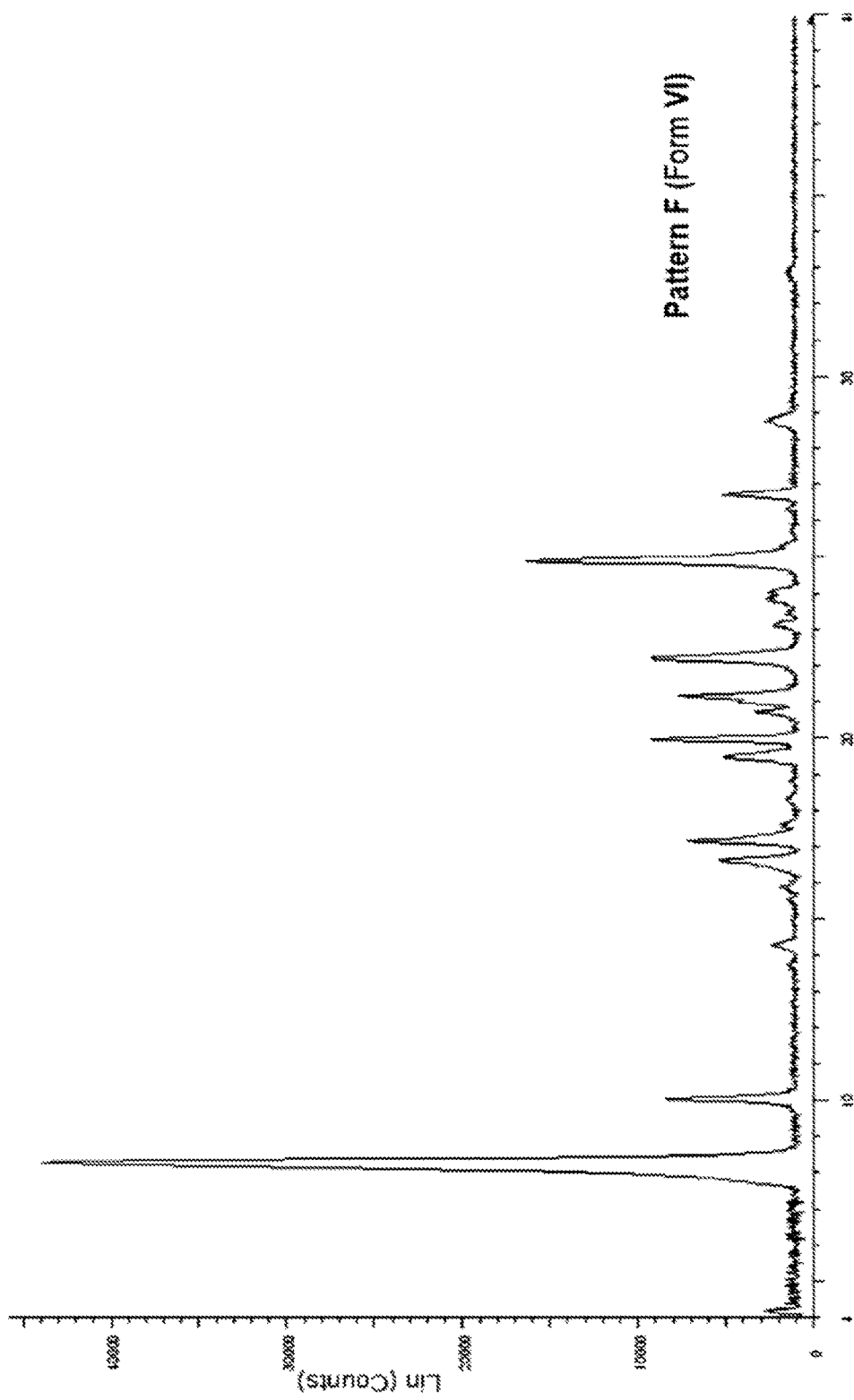
FIG. 45 shows the XRPD pattern of Pattern F, Form VI.

In an embodiment, Form VI is characterized by an X-ray powder diffraction pattern that is substantially the same as that of FIG. 45.

7. Form VII

Figure 11:
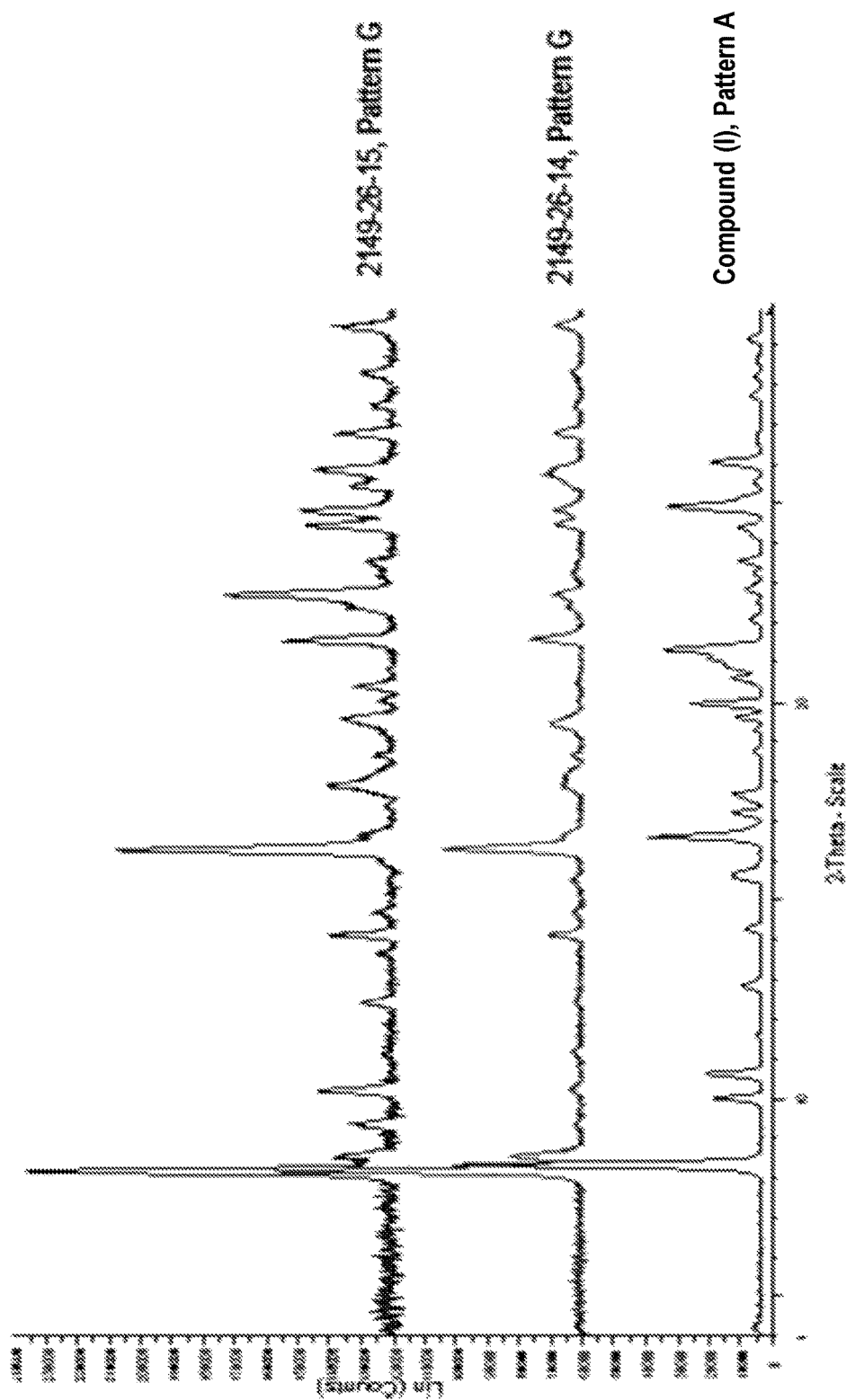
FIG. 11 shows a comparison of XRPD patterns of Form VII (Pattern G) with Form I (Pattern A).

In one aspect, provided herein is 2-((2-chlorophenyl)(phenyl)amino)-N-(7-(hydroxyamino)-7-oxoheptyl)pyrimidine-5-carboxamide of Form VII (referred to herein as "Form VII"). The scale-up and characterization of Form VII, Pattern G is described in Example 6. The XRPD analysis of this form (Form VII, Pattern G) in comparison with Form I (Pattern A) is shown in FIG. 11, and the XRPD analysis including peak identification is found in Example 17 (see FIG. 46).

In an embodiment, Form VII is characterized by an X-ray powder diffraction pattern having peaks expressed in degrees 2-Theta at angles 8.2±0.2°, 8.5±0.2°, 16.3±0.2°, and 21.6±0.2°.

In an embodiment, Form VII is characterized by an X-ray powder diffraction pattern having peaks expressed in degrees 2-Theta at angles 8.15±0.2°, 8.52±0.2°, 14.11±0.2°, 16.29±0.2°, 19.47±0.2°, 21.58±0.2°, and 25.80±0.2°.

In an embodiment, Form VII is characterized by an X-ray powder diffraction pattern having peaks expressed in degrees 2-Theta at angles 8.15±0.2°, 8.52±0.2°, 10.21±0.2°, 14.11±0.2°, 16.29±0.2°, 18.66±0.2°, 19.47±0.2°, 21.58±0.2°, 22.72±0.2°, 24.50±0.2°, 24.86±0.2°, 25.80±0.2°, 26.82±0.2°, and 29.55±0.2°.

Figure 46:
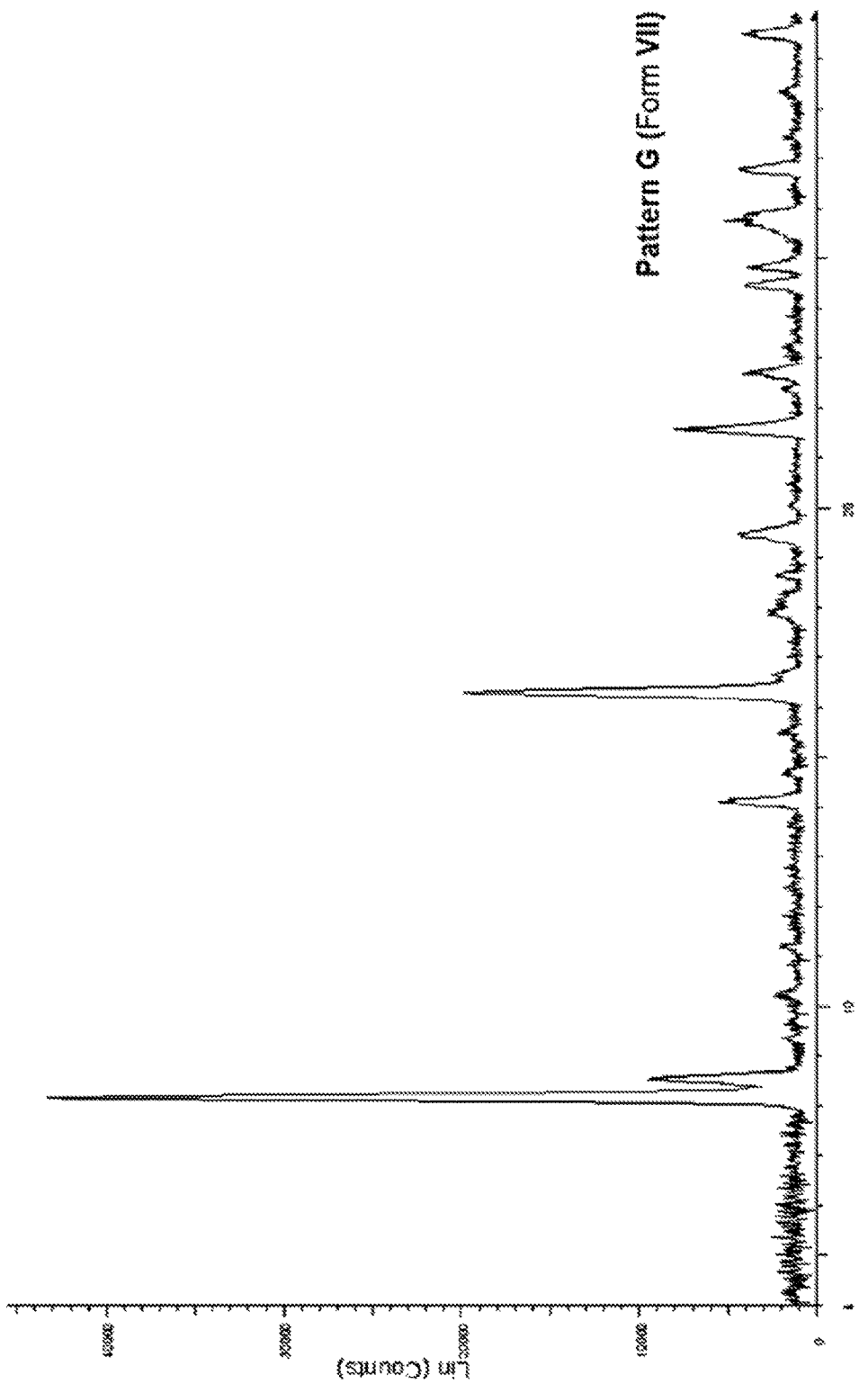
FIG. 46 shows the XRPD pattern of Pattern G, Form VII.

In an embodiment, Form VII is characterized by an X-ray powder diffraction pattern that is substantially the same as that of FIG. 46.

8. Form VIII

Figure 30:
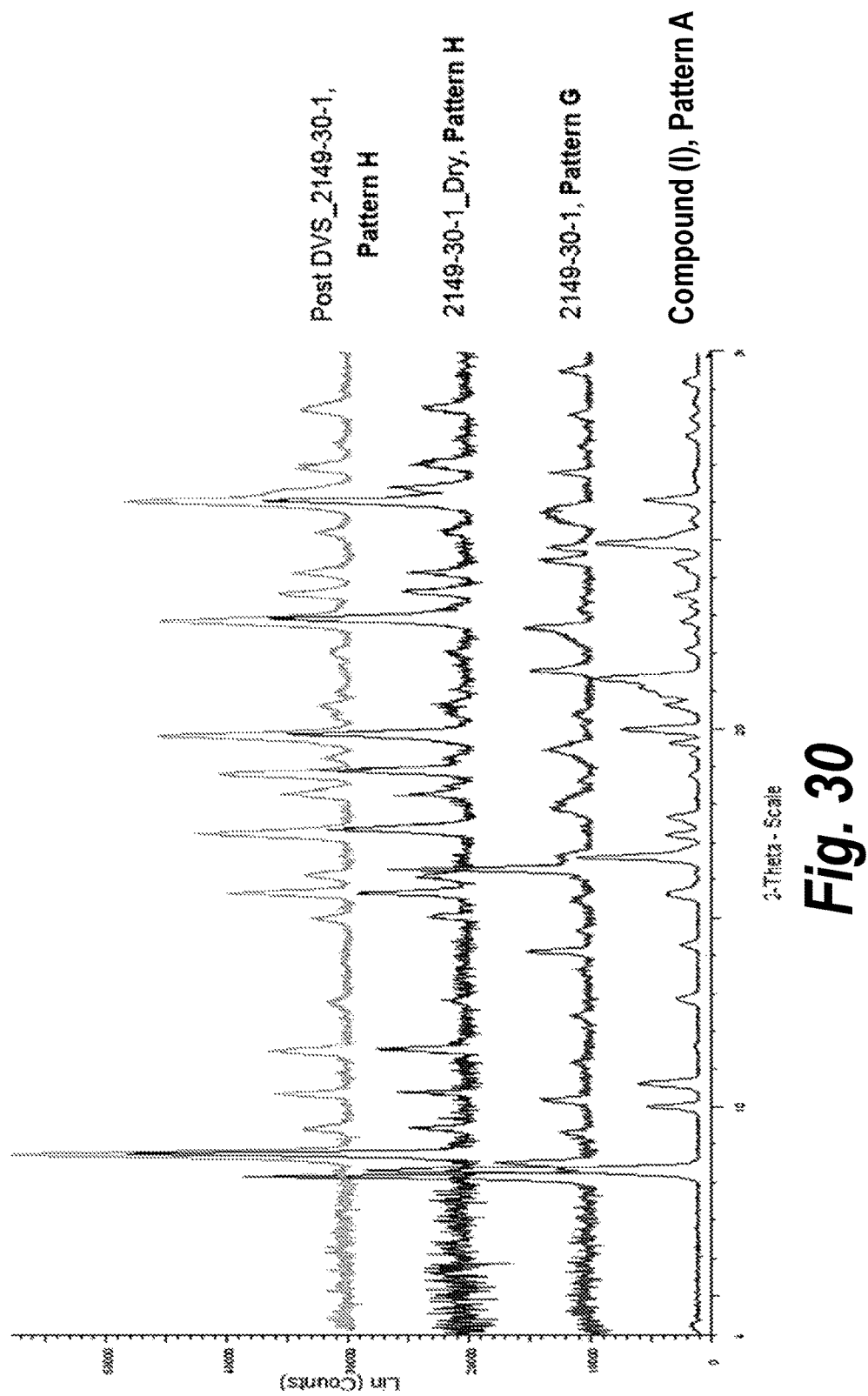
FIG. 30 shows a comparison of XRPD patterns of Form VIII (Pattern H), dry and post DVS with Form I, Pattern A.

In one aspect, provided herein is 2-((2-chlorophenyl)(phenyl)amino)-N-(7-(hydroxyamino)-7-oxoheptyl)pyrimidine-5-carboxamide of Form VIII (referred to herein as "Form VIII"). Form VIII (Pattern H) was identified after subjecting Form VII, Pattern G to vacuum at 45° C. (see Example 6). The XRPD analysis of Form VIII (Pattern H) in comparison with Form I (Pattern A) and Form VII (Pattern G) is shown in FIG. 30, and the XRPD analysis including peak identification is found in Example 18 (see FIG. 47).

In an embodiment, Form VIII is characterized by an X-ray powder diffraction pattern having peaks expressed in degrees 2-Theta at angles 8.7±0.2°, 18.9±0.2°, 19.9±0.2°, and 26.1±0.2°.

In an embodiment, Form VIII is characterized by an X-ray powder diffraction pattern having peaks expressed in degrees 2-Theta at angles 8.73±0.2°, 10.39±0.2°, 11.52±0.2°, 15.66±0.2°, 16.07±0.2°, 17.36±0.2°, 18.92±0.2°, 19.87±0.2°, 23.67±0.2°, 26.07±0.2°, 27.06±0.2°, 28.53±0.2°, and 31.41±0.2°.

In an embodiment, Form VIII is characterized by an X-ray powder diffraction pattern having peaks expressed in degrees 2-Theta at angles 8.73±0.2°, 9.43±0.2°, 10.39±0.2°, 11.52±0.2°, 15.66±0.2°, 16.07±0.2°, 17.36±0.2°, 18.92±0.2°, 19.23±0.2°, 19.87±0.2°, 20.67±0.2°, 23.67±0.2°, 26.07±0.2°, 27.06±0.2°, 28.53±0.2°, and 31.41±0.2°.

Figure 47:
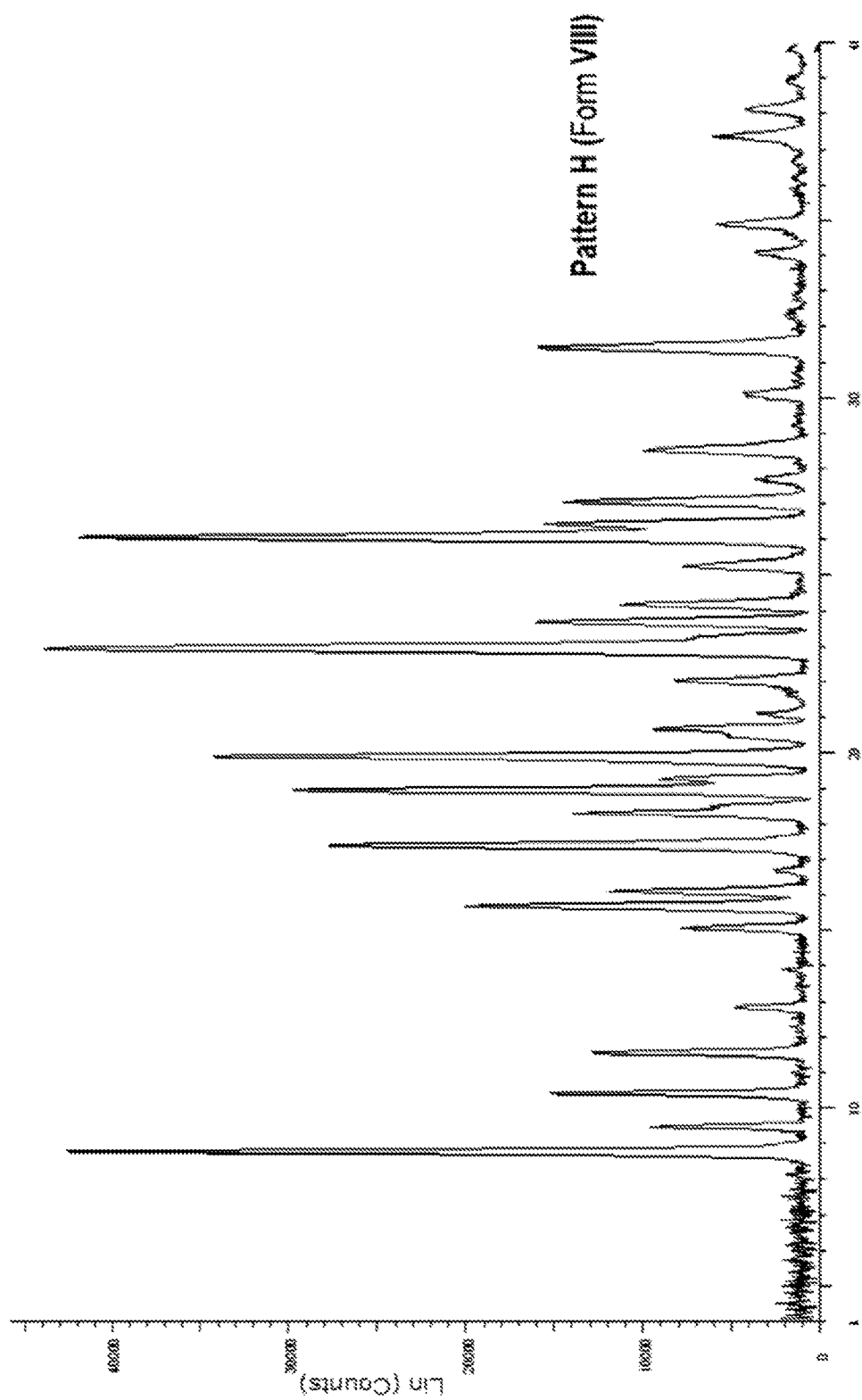
FIG. 47 shows the XRPD pattern of Pattern H, Form VIII.

In an embodiment, Form VIII is characterized by an X-ray powder diffraction pattern that is substantially the same as that of FIG. 47.

9. Form IX

Figure 32:
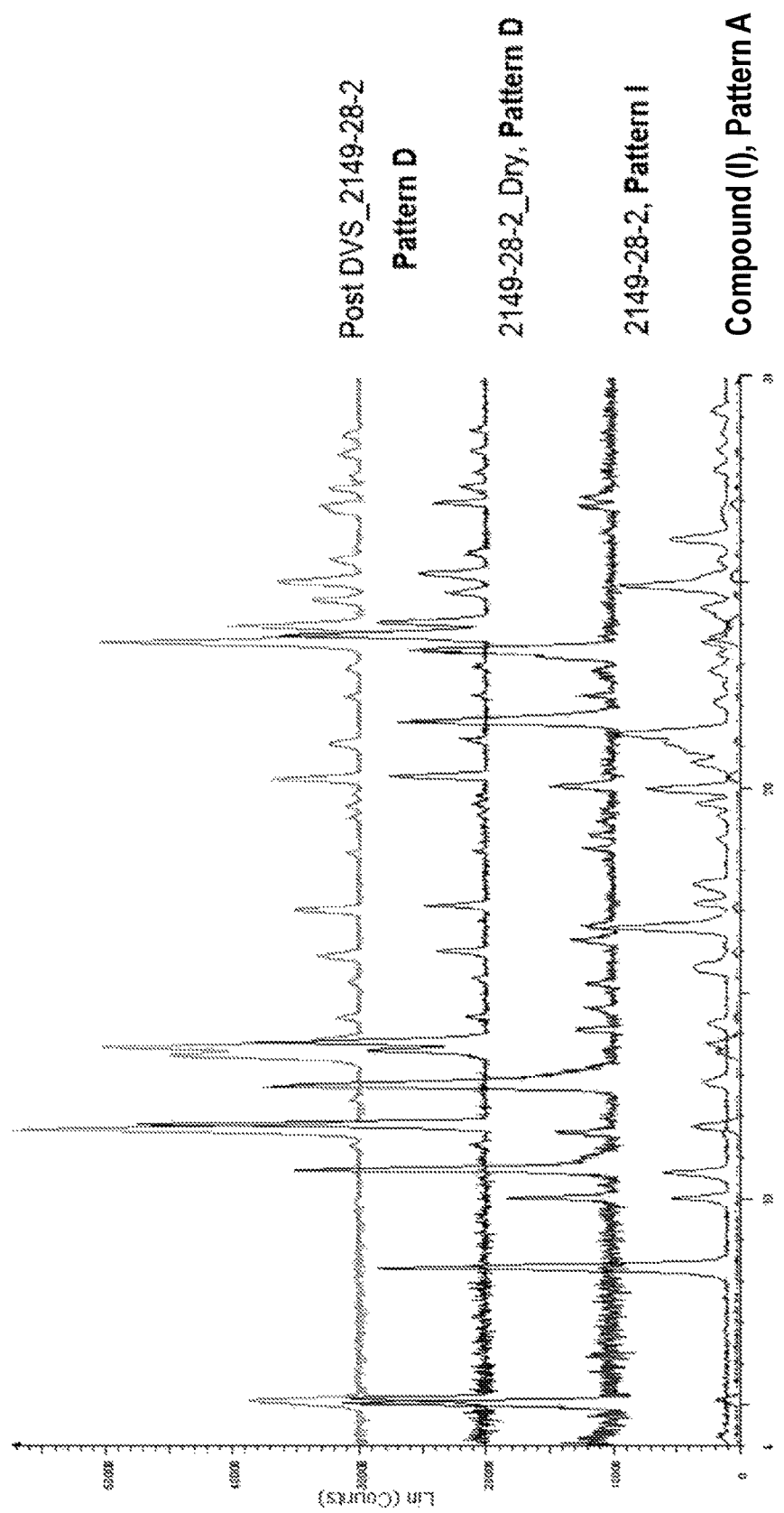
FIG. 32 shows a comparison of XRPD patterns of Form IX (Pattern I), dry and post DVS with Form I, Pattern A.

In one aspect, provided herein is 2-((2-chlorophenyl)(phenyl)amino)-N-(7-(hydroxyamino)-7-oxoheptyl)pyrimidine-5-carboxamide of Form IX (referred to herein as "Form IX"). Form IX was identified by an anti-solvent experiment utilizing EtOH: $H_2O$ (95:5)/MeCN. The scale-up and characterization of Form IX is described in Example 7. It was found that after drying the material under vacuum at 45° C. resulted in a phase transformation to Pattern D (Form IV). The XRPD analysis of this transformation is shown in FIG. 32. Independent XRPD analysis of Form IX, Pattern I, including peak identification, is found in Example 19 (see FIG. 48).

In an embodiment, Form IX is characterized by an X-ray powder diffraction pattern having peaks expressed in degrees 2-Theta at angles 5.0±0.2°, 10.7±0.2°, 11.6±0.2°, and 23.4±0.2°.

In an embodiment, Form IX is characterized by an X-ray powder diffraction pattern having peaks expressed in degrees 2-Theta at angles 5.02±0.2°, 10.01±0.2°, 10.71±0.2°, 12.75±0.2°, 20.06±0.2°, 21.63±0.2°, and 23.37±0.2°.

In an embodiment, Form IX is characterized by an X-ray powder diffraction pattern having peaks expressed in degrees 2-Theta at angles 5.02±0.2°, 10.01±0.2°, 10.71±0.2°, 11.61±0.2°, 12.75±0.2°, 14.12±0.2°, 15.24±0.2°, 16.29±0.2°, 16.63±0.2°, 20.06±0.2°, 21.63±0.2°, 22.85±0.2°, 23.37±0.2°, 26.87±0.2°, 27.09±0.2°, 27.73±0.2°.

Figure 48:
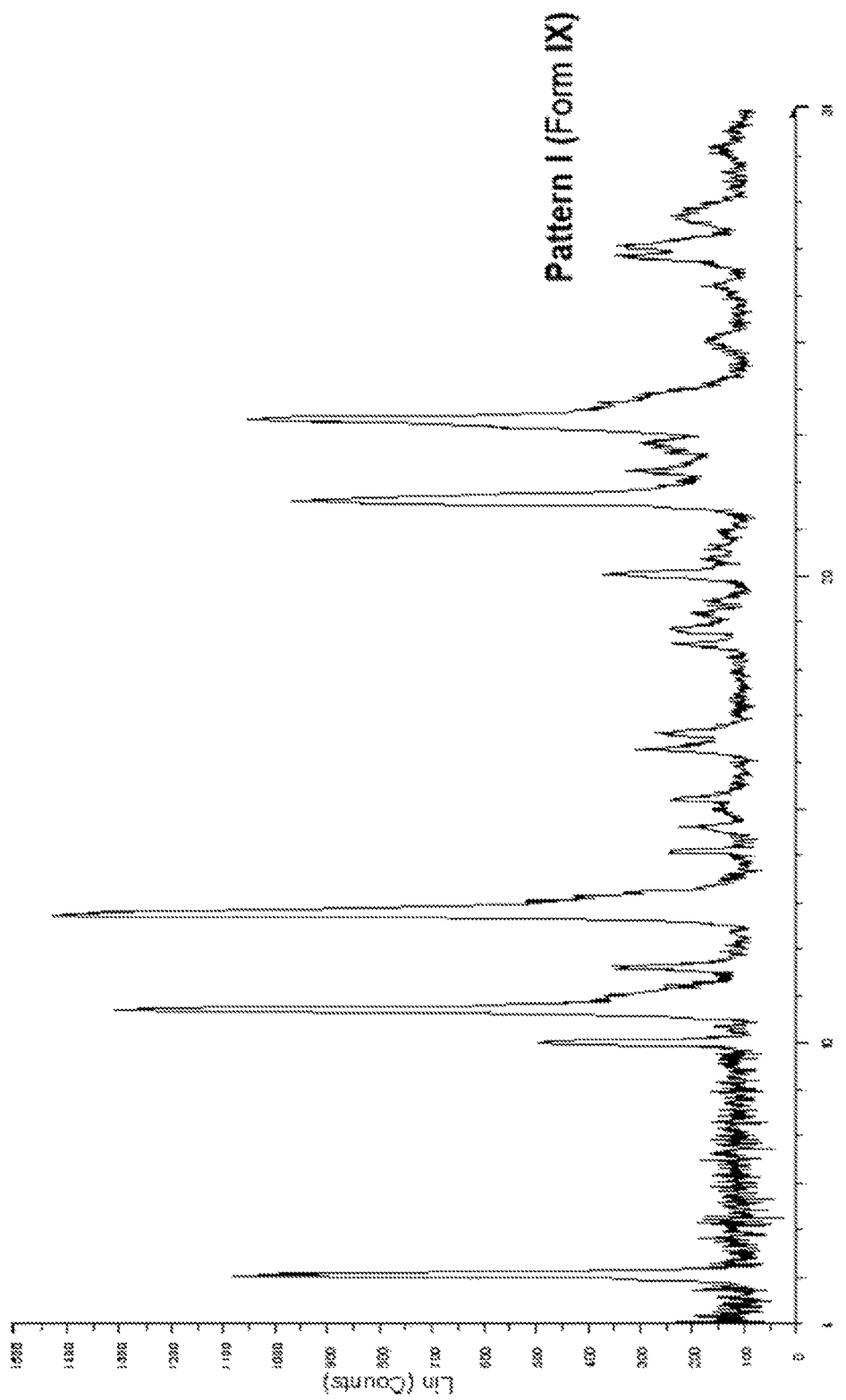
FIG. 48 shows the XRPD pattern of Pattern I, Form IX.

In an embodiment, Form IX is characterized by an X-ray powder diffraction pattern that is substantially the same as that of FIG. 48.

Processes and Methods

Provided herein are methods of making crystalline forms of 2-((2-chlorophenyl)(phenyl)amino)-N-(7-(hydroxyamino)-7-oxoheptyl)pyrimidine-5-carboxamide.

As described above, there are several methods described herein that will result in the crystalline form of 2-((2-chlorophenyl)(phenyl)amino)-N-(7-(hydroxyamino)-7-oxoheptyl)pyrimidine-5-carboxamide. These methods include slurry experiment, slow evaporation, drying, fast cooling crystallization experiments, anti-solvent addition, and vapor diffusion.

Provided herein is a process for preparing Form I of 2-((2-chlorophenyl)(phenyl)amino)-N-(7-(hydroxyamino)-7-oxoheptyl)pyrimidine-5-carboxamide from a composition comprising Form IV/Pattern D. This process is described in Example 1.

Thus, in an aspect, provided herein is a process for preparing Form I of 2-((2-chlorophenyl)(phenyl)amino)-N-(7-(hydroxyamino)-7-oxoheptyl)pyrimidine-5-carboxamide comprising:

(a) suspending a composition comprising 2-((2-chlorophenyl)(phenyl)amino)-N-(7-(hydroxyamino)-7-oxoheptyl)pyrimidine-5-carboxamide in a solvent to form a slurry;

(b) heating the slurry until the solids are dissolved;

(c) seeding the solution formed in step (b) with crystals of Form I of 2-((2-chlorophenyl)(phenyl)amino)-N-(7-(hydroxyamino)-7-oxoheptyl)pyrimidine-5-carboxamide;

(d) cooling the solution until a precipitate forms; and (e) filtering the precipitate such that Form I is acquired.

In an embodiment, the solvent of step (a) is ethanol, acetone, isopropyl alcohol, dichloromethane (DCM), acetonitrile (ACN), HEP, $H_2O$, ethyl acetate, THF, TBME, or any combination thereof. In a further embodiment, the solvent is isopropyl alcohol, ethanol, acetone, acetone:$H_2O$, or ethanol:$H_2O$. In yet a further embodiment, the solvent is isopropyl alcohol.

In an embodiment, the composition of step (a) comprises 2-((2-chlorophenyl)(phenyl)amino)-N-(7-(hydroxyamino)-7-oxoheptyl)pyrimidine-5-carboxamide of Form IV.

In an embodiment, the composition of step (a) comprises 2-((2-chlorophenyl)(phenyl)amino)-N-(7-(hydroxyamino)-7-oxoheptyl)pyrimidine-5-carboxamide of Form IV and the solvent of step (a) is isopropyl alcohol.

In an embodiment, Form I is characterized by an X-ray powder diffraction pattern having peaks expressed in degrees-2-theta at angles 8.3±0.2°, 10.6±0.2°, 16.6±0.2°, 21.3±0.2°, and 25.0±0.2°.

In a further embodiment, Form I of 2-((2-chlorophenyl)(phenyl)amino)-N-(7-(hydroxyamino)-7-oxoheptyl)pyrimidine-5-carboxamide prepared by the processes provided herein is substantially free of other crystalline forms of 2-((2-chlorophenyl)(phenyl)amino)-N-(7-(hydroxyamino)-7-oxoheptyl)pyrimidine-5-carboxamide.

In another embodiment, the 2-((2-chlorophenyl)(phenyl)amino)-N-(7-(hydroxyamino)-7-oxoheptyl)pyrimidine-5-carboxamide is greater than 90% pure. In a further embodiment, the 2-((2-chlorophenyl)(phenyl)amino)-N-(7-(hydroxyamino)-7-oxoheptyl)pyrimidine-5-carboxamide is greater than 95% pure. In yet a further embodiment, the 2-((2-chlorophenyl)(phenyl)amino)-N-(7-(hydroxyamino)-

7-oxoheptyl)pyrimidine-5-carboxamide is greater than 99% pure. The purity of 2-((2-chlorophenyl)(phenyl)amino)-N-(7-(hydroxyamino)-7-oxoheptyl)pyrimidine-5-carboxamide can be determined by HPLC, such as the method described in Example 1.

Also provided herein are compositions or formulations comprising one or more crystalline forms of 2-((2-chlorophenyl)(phenyl)amino)-N-(7-(hydroxyamino)-7-oxoheptyl)pyrimidine-5-carboxamide. The compositions provided herein can contain one or more of the crystalline forms of 2-((2-chlorophenyl)(phenyl)amino)-N-(7-(hydroxyamino)-7-oxoheptyl)pyrimidine-5-carboxamide described herein (i.e., Forms I, II, II, IV, V, VI, VII, VIII, and/or IX).

In certain embodiments, the compositions will comprise a crystalline form of 2-((2-chlorophenyl)(phenyl)amino)-N-(7-(hydroxyamino)-7-oxoheptyl)pyrimidine-5-carboxamide that is substantially free from other crystalline forms. Thus, provided herein is a composition comprising Form I of 2-((2-chlorophenyl)(phenyl)amino)-N-(7-(hydroxyamino)-7-oxoheptyl)pyrimidine-5-carboxamide, wherein Form I is substantially free of other crystalline forms of 2-((2-chlorophenyl)(phenyl)amino)-N-(7-(hydroxyamino)-7-oxoheptyl)pyrimidine-5-carboxamide (e.g., substantially free of forms II, III, IV, V, VI, VII, VIII, and/or IX).

Pharmaceutical Compositions

Provided herein are pharmaceutical compositions or formulations comprising one or more crystalline forms of 2-((2-chlorophenyl)(phenyl)amino)-N-(7-(hydroxyamino)-7-oxoheptyl)pyrimidine-5-carboxamide. The pharmaceutical compositions provided herein can contain one or more of the crystalline forms of 2-((2-chlorophenyl)(phenyl)amino)-N-(7-(hydroxyamino)-7-oxoheptyl)pyrimidine-5-carboxamide described herein (i.e., Forms I, II, II, IV, V, VI, VII, VIII, and/or IX).

In certain embodiments, the pharmaceutical compositions will comprise a crystalline form of 2-((2-chlorophenyl)(phenyl)amino)-N-(7-(hydroxyamino)-7-oxoheptyl)pyrimidine-5-carboxamide that is substantially free from other crystalline forms. Thus, provided herein is a pharmaceutical composition comprising Form I of 2-((2-chlorophenyl)(phenyl)amino)-N-(7-(hydroxyamino)-7-oxoheptyl)pyrimidine-5-carboxamide and pharmaceutically acceptable carrier, wherein Form I is substantially free of other crystalline forms of 2-((2-chlorophenyl)(phenyl)amino)-N-(7-(hydroxyamino)-7-oxoheptyl)pyrimidine-5-carboxamide (e.g., substantially free of forms II, III, IV, V, VI, VII, VIII, and/or IX).

In an aspect, provided herein is a pharmaceutical composition comprising 2-((2-chlorophenyl)(phenyl)amino)-N-(7-(hydroxyamino)-7-oxoheptyl)pyrimidine-5-carboxamide of Form I and a pharmaceutically acceptable carrier, wherein Form I is characterized by an X-ray powder diffraction pattern having peaks expressed in degrees-2-theta at angles 8.3±0.2°, 10.6±0.2°, 16.6±0.2°, 21.3±0.2°, and 25.0±0.2°. In an embodiment, the 2-((2-chlorophenyl)(phenyl)amino)-N-(7-(hydroxyamino)-7-oxoheptyl)pyrimidine-5-carboxamide is substantially free of crystalline forms other than Form I. In another embodiment the 2-((2-chlorophenyl)(phenyl)amino)-N-(7-(hydroxyamino)-7-oxoheptyl)pyrimidine-5-carboxamide is greater than 90% pure. In yet another embodiment, the 2-((2-chlorophenyl)(phenyl)amino)-N-(7-(hydroxyamino)-7-oxoheptyl)pyrimidine-5-carboxamide is greater than 95% pure. In another embodiment, the 2-((2-chlorophenyl)(phenyl)amino)-N-(7-(hydroxyamino)-7-oxoheptyl)pyrimidine-5-carboxamide is greater than 99% pure. The purity of 2-((2-chlorophenyl)(phenyl)amino)-N-(7-(hydroxyamino)-7-oxoheptyl)pyrimidine-5-carboxamide can be determined by HPLC, such as the method described in Example 1.

The pharmaceutical compositions can be formulated for oral, intravenous, intramuscular, subcutaneous or parenteral administration for the therapeutic or prophylactic treatment of diseases, such as cancer.

The pharmaceutical preparations disclosed herein may be prepared in accordance with standard procedures and are administered at dosages that are selected to reduce, prevent or eliminate disease (see, e.g., Remington's Pharmaceutical Sciences, Mack Publishing Company, Easton, Pa. and Goodman and Gilman's "The Pharmaceutical Basis of Therapeutics," Pergamon Press, New York, N.Y., the contents of which are incorporated herein by reference, for a general description of the methods for administering various antimicrobial agents for human therapy).

The pharmaceutical compositions can comprise one or more of the crystalline forms disclosed herein in association with one or more nontoxic, pharmaceutically-acceptable carriers and/or diluents and/or adjuvants and/or excipients. In a preferred embodiment, the pharmaceutical composition comprises Form I. As used herein, the phrase "pharmaceutically-acceptable carrier" refers to any and all solvents, dispersion media, coatings, antibacterial and antifungal agents, isotonic and absorption delaying agents, and the like, that are compatible with pharmaceutical administration. The use of such media and agents for pharmaceutically active substances is well known in the art.

For oral or parenteral administration, the crystalline forms disclosed herein can be mixed with conventional pharmaceutical carriers and excipients and used in the form of tablets, capsules, elixirs, suspensions, syrups, wafers and the like. The compositions comprising a compound of this invention may contain from about 0.1% to about 99% by weight of the active compound, such as from about 10% to about 30%.

For oral use, solid formulations such as tablets and capsules are useful. Sustained release or enterically coated preparations may also be devised. For pediatric and geriatric applications, one embodiment provides suspensions, syrups and chewable tablets. For oral administration, the pharmaceutical compositions are in the form of, for example, a tablet, capsule, suspension or liquid.

The pharmaceutical compositions may be made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, fillers, lubricants, disintegrants, or acceptable wetting agents. Oral liquid preparations generally are in the form of aqueous or oily solutions, suspensions, emulsions, syrups or elixirs.

The pharmaceutical compositions disclosed herein can be placed in a pharmaceutically acceptable carrier and are delivered to a recipient subject (e.g., a human) in accordance with known methods of drug delivery. In general, the methods of delivering the pharmaceutical compositions in vivo utilize art-recognized protocols for delivering the agent with the only substantial procedural modification being the substitution of the compounds of the present invention for the drugs in the art-recognized protocols.

As used herein, the phrases "therapeutically-effective dose" and "therapeutically-effective amount" refer to an amount of a compound that prevents the onset, alleviates the symptoms, stops the progression of disease, or results in another desired biological outcome such as, e.g., improved clinical signs or reduced/elevated levels of lymphocytes and/or antibodies.

The term "treating" or "treatment" is defined as administering, to a subject, a therapeutically-effective amount of Compound (I) in any of the forms presented herein to control or eliminate a disease. Those in need of treatment may include individuals already having a particular medical disease as well as those at risk for the disease (i.e., those who are likely to ultimately acquire the disorder).

The term "subject," as used herein, refers to a mammal, a plant, a lower animal, or a cell culture. In one embodiment, a subject is a human or other animal patient in need of treatment.

The term "administering" or "administration" and the like, refers to providing the Compound (I) to the subject in need of treatment. Preferably the subject is a mammal, more preferably a human.

Methods of Treatment

Provided herein are methods for the treatment of a disease comprising administering one or more crystalline forms of 2-((2-chlorophenyl)(phenyl)amino)-N-(7-(hydroxyamino)-7-oxoheptyl)pyrimidine-5-carboxamide, or a pharmaceutical composition comprising one or more crystalline forms of 2-((2-chlorophenyl)(phenyl)amino)-N-(7-(hydroxyamino)-7-oxoheptyl)pyrimidine-5-carboxamide.

In one aspect, provided herein are methods for the treatment of cancer comprising administering one or more crystalline forms of 2-((2-chlorophenyl)(phenyl)amino)-N-(7-(hydroxyamino)-7-oxoheptyl)pyrimidine-5-carboxamide or a pharmaceutical composition comprising one or more crystalline forms of 2-((2-chlorophenyl)(phenyl)amino)-N-(7-(hydroxyamino)-7-oxoheptyl)pyrimidine-5-carboxamide. In an embodiment, the cancer is a hematological cancer such as, e.g., a leukemia, lymphoma, or myeloma. In an embodiment, the cancer is multiple myeloma. In another embodiment, the cancer is a lymphoma such as mantle cell lymphoma (MCL) or Non-Hidgkin's lymphoma (NHL). In another embodiment, the cancer is leukemia, such as acute myelogenous leukemia (AML).

In yet another embodiment, the cancer is a solid tumor. In a further embodiment, the cancer is selected from the group consisting of lung cancer, colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, glioblastoma, neuroblastoma, hepatocellular carcinoma, papillary renal carcinoma, head and neck squamous cell carcinoma, retinoblastoma, cervical cancer, melanoma and/or skin cancer, bladder cancer, uterine cancer, testicular cancer, and esophageal cancer. In some embodiments, the cancer is lung cancer, colon cancer, breast cancer, or neuroblastoma. In a further embodiment, the cancer is non-small cell lung cancer (NSCLC) or small cell lung cancer.

In another aspect, provided herein is a method for treating cancer comprising administering a crystalline form of 2-((2-chlorophenyl)(phenyl)amino)-N-(7-(hydroxyamino)-7-oxoheptyl)pyrimidine-5-carboxamide or a pharmaceutical composition comprising a crystalline form of 2-((2-chlorophenyl)(phenyl)amino)-N-(7-(hydroxyamino)-7-oxoheptyl)pyrimidine-5-carboxamide, wherein the crystalline form is characterized by an X-ray powder diffraction pattern having peaks expressed in degrees-2-theta at angles 8.3±0.2°, 10.6±0.2°, 16.6±0.2°, 21.3±0.2°, and 25.0±0.2° (e.g., Compound (I), Form I).

In yet another aspect, provided herein is a method of treating multiple myeloma comprising administering a crystalline form of 2-((2-chlorophenyl)(phenyl)amino)-N-(7-(hydroxyamino)-7-oxoheptyl)pyrimidine-5-carboxamide or a pharmaceutical composition comprising a crystalline form of 2-((2-chlorophenyl)(phenyl)amino)-N-(7-(hydroxyamino)-7-oxoheptyl)pyrimidine-5-carboxamide, wherein the crystalline form is characterized by an X-ray powder diffraction pattern having peaks expressed in degrees-2-theta at angles 8.3±0.2°, 10.6±0.2°, 16.6±0.2°, 21.3±0.2°, and 25.0±0.2° (e.g., Compound (I), Form I).

In yet another aspect, provided herein is a method of treating a solid tumor comprising administering a crystalline form of 2-((2-chlorophenyl)(phenyl)amino)-N-(7-(hydroxyamino)-7-oxoheptyl)pyrimidine-5-carboxamide or a pharmaceutical composition comprising a crystalline form of 2-((2-chlorophenyl)(phenyl)amino)-N-(7-(hydroxyamino)-7-oxoheptyl)pyrimidine-5-carboxamide, wherein the crystalline form is characterized by an X-ray powder diffraction pattern having peaks expressed in degrees-2-theta at angles 8.3±0.2°, 10.6±0.2°, 16.6±0.2°, 21.3±0.2°, and 25.0±0.2° (e.g., Compound (I), Form I).

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The following examples further illustrate aspects of the present invention. However, they are in no way a limitation of the teachings or disclosure of the present invention as set forth herein.

EXAMPLES

Example 1

Synthesis of 2-((2-chlorophenyl)(phenyl)amino)-N-(7-(hydroxyamino)-7-oxoheptyl)pyrimidine-5-carboxamide (Compound (I))

I. Synthesis of 2-(diphenylamino)-N-(7-(hydroxyamino)-7-oxoheptyl)pyrimidine-5-carboxamide

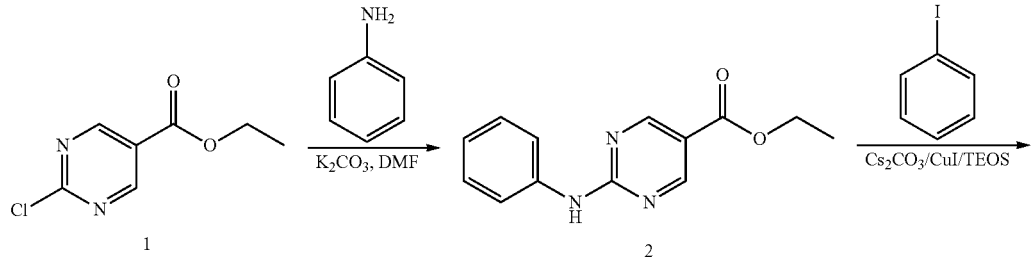

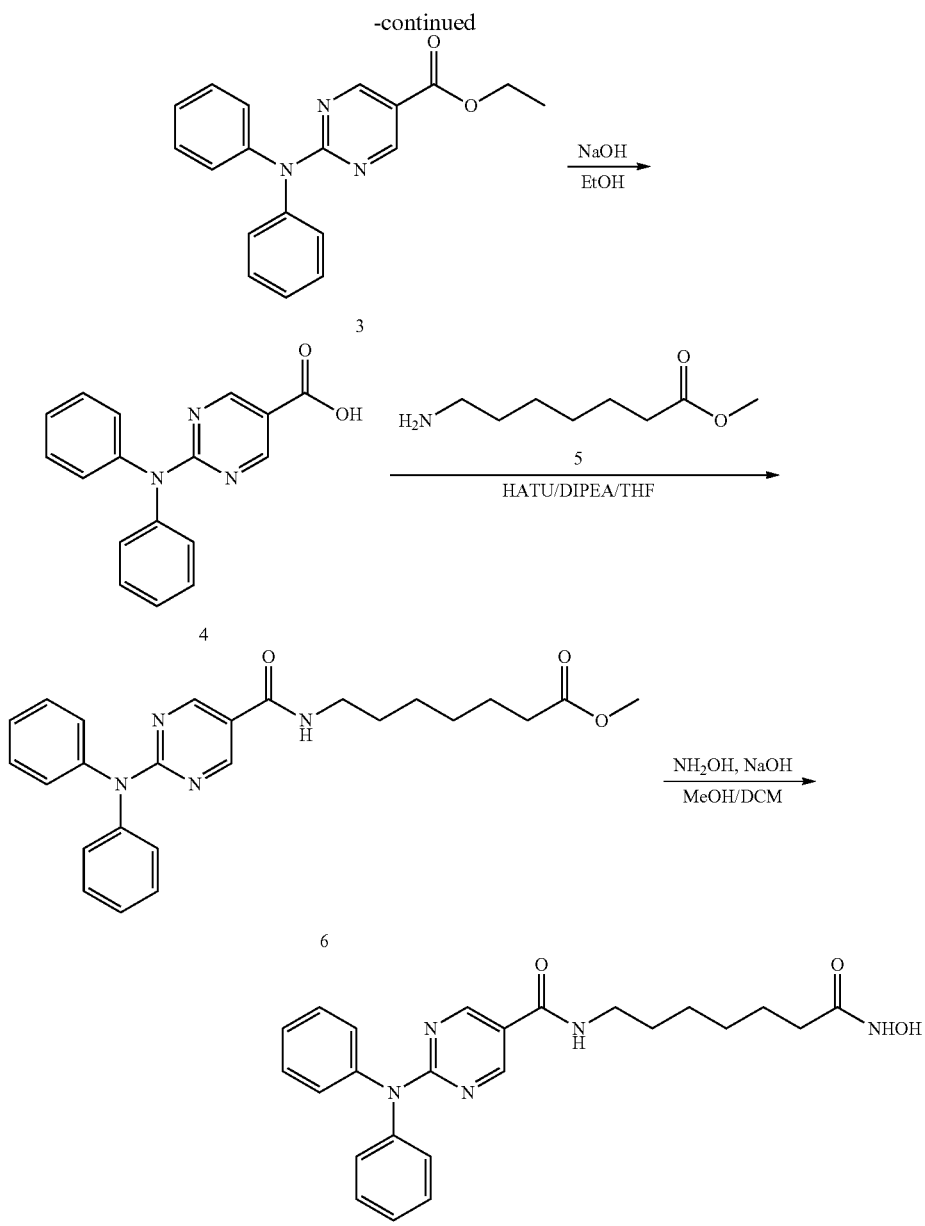

Synthesis of Intermediate 2: A mixture of aniline (3.7 g, 40 mmol), compound 1 (7.5 g, 40 mmol), and K₂CO₃ (11 g, 80 mmol) in DMF (100 ml) was degassed and stirred at 120° C. under N₂ overnight. The reaction mixture was cooled to r.t. and diluted with EtOAc (200 ml), then washed with saturated brine (200 ml×3). The organic layers were separated and dried over Na₂SO₄, evaporated to dryness and purified by silica gel chromatography (petroleum ethers/EtOAc=10/1) to give the desired product as a white solid (6.2 g, 64%).

Synthesis of Intermediate 3: A mixture of compound 2 (6.2 g, 25 mmol), iodobenzene (6.12 g, 30 mmol), CuI (955 mg, 5.0 mmol), Cs₂CO₃ (16.3 g, 50 mmol) in TEOS (200 ml) was degassed and purged with nitrogen. The resulting mixture was stirred at 140° C. for 14 hrs. After cooling to r.t., the residue was diluted with EtOAc (200 ml). 95% EtOH (200 ml) and NH₄F—H₂O on silica gel [50 g, pre-prepared by the addition of NH₄F (100 g) in water (1500 ml) to silica gel (500 g, 100-200 mesh)] was added, and the resulting mixture was kept at r.t. for 2 hrs. The solidified materials were filtered and washed with EtOAc. The filtrate was evaporated to dryness and the residue was purified by silica gel chromatography (petroleum ethers/EtOAc=10/1) to give a yellow solid (3 g, 38%).

Synthesis of Intermediate 4: 2N NaOH (200 ml) was added to a solution of compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layers were separated, washed with water (2×100 ml), brine (2×100 ml), and dried over Na₂SO₄. Removal of the solvent gave a brown solid (2.5 g, 92%).

Synthesis of Intermediate 6: A mixture of compound 4 (2.5 g, 8.58 mmol), compound 5 (2.52 g, 12.87 mmol), HATU (3.91 g, 10.30 mmol), and DIPEA (4.43 g, 34.32 mmol) was stirred at r.t. overnight. After the reaction mixture was filtered, the filtrate was evaporated to dryness and the residue was purified by silica gel chromatography (petroleum ethers/EtOAc=2/1) to give a brown solid (2 g, 54%).

Synthesis of 2-(diphenylamino)-N-(7-(hydroxyamino)-7-oxoheptyl)pyrimidine-5-carboxamide: A mixture of the compound 6 (2.0 g, 4.6 mmol), sodium hydroxide (2N, 20 mL) in MeOH (50 ml) and DCM (25 ml) was stirred at 0° C. for 10 min. Hydroxylamine (50%) (10 ml) was cooled to 0° C. and added to the mixture. The resulting mixture was stirred at r.t. for 20 min. After removal of the solvent, the mixture was neutralized with 1M HCl to give a white precipitate. The crude product was filtered and purified by pre-HPLC to give a white solid (950 mg, 48%).

II. Synthetic Route 1: 2-((2-chlorophenyl)(phenyl)amino)-N-(7-(hydroxyamino)-7-oxoheptyl)pyrimidine-5-carboxamide

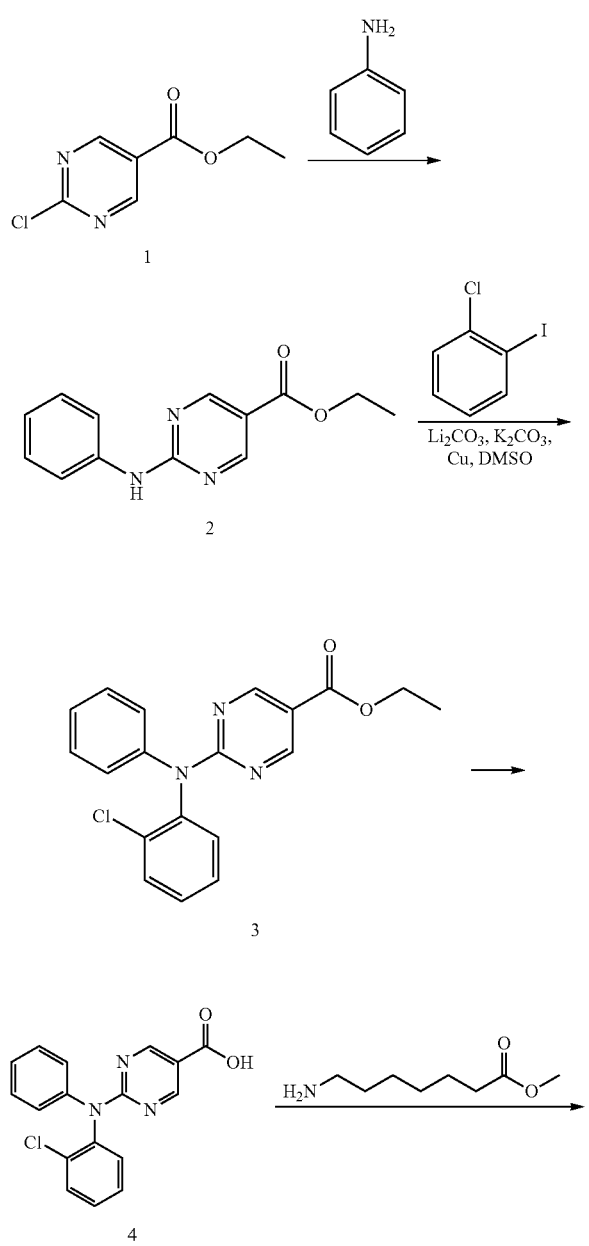

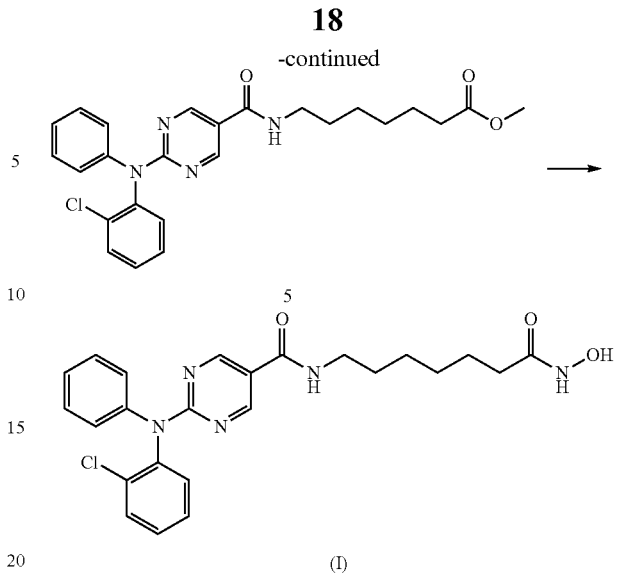

Synthesis of Intermediate 2: A mixture of aniline (3.7 g, 40 mmol), ethyl 2-chloropyrimidine-5-carboxylate 1 (7.5 g, 40 mmol), $K_2CO_3$ (11 g, 80 mmol) in DMF (100 ml) was degassed and stirred at 120° C. under $N_2$ overnight. The reaction mixture was cooled to rt and diluted with EtOAc (200 ml), then washed with saturated brine (200 ml×3). The organic layer was separated and dried over $Na_2SO_4$, evaporated to dryness and purified by silica gel chromatography (petroleum ethers/EtOAc=10/1) to give the desired product as a white solid (6.2 g, 64%).

Synthesis of Intermediate 3: A mixture of compound 2 (69.2 g, 1 equiv.), 1-chloro-2-iodobenzene (135.7 g, 2 equiv.), $Li_2CO_3$ (42.04 g, 2 equiv.), $K_2CO_3$ (39.32 g, 1 equiv.), Cu (1 equiv. 45 µm) in DMSO (690 ml) was degassed and purged with nitrogen. The resulting mixture was stirred at 140° C. for 36 hours. Work-up of the reaction gave compound 3 at 93% yield.

Synthesis of Intermediate 4: 2N NaOH (200 ml) was added to a solution of the compound 3 (3.0 g, 9.4 mmol) in EtOH (200 ml). The mixture was stirred at 60° C. for 30 min. After evaporation of the solvent, the solution was neutralized with 2N HCl to give a white precipitate. The suspension was extracted with EtOAc (2×200 ml), and the organic layer was separated, washed with water (2×100 ml), brine (2×100 ml), and dried over $Na_2SO_4$. Removal of solvent gave a brown solid (2.5 g, 92%).

Synthesis of Intermediate 5: A procedure analogous to the Synthesis of Intermediate 6 in Part I of this Example was used.

Synthesis of 2-((2-chlorophenyl)(phenyl)amino)-N-(7-(hydroxyamino)-7-oxoheptyl)pyrimidine-5-carboxamide: A procedure analogous to the Synthesis of 2-(diphenylamino)-N-(7-(hydroxyamino)-7-oxoheptyl)pyrimidine-5-carboxamide in Part I of this Example was used.

III. Synthetic Route 2: 2-((2-chlorophenyl)(phenyl)amino)-N-(7-(hydroxyamino)-7-oxoheptyl)pyrimidine-5-carboxamide

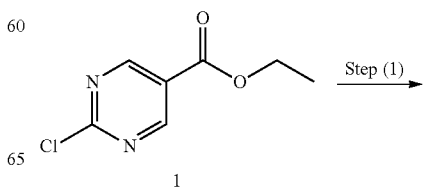

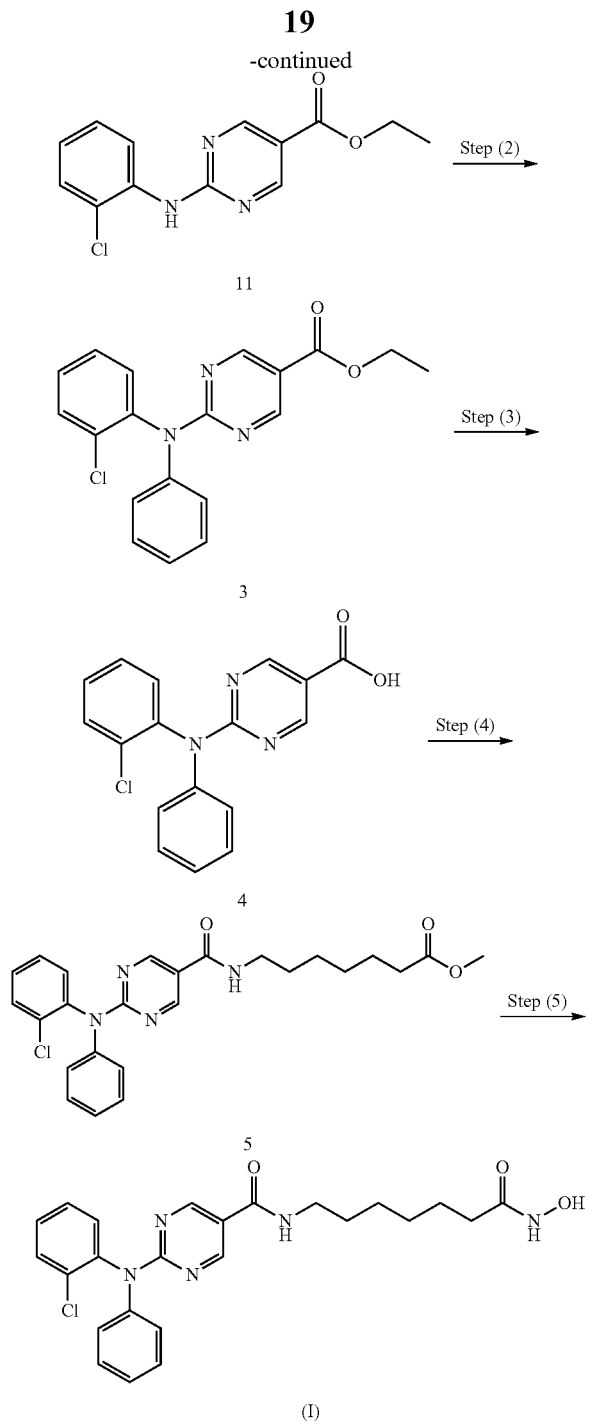

Step (1): Synthesis of Compound 11: Ethyl 2-chloropyrimidine-5-carboxylate (7.0 Kgs), ethanol (60 Kgs), 2-Chloroaniline (9.5 Kgs, 2 eq) and acetic acid (3.7 Kgs, 1.6 eq) were charged to a reactor under inert atmosphere. The mixture was heated to reflux. After at least 5 hours the reaction was sampled for HPLC analysis (method TM-113.1016). When analysis indicated reaction completion, the mixture was cooled to 70±5° C. and N,N-Diisopropylethylamine (DIPEA) was added. The reaction was then cooled to 20±5° C. and the mixture was stirred for an additional 2-6 hours. The resulting precipitate is filtered and washed with ethanol (2×6 Kgs) and heptane (24 Kgs). The cake is dried under reduced pressure at 50±5° C. to a constant weight to produce 8.4 Kgs compound 11 (81% yield and 99.9% purity.

Step (2): Synthesis of Compound 3: Copper powder (0.68 Kgs, 1 eq, <75 micron), potassium carbonate (4.3 Kgs, 1.7 eq), and dimethyl sulfoxide (DMSO, 12.3 Kgs) were added to a reactor (vessel A). The resulting solution was heated to 120±5° C. In a separate reactor (vessel B), a solution of compound 11 (2.9 Kgs) and iodobenzene (4.3 Kgs, 2 eq) in DMSO (5.6 Kgs) was heated at 40±5° C. The mixture was then transferred to vessel A over 2-3 hours. The reaction mixture was heated at 120±5° C. for 8-24 hours, until HPLC analysis (method TM-113.942) determined that ≤1% compound 11 was remaining.

Step (3): Synthesis of Compound 4: The mixture of Step (2) was cooled to 90-100° C. and purified water (59 Kgs) was added. The reaction mixture was stirred at 90-100° C. for 2-8 hours until HPLC showed that ≤1% compound 3 was remaining. The reactor was cooled to 25° C. The reaction mixture was filtered through Celite, then a 0.2 micron filter, and the filtrate was collected. The filtrate was extracted with methyl t-butyl ether twice (2×12.8 Kgs). The aqueous layer was cooled to 0-5° C., then acidified with 6N hydrochloric acid (HCl) to pH 2-3 while keeping the temperature <25° C. The reaction was then cooled to 5-15° C. The precipitate was filtered and washed with cold water. The cake was dried at 45-55° C. under reduced pressure to constant weight to obtain 2.2 kg (65% yield) compound 4 in 90.3% AUC purity.

Step (4): Synthesis of Compound 5: Dichloromethane (40.3 Kgs), DMF (33 g, 0.04 eq) and compound 4 (2.3 Kg) were charged to a reaction flask. The solution was filtered through a 0.2 μm filter and was returned to the flask. Oxalyl chloride (0.9 Kgs, 1 eq) was added via addition funnel over 30-120 minutes at <30° C. The batch was then stirred at <30° C. until reaction completion (compound 4≤3%) was confirmed by HPLC (method TM-113.946. Next, the dichloromethane solution was concentrated and residual oxalyl chloride was removed under reduced pressure at <40° C. When HPLC analysis indicated that <0.10% oxalyl chloride was remaining, the concentrate was dissolved in fresh dichloromethane (24 Kgs) and transferred back to the reaction vessel (Vessel A).

A second vessel (Vessel B) was charged with Methyl 7-aminoheptanoate hydrochloride (Compound A1, 1.5 Kgs, 1.09 eq), DIPEA (2.5 Kgs, 2.7 eq), 4 (Dimethylamino) pyridine (DMAP, 42 g, 0.05 eq), and DCM (47.6 Kgs). The mixture was cooled to 0-10° C. and the acid chloride solution in Vessel A was transferred to Vessel B while maintaining the temperature at 5° C. to 10° C. The reaction is stirred at 5-10° C. for 3 to 24 hours at which point HPLC analysis indicated reaction completion (method TM-113.946, compound 4≤5%). The mixture was then extracted with a 1M HCl solution (20 Kgs), purified water (20 Kgs), 7% sodium bicarbonate (20 Kgs), purified water (20 Kgs), and 25% sodium chloride solution (20 Kgs). The dichloromethane was then vacuum distilled at <40° C. and chased repeatedly with isopropyl alcohol. When analysis indicated that <1 mol % DCM was remaining, the mixture was gradually cooled to 0-5° C. and was stirred at 0-5° C. for an at least 2 hours. The resulting precipitate was collected by filtration and washed with cold isopropyl alcohol (6.4 Kgs). The cake was sucked dry on the filter for 4-24 hours, then was further dried at 45-55° C. under reduced pressure to constant weight. 2.2 Kgs (77% yield) was isolated in 95.9% AUC purity method and 99.9 wt %.

Step (5): Synthesis of Compound (I): Hydroxylamine hydrochloride (3.3 Kgs, 10 eq) and methanol (9.6 Kgs) were charged to a reactor. The resulting solution was cooled to 0-5° C. and 25% sodium methoxide (11.2 Kgs, 11 eq) was charged slowly, maintaining the temperature at 0-10° C. Once the addition was complete, the reaction was mixed at 20° C. for 1-3 hours and filtered, and the filter cake was washed with methanol (2×2.1 Kgs). The filtrate (hydroxylamine free base) was returned to the reactor and cooled to 0±5° C. Compound 5 (2.2 Kgs) was added. The reaction was stirred until the reaction was complete (method TM-113.964, compound 5≤2%). The mixture was filtered and water (28 Kgs) and ethyl acetate (8.9 Kgs) were added to the filtrate. The pH was adjusted to 8-9 using 6N HCl then stirred for up to 3 hours before filtering. The filter cake was washed with cold water (25.7 Kgs), then dried under reduced pressure to constant weight. The crude solid compound (I) was determined to be Form IV/Pattern D.

The crude solid (1.87 Kgs) was suspended in isopropyl alcohol (IPA, 27.1 Kg). The slurry was heated to 75±5° C. to dissolve the solids. The solution was seeded with crystals of Compound (I) (Form I/Pattern A), and was allowed to cool to ambient temperature. The resulting precipitate was stirred for 1-2 hours before filtering. The filter cake was rinsed with IPA (2×9.5 Kgs), then dried at 45-55° C. to constant weight under reduced pressure to result in 1.86 kg crystalline white solid Compound (I) (Form I/Pattern A) in 85% yield and 99.5% purity (AUC %, HPLC method TM-113.941).

| HPLC Method 113.941 | |
|---|---|
| Column | Zorbax Eclipse XDB-C18, 4.6 mm × 150 mm, 3.5 μm |
| Column Temperature | 40° C. |
| UV Detection Wavelength | Bandwidth 4 nm, Reference off, 272 nm |
| Flow rate | 1.0 mL/min |
| Injection Volume | 10 μL with needle wash |
| Mobile Phase A | 0.05% trifluoroacetic acid (TFA) in purified water |
| Mobile Phase B | 0.04% TFA in acetonitrile |
| Data Collection | 40.0 min |
| Run Time | 46.0 min |

| | Time (min) | Mobile Phase A | Mobile Phase B |
|---|---|---|---|
| Gradient | 0.0 | 98% | 2% |
| | 36.0 | 0% | 100% |
| | 40.0 | 0% | 100% |
| | 40.1 | 98% | 2% |
| | 46.0 | 98% | 2% |

Example 2

Summary of Results and Analytical Techniques

TABLE 1

Summary of the Isolated Crystalline Forms of Compound (I)

| | Before drying | | | | After drying at 45° C. (under vacuum) | | |
|---|---|---|---|---|---|---|---|
| Form | XRPD pattern | DSC | TGA (Wt loss %) | Post DVS XRPD | XRPD pattern | DSC | TGA (Wt loss %) |
| Form I | Pattern A | Endotherm at 173° C. | <0.2% | Pattern A, Form I | Pattern A, Form I | N/A | N/A |
| Form II | Pattern B | Endotherm at 127° C. Endotherm at 168° C. | 4.54% | Pattern D, Form IV | Pattern D, Form IV | Endotherm at 127° C. Endotherm at 168° C. | 1.07% |
| Form III | Pattern C | Endotherm at 125° C. Endotherm at 167° C. | 5.44% | Pattern D, Form IV | Pattern D, Form IV | Endotherm at 125° C. | 0.78% |
| Form V | Pattern E | Endotherm at 167° C. | 0.5% | Pattern F, Form VI | Pattern F, Form VI | Endotherm at 167° C. | 0.07% |
| Form VII | Pattern G | Endotherm at 120° C. Endotherm at 167° C. | 0.27% | Pattern H, Form VIII | Pattern H, Form VIII | Endotherm at 121° C. | 0.05% |
| Form IX | Pattern I* | Endotherm at 127° C. | 1.7% | Pattern D, Form IV | Pattern D, Form IV | Endotherm at 128° C. | 0.02% |

I. Differential Scanning Calorimetry (DSC)

DSC data were collected using a TA Instruments Q10 DSC. Approximately, samples (2-8 mg) were placed in unsealed but covered hermetic alodined aluminum sample pans and scanned from 30 to 300° C. at a rate of 10° C./min under a nitrogen purge of 50 mL/min.

II. Thermal Gravimetric Analysis (TGA)

TGA data were collected using a TA Instruments TGA Q500. Approximately, 5-10 mg samples were placed in an open, pre-tared aluminum sample pan and scanned from 25 to 300° C. at a rate of 10° C./min using a nitrogen purge at 60 mL/min.

III. X-ray Powder Diffraction (XRPD)

X-ray powder diffraction patterns were obtained using a Bruker D8 Advance equipped with a Cu Kα radiation source (λ=1.54° A), a 9-position sample holder and a LYNXEYE super speed detector. Samples were placed on zero-background, silicon plate holders for analysis.

IV. Dynamic Vapor Sorption (DVS)

Samples were analyzed using an Aquadyne DVS-2 gravimetric water sorption analyzer. The relative humidity was adjusted between 2-95% and the weight of the sample was continuously monitored and recorded with respect to the relative humidity and time.

V. Proton Nuclear Magnetic Resonance ($^1$H-NMR)

Samples were prepared by dissolving the compound in deuterated dimethylsulfoxide with 0.05% (v/v) tetramethylsilane (TMS). Spectra were collected at ambient temperature on a Bruker Avance 300 MHz NMR equipped with TopSpin software. The number of scans was 16 for $^1$H-NMR.

VI. Karl Fischer (KF)

The apparent water content in samples was determined by Karl Fischer titration using a Mettler Toledo DL39 Coulometric KF Titrator. HYDRANAL-Coulomat AD was used as the titrant. About 20 mg of the solid was used for titration. The analytical parameters are presented in Table 2.

TABLE 2

| KF Parameter | Value |
| --- | --- |
| Speed [%] | 40 |
| Mix time [sec] | 10 |
| Auto start | No |
| Blank [µg] | 0 |
| Drift [µg/min] | 5 |
| Calculation | Ug |
| Standby | Yes |
| Initial drift [µg/min] | <10 |
| Initial Potential [mV] | 100 |

VII. Optical Microscopy

Samples were analyzed using an Olympus BX53 polarized light microscope equipped with a PAXcam 3 digital microscope camera.

Example 3

Characterization of Crystalline Forms of Compound (I), Identification of Form I (Pattern A)

I. Characterization

Figure 2:
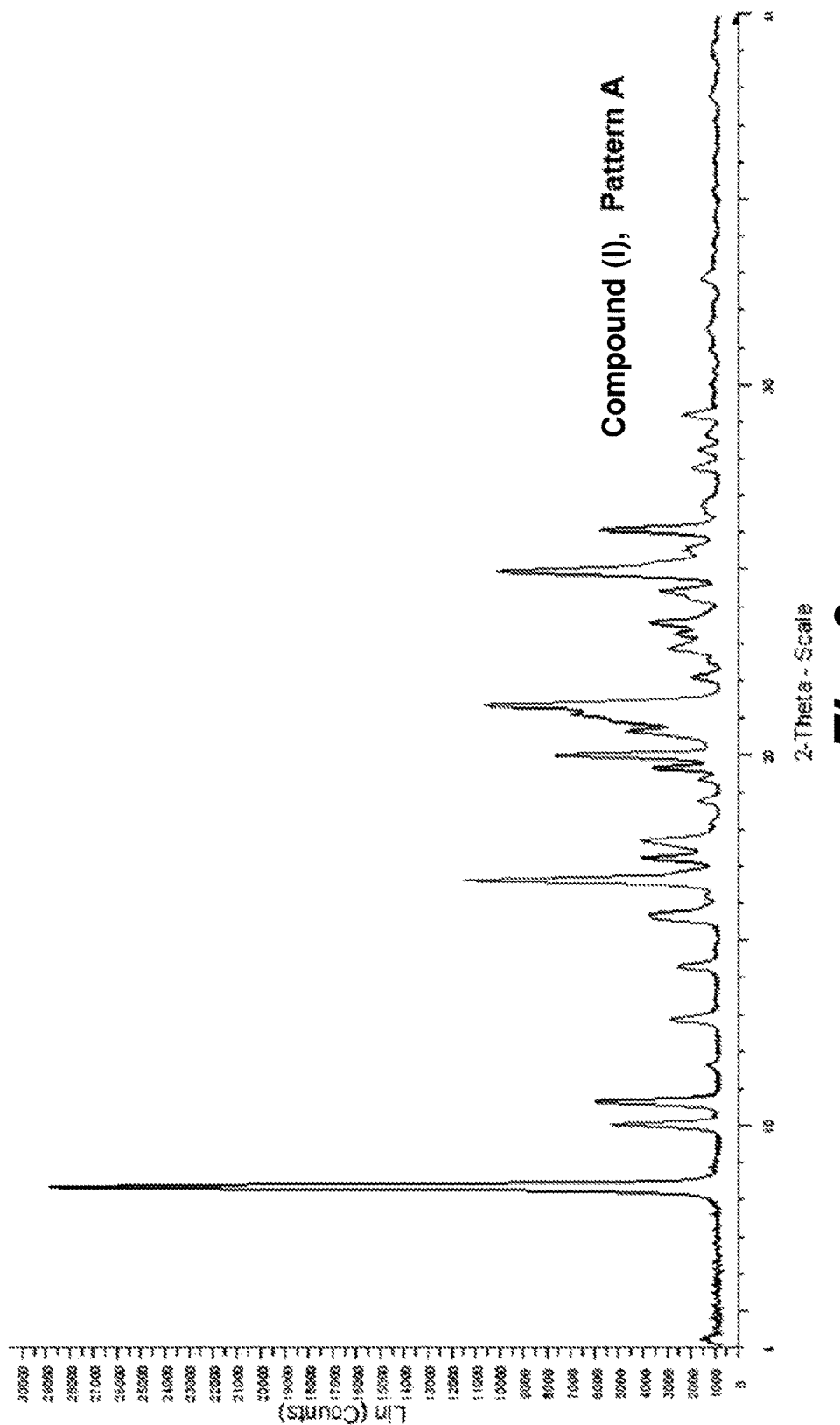
FIG. 2 shows the XRPD pattern of Form I (Pattern A).
Figure 3:
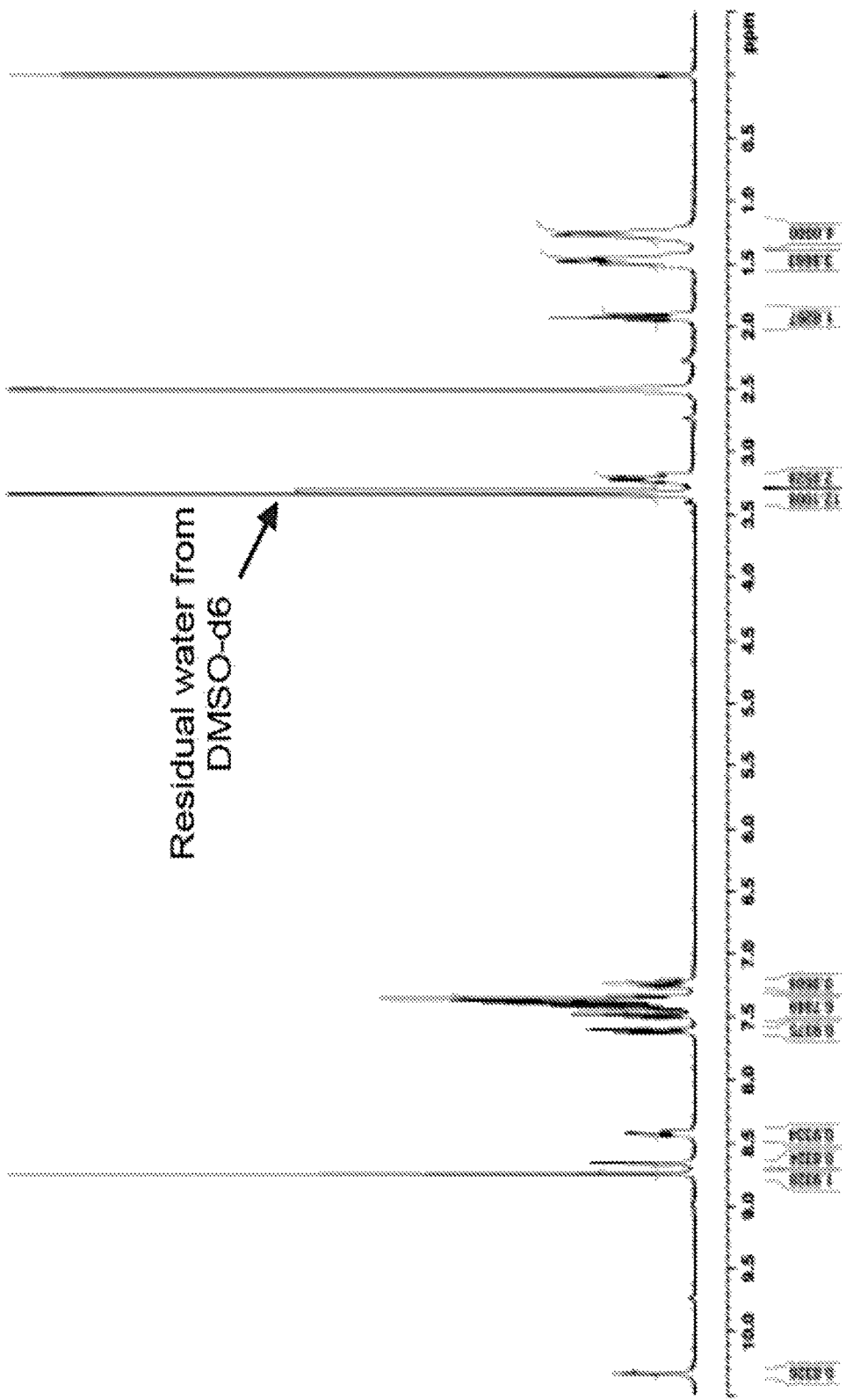
FIG. 3 shows the $^1$H-NMR data of Form I.

The crystalline form of Compound (I) of Form I was characterized using optical microscopy and XRPD (FIG. 2), as well as $^1$H-NMR (FIG. 3). DSC analysis of Form I (characterized by Pattern A, FIG. 2) indicated an endothermic thermal event (melting point) at around 173° C. (FIG. 4), followed by an exothermic event (possible decomposition).

Figure 5:
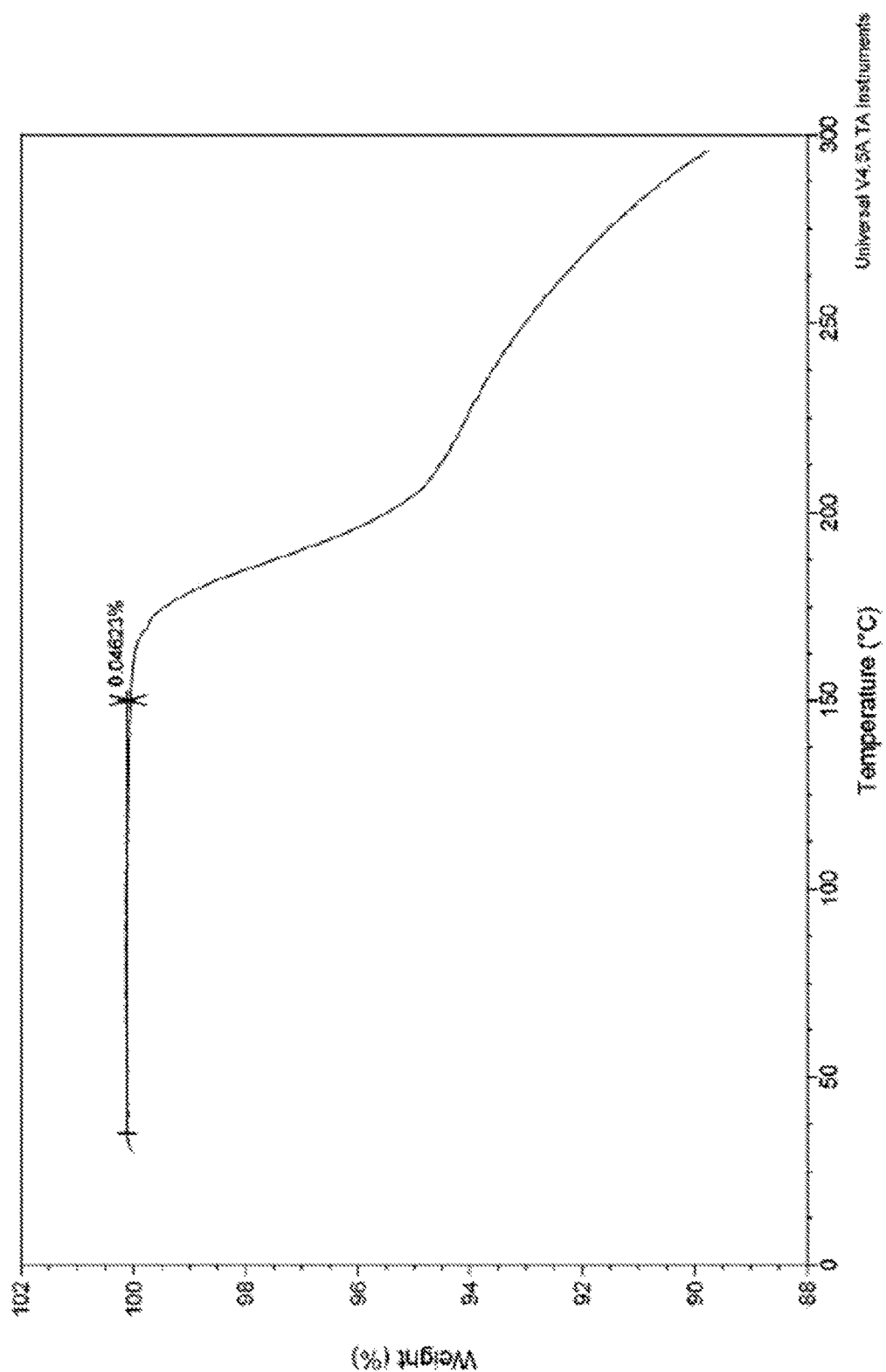
FIG. 5 shows the TGA of Form I.

TGA analysis revealed that there is less than 0.1% weight loss in the sample from 35 to 150° C. as shown in FIG. 5.

Figure 7:
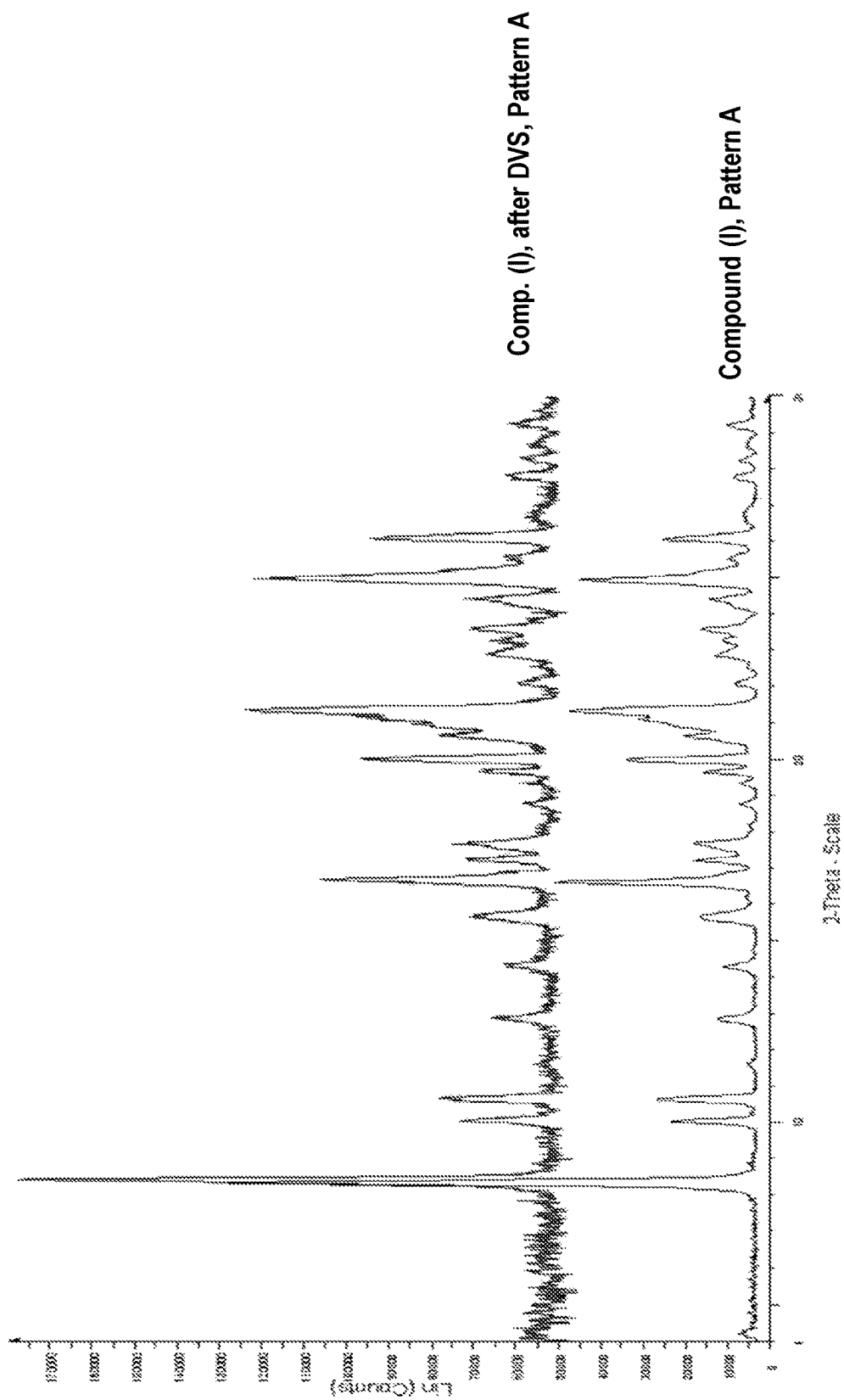
FIG. 7 shows a comparison of XRPD patterns of Form I (Pattern A) before and after DVS.

The material was subjected under Dynamic Vapor Sorption (DVS, FIG. 6). The experimental result revealed that there is less than 0.2% moisture uptake by the material when exposed to relative humidity between 0-95 percent. After DVS, the XRPD indicated no change in the crystalline form of Form I (FIG. 7).

II. Solubility Assessment

The Solubility of Form I was measured gravimetrically in 15 different solvents and solvent mixtures at 15 and 45° C. About 75 mg of the compound was dispensed in 10 volumes (750 µL) of the solvent/solvent mixture and slurried for 48 h.

The vials were centrifuged. The supernatant was collected and left for slow evaporation under vacuum at 45° C. The solids obtained after evaporation were used to determine the solubility of Form I and analyzed by XRPD for any new forms.

TABLE 3

Solubility of Form I in different solvents:
Table 3: Solubility of Compound (I) in different solvent/solvent mixtures. "A" represents at 45° C. and "B" represents at 15° C.

| S. No | Solvent/solvent mixtures | Sample ID | Solubility (mg/mL) |
| --- | --- | --- | --- |
| 1 | Ethanol (EtOH) | 1A | 39 |
|  |  | 1B | 11 |
| 2 | Methanol (MeOH) | 2A | >100 |
|  |  | 2B | 11 |
| 3 | Trifluoro Ethanol (TFE) | 3A | >100 |
|  |  | 3B | >100 |
| 4 | Acetone | 4A | 11 |
|  |  | 4B | 2 |
| 5 | Isopropanol (IPA) | 5A | 12 |
|  |  | 5B | 1 |
| 6 | Dichloromethane (DCM) | 6A | Solid does not |
|  |  | 6B | separate out |
| 7 | Acetonitrile (ACN) | 7A | 1 |
|  |  | 7B | <1 |
| 8 | Heptane (HEP) | 8A | <1 |
|  |  | 8B | <1 |
| 9 | Water (H2O) | 9A | <1 |
|  |  | 9B | <1 |
| 10 | Ethyl acetate (EtOAc) | 10A | 1 |
|  |  | 10B | <1 |
| 11 | Tetrahydrofuran (THF) | 11A | 50 |
|  |  | 11B | 13 |
| 12 | Tert-butyl methyl ether (TBME) | 12A | 2 |
|  |  | 12B | <1 |
| 13 | Dimethylacetamide (DMA) | 13A | >100 |
|  |  | 13B | >100 |
| 14 | Acetone:H$_2$O (95:5) | 14A | 48 |
|  |  | 14B | 21 |
| 15 | EtOH:H$_2$O (95:5) | 15A | 53 |
|  |  | 15B | 18 |

The precipitates for all the above slurry experiments were also analyzed by XRPD and the results are found in Table 4.

TABLE 4

Summary of XRPD analysis of slurry and slow evaporation experiments. "A" represents at 45° C. and "B" represents at 15° C.

| Sample ID | Temperature | Solvent | XRPD from Slurry | XRPD Slow evaporation |
| --- | --- | --- | --- | --- |
| 1A | 45° C. | EtOH | Pattern A | Pattern A |
| 1B | 15° C. |  | Pattern A + peak at 5.2 (2Θ°) | Pattern A |
| 2A | 45° C. | MeOH | N/A* | Pattern B |
| 2B | 15° C. |  | Pattern B | Pattern B |
| 3A | 45° C. | TFE | N/A* | Gel |
| 3B | 15° C. |  | N/A* | Pattern A |
| 4A | 45° C. | Acetone | Pattern A | Pattern A |
| 4B | 15° C. |  | Pattern A | Not enough solid |
| 5A | 45° C. | IPA | Pattern A | Pattern A |
| 5B | 15° C. |  | Pattern A | Pattern A |
| 6A | 45° C. | DCM | Pattern A | N/A** |
| 6B | 15° C. |  | Pattern C | N/A** |
| 7A | 45° C. | ACN | Pattern A | Pattern A |
| 7B | 15° C. |  | Pattern A | Not enough solid |
| 8A | 45° C. | HEP | Pattern A | Not enough solid |

TABLE 4-continued

Summary of XRPD analysis of slurry and slow evaporation experiments. "A" represents at 45° C. and "B" represents at 15° C.

| Sample ID | Temperature | Solvent | XRPD from Slurry | XRPD Slow evaporation |
|---|---|---|---|---|
| 8B | 15° C. | | Pattern A | Not enough solid |
| 9A | 45° C. | H2O | Pattern A | Not enough solid |
| 9B | 15° C. | | | |
| 10A | 45° C. | EtOAc | Pattern A | Not enough solid |
| 10B | 15° C. | | Pattern A | Not enough solid |
| 11A | 45° C. | THF | Pattern A | Pattern A |
| 11B | 15° C. | | Pattern A | Pattern A |
| 12A | 45° C. | TBME | Pattern A | Not enough solid |
| 12B | 15° C. | | Pattern A | Not enough solid |
| 13A | 45° C. | DMA | N/A* | Gel |
| 13B | 15° C. | | N/A* | Pattern A |
| 14A | 45° C. | Acetone:H2O | Pattern A | Pattern A |
| 14B | 15° C. | (95:5) | Pattern A | Pattern A |

TABLE 5

Experimental details of Fast cooling crystallization.

| Sample No. | Solvent (1 mL) | Compound (I) | Result |
|---|---|---|---|
| 1 | EtOH | 39 mg | Pattern A |
| 2 | Acetone | 11 mg | Pattern A |
| 3 | IPA | 12 mg | Pattern A |
| 4 | THF | 45 mg | Pattern E |
| 5 | Acetone:H$_2$O (95:5) | 48 mg | Pattern A |
| 6 | EtOH:H$_2$O (95:5) | 50 mg | Pattern A |

The XRPD analysis of the sample no. 4 resulted in the isolation of a new form of Compound (I) (Form V, Pattern E, FIG. 10), whilst the other samples resulted in the precipitation of Pattern A (i.e., Form I) of Compound (I).

Anti-solvent addition experiments for Compound (I) were performed by using five different anti-solvents. Table 6 summarizes the experimental details and the results.

TABLE 6

Summary of Anti-solvent Experiments

| | | Anti-solvent (1 mL) | | | | |
|---|---|---|---|---|---|---|
| Anti-solvent addition experiments | | EtOAc | Heptane | MeCN | TBME | Water |
| Dissolving solvent for Comp. (I) | 50 mg Comp. (I), TFE (0.5 mL) | Pattern A | Pattern A | Pattern A | Pattern A | Pattern A |
| | 11 mg Comp. (I), Acetone (1 mL) | Pattern A | Pattern A | Pattern A | Pattern A | Pattern A |
| | 12 mg Comp. (I), IPA (1 mL) | Pattern A | Pattern A | Pattern A | Pattern A | Pattern A |
| | 45 mg Comp. (I), THF (1 mL) | Pattern A | Pattern A | Pattern G | Pattern A | Pattern A |
| | 48 mg Comp. (I), EtOH:H$_2$O (1 mL) | Pattern A | Pattern A | Pattern G | Pattern A | Pattern A |

TABLE 4-continued

Summary of XRPD analysis of slurry and slow evaporation experiments. "A" represents at 45° C. and "B" represents at 15° C.

| Sample ID | Temperature | Solvent | XRPD from Slurry | XRPD Slow evaporation |
|---|---|---|---|---|
| 15A | 45° C. | EtOH:H2O | Pattern A | Pattern A |
| 15B | 15° C. | (95:5) | Pattern A | Pattern A |

*Clear solution was obtained

Slow evaporation of samples 2A, 2B, and the slurry of Compound (I) in MeOH (sample 2B) at 15° C. resulted in a new XRPD pattern (Pattern B) which is illustrated in FIG. 8.

The Slurry of Compound (I) in DCM (sample 6B) at 15° C. resulted in a new XRPD pattern (Pattern C) which is illustrated in FIG. 9.

III. Polymorph Screening of Compound (I)

Fast cooling crystallization experiments of Compound (I) in five different solvents were performed to screen for new polymorphs.

A known amount of Compound (I) (see Table 3) was dissolved in 1 mL of the solvent at 50° C. and immediately placed in an ice bath (at least for 2 h). Later the sample vials were placed in the refrigerator (with lids on). After two days the samples were found to yield crystals which were then analyzed by XRPD. Table 5 summarizes the experimental details and the results of XRPD analysis on the crystalline material obtained.

The XRPD analysis of the anti-solvent samples revealed the presence of a new crystalline form of Compound (I) (Form VII, Pattern G, FIG. 11).

Figure 12:
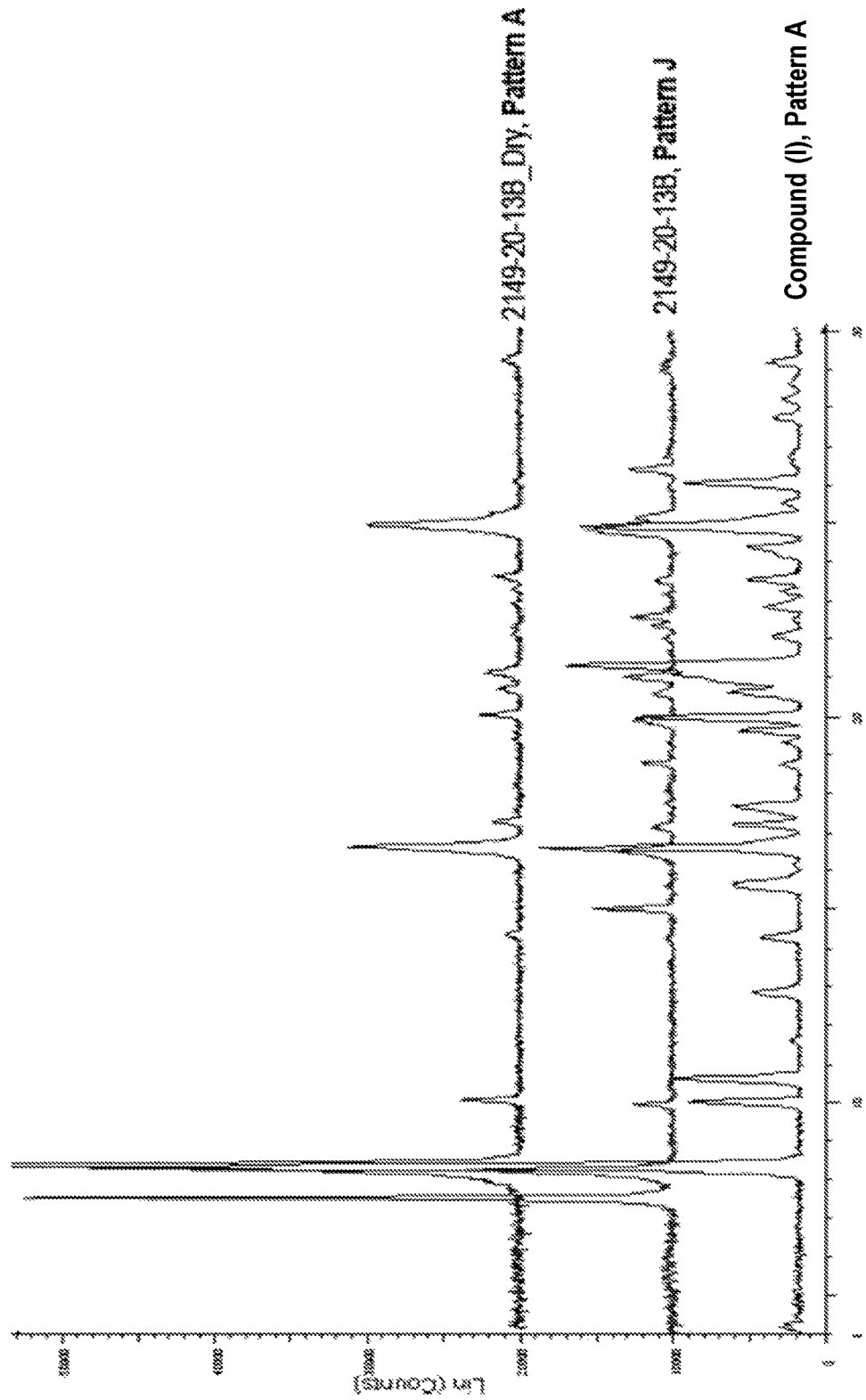
FIG. 12 shows a comparison of XRPD patterns of wet and dry samples of Pattern J with Form I (Pattern A).
Figure 13:
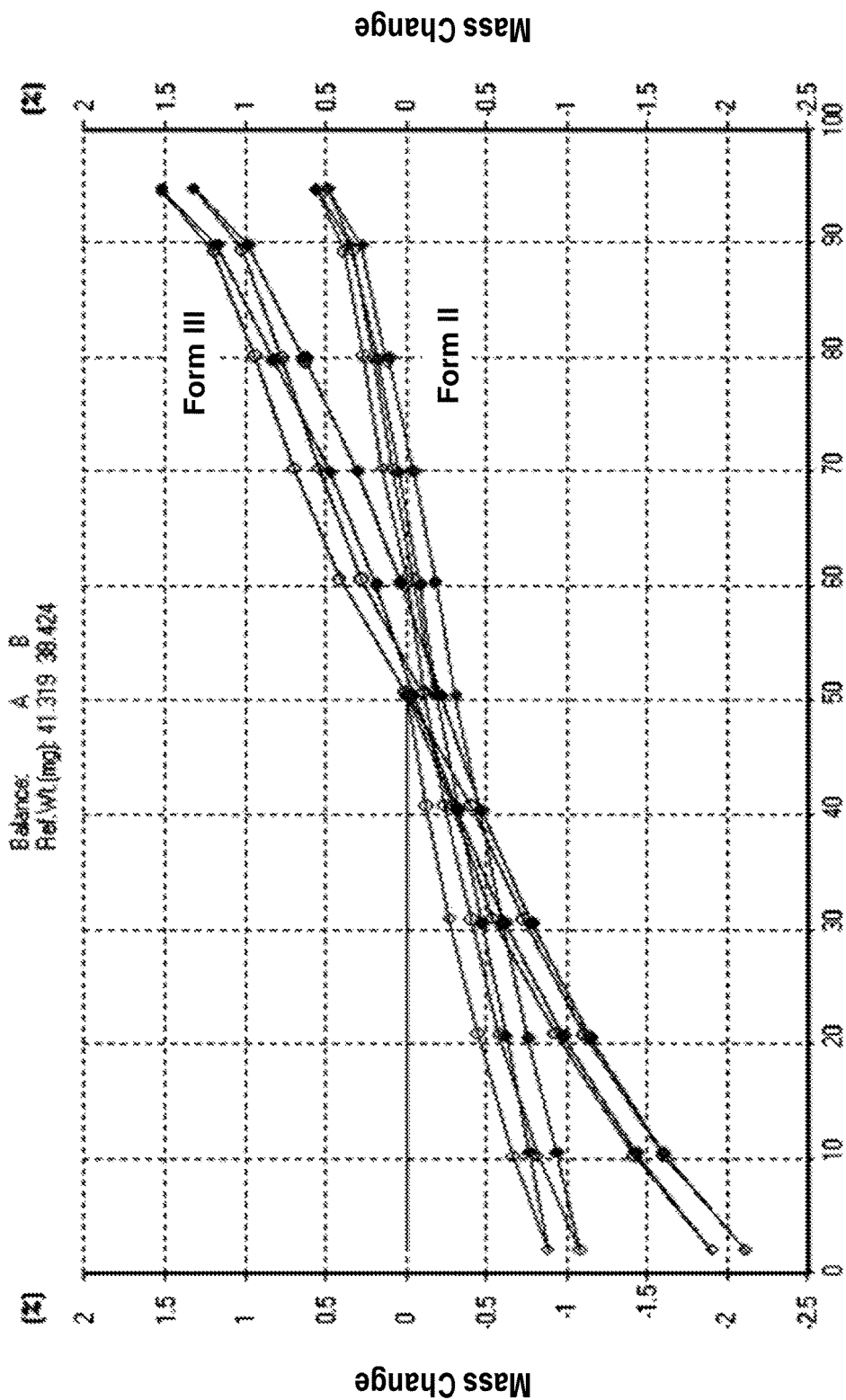
FIG. 13 shows the DVS-Isotherm of Form II and Form III.

To a gel obtained by the slow evaporation of Compound (I) in dimethylacetamide (DMA), 1.5 mL of DCM was added and after 30 min a white solid precipitated out from the solution. This sample was analyzed by XRPD and a new crystalline form, characterized by Pattern J, of Compound (I) was obtained. However, after drying the sample at 45° C. under vacuum, Pattern J transformed to Pattern A (See, e.g., FIG. 12). Attempts to reproduce Pattern J were not successful. Additionally, reanalyzing the sample after three days by XRPD, it was revealed that Pattern J transformed to Pattern A at room temperature.

III. Vapor Diffusion Experiments of Compound (I)

Vapor diffusion experiments of Compound (I): In this experiment, around 30 mg of Compound (I) was dissolved completely in 1.5 mL solvent in a small vial which was later placed in a larger vial with another solvent (1 mL) with the lid closed. The vials were left undisturbed until crystals were observed. Table 7 presents the solvents used for diffusion experiments.

TABLE 7

Diffusion Experiments of Compound (I)

| Sample No. | Solvent used for dissolving Compound (I) | Solent used in the bigger vial (for vapor diffusion) | XRPD |
|---|---|---|---|
| 7 | EtOH | EtOAc | Pattern A |
| 8 | Acetone | EtOAc | Pattern A |
| 9 | IPA | EtOAc | Pattern A |
| 10 | THF | EtOAc | Pattern A |
| 11 | Acetone:H$_2$O (95:5) | EtOAc | Pattern A |
| 12 | EtOH:H$_2$O (95:5) | EtOAc | Pattern A |

IV. Neat and Solvent Drop Grinding of Compound (I)

Neat and solvent drop grinding (THF, water, MeOH, EtOH, acetone, DCM and MeCN) experiments were also performed as a part of polymorph screening. All the experiments resulted in XRPDs that were identical with Pattern A.

Example 4

Scale-up and Characterization of Crystalline Forms of Compound (I), Form II (Pattern B) and Form III (Pattern C)

I. Scale-up of Patterns B and C

Form II (Pattern B) and Form III (Pattern C) were successfully scaled up and characterized by XRPD, optical microscopy, DVS, $^1$H-NMR, DSC, TGA, DVS and KF.

Dynamic vapor sorption (DVS) on samples of Form II and Form III was performed and it was found that the sample of Form II exhibited a weight change <1% while the sample of Form III exhibited a weight change of around 1.5% when exposed to high humidity conditions.

The post-DVS samples of the MeOH (Pattern B) and DCM (Pattern C) solvates of Compound (I) were analyzed by XRPD. It was found that both Patterns B and C underwent a form change after the end of the experiments to a new pattern, Pattern D (i.e., Form IV).

II. Form II is a Methanol (MeOH) Solvate of Compound (I)

Figure 14:
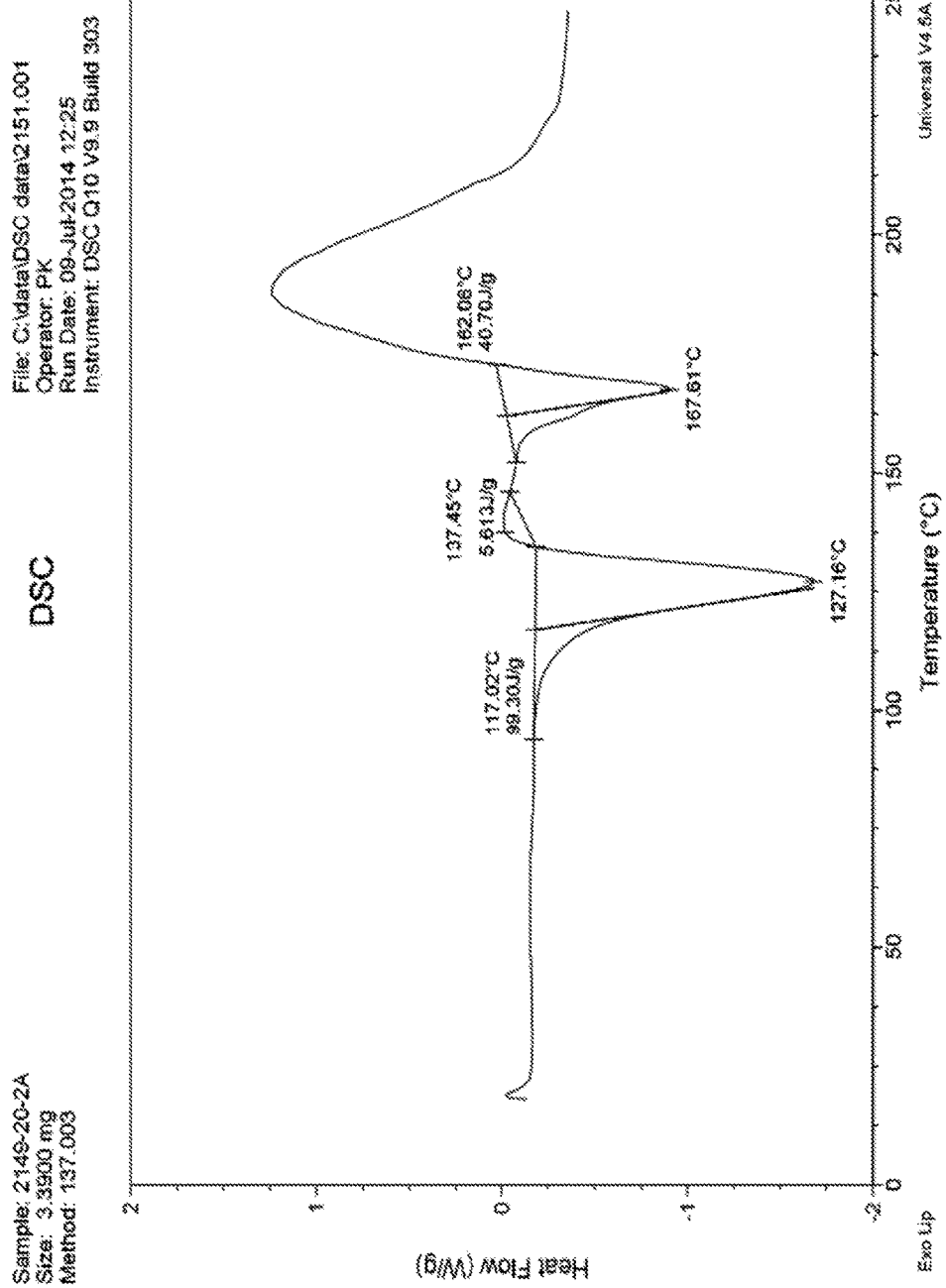
FIG. 14 shows the DSC thermogram of Form II (Pattern B).
Figure 15:
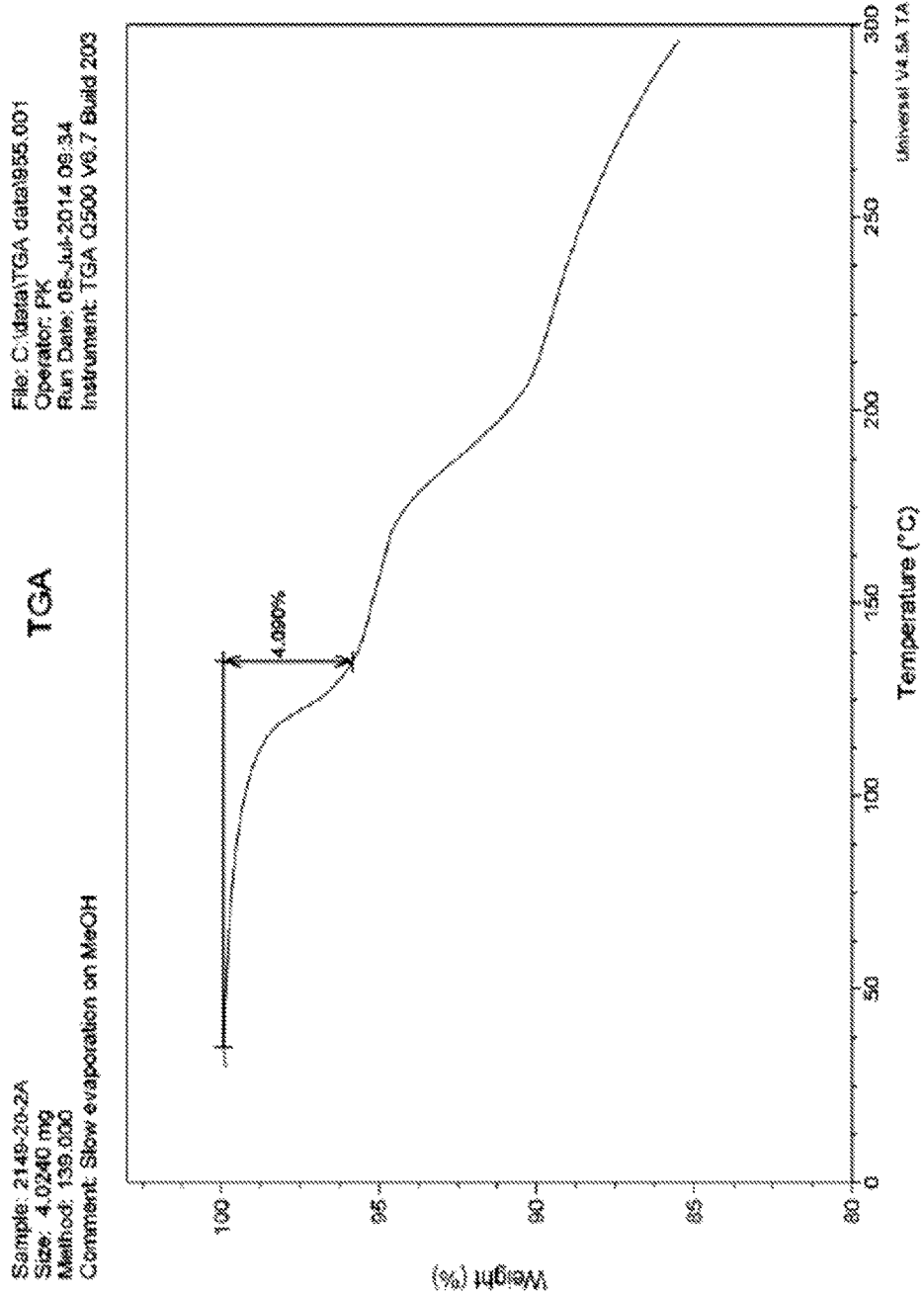
FIG. 15 shows the TGA of Form II (Pattern B).

The DSC of Form II, Pattern B (FIG. 14) revealed the presence of two endothermic events; one at around 127° C. followed by another at around 168° C. The sample was further analyzed by TGA (FIG. 15) and the results revealed a weight loss of around 4% from 35 to 135° C. The $^1$H-NMR analysis (FIG. 16) of the material revealed the presence of MeOH. The molar ratio of MeOH to Compound (I) was found to be 0.5:1 (hemi MeOH solvate of Compound (I)).

III. Form III is a Dichloromethane (DCM) Solvate

Figure 17:
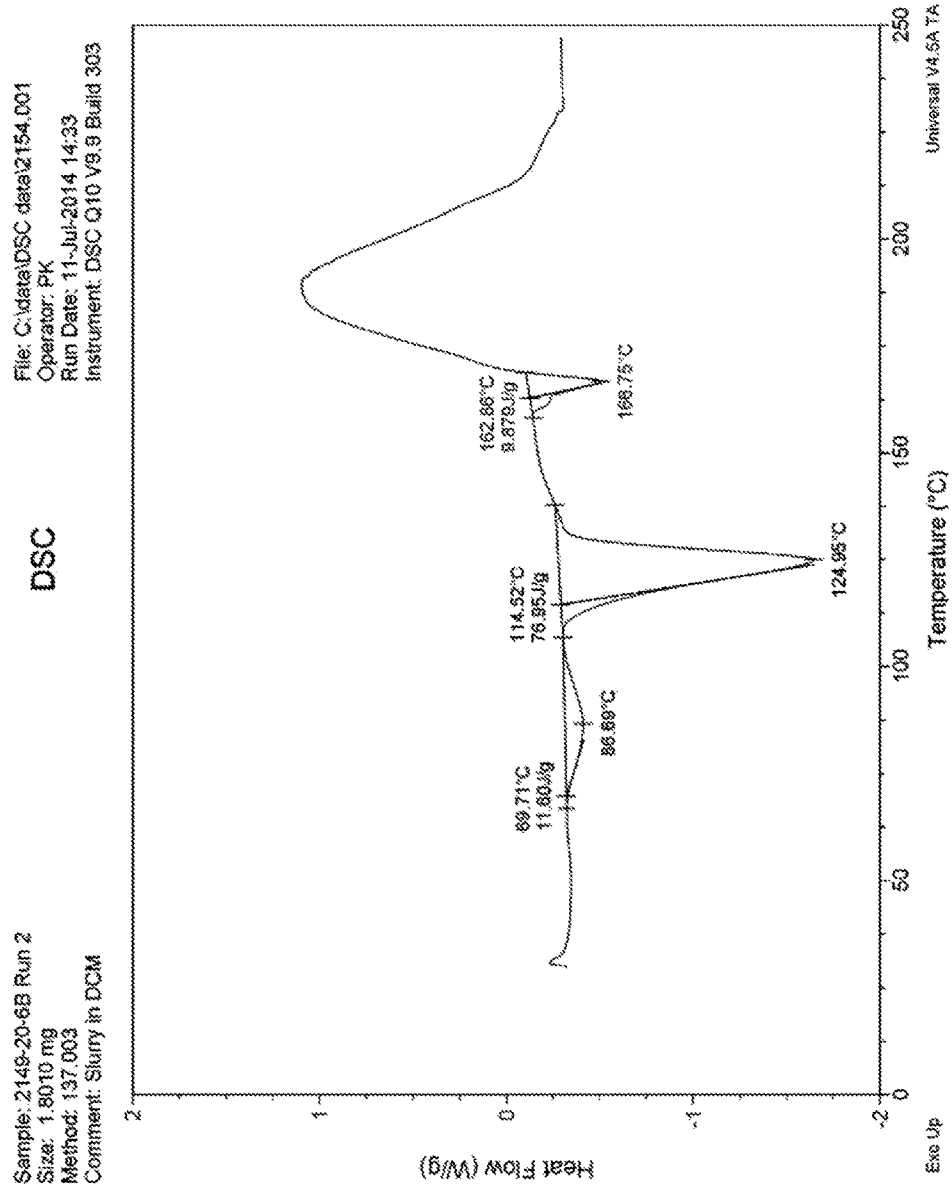
FIG. 17 shows the DSC thermogram of Form III (Pattern C).
Figure 18:
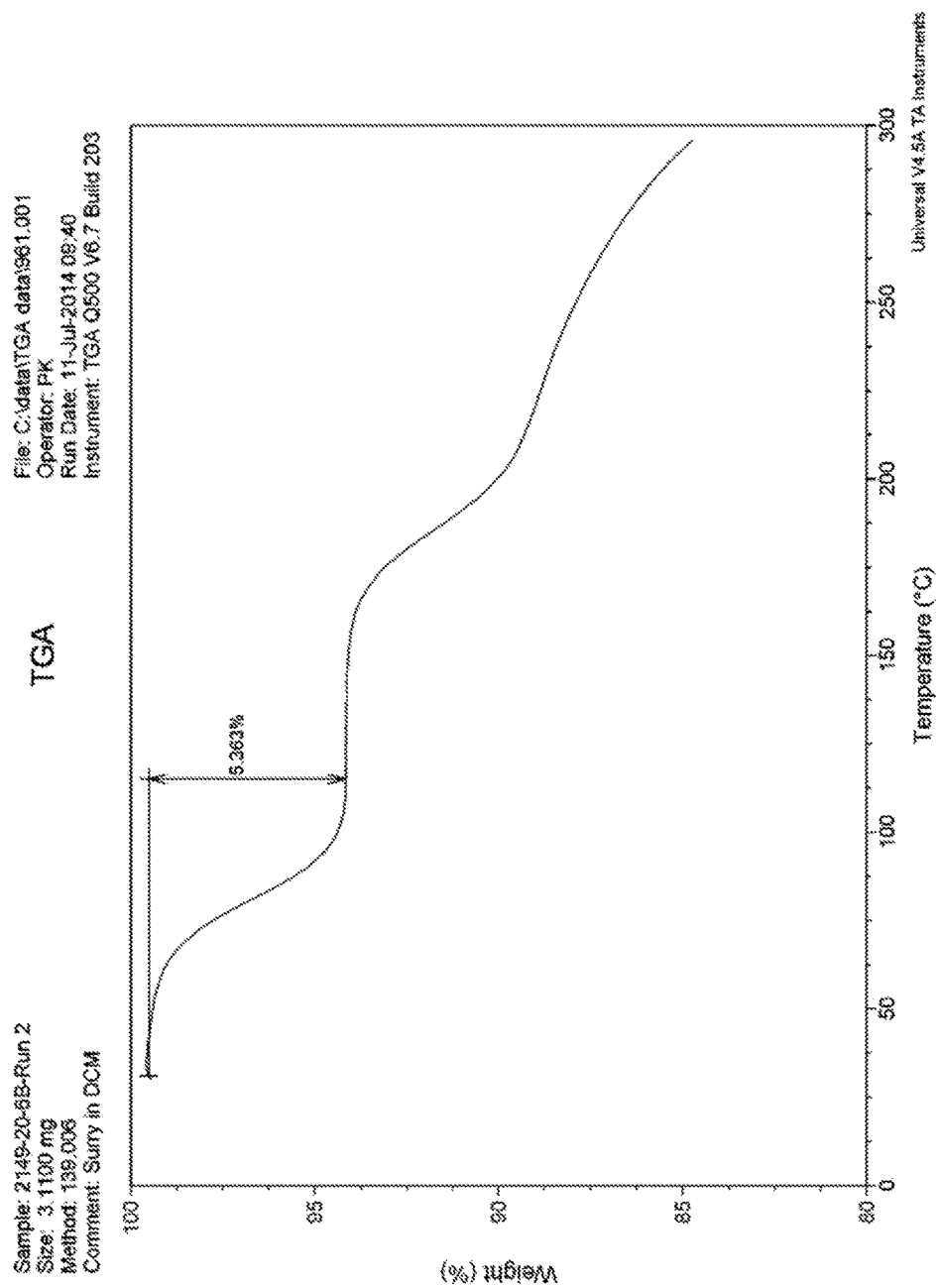
FIG. 18 shows the TGA of Form III (Pattern C).
Figure 19:
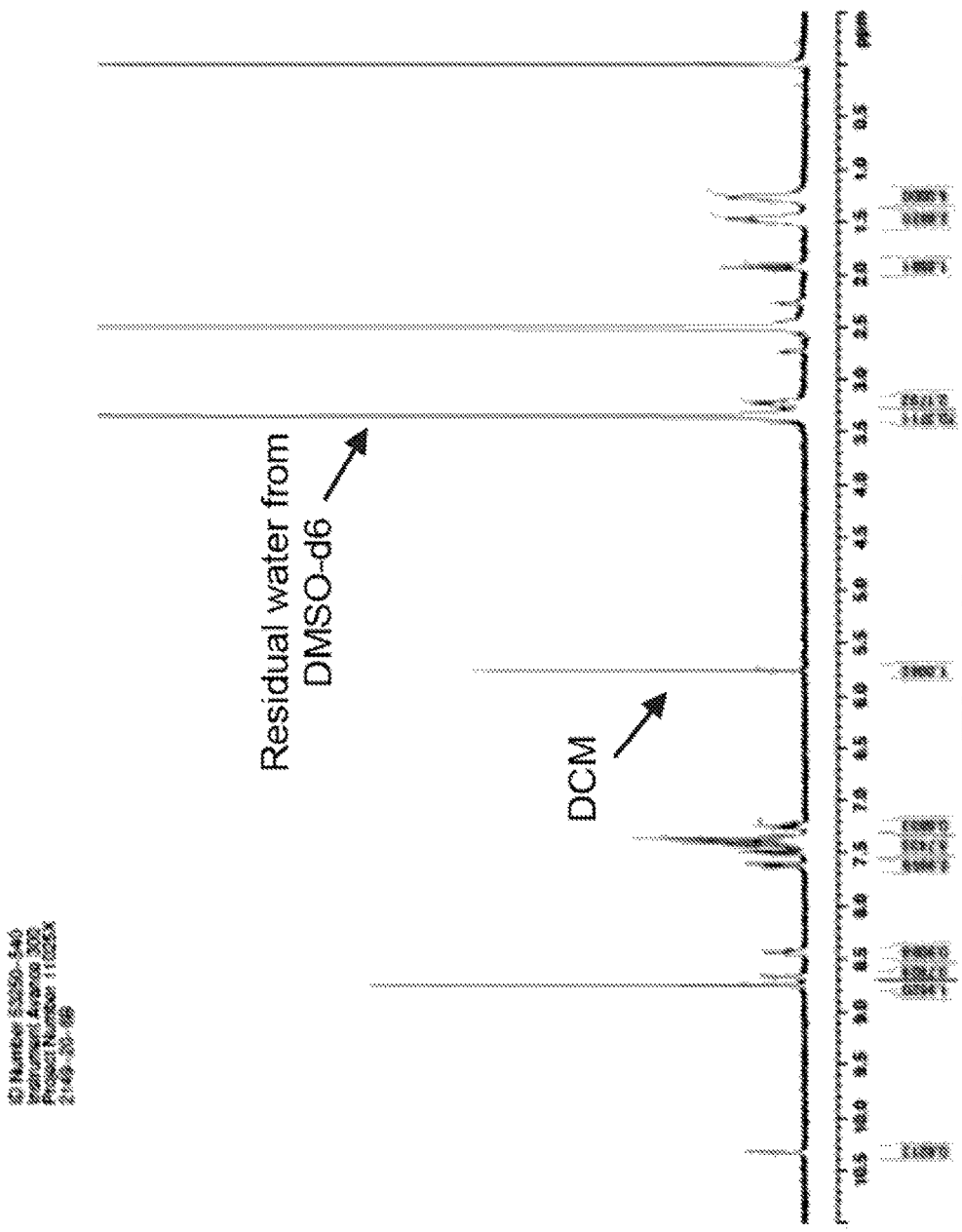
FIG. 19 shows the $^1$H-NMR data of Form III (Pattern C).

The DSC of Form III, Pattern C (FIG. 17) revealed the presence of three endothermic events; one at around 86° C., 125° C. followed by another at around 167° C. The sample was further analyzed by TGA (FIG. 18) and the results revealed a weight loss of around 5% from 35 to 115° C. The $^1$H-NMR analysis (FIG. 19) of the material revealed the presence of DCM. The molar ratio of DCM to Compound (I) was found to be 0.5:1 (hemi DCM solvate of Compound (I)).

Stability of the Compound (I) Solvates

The MeOH and DCM solvates of Compound (I) were tested for stability under dry and humid conditions.

For dry conditions, the sample was dried under vacuum at 45° C. followed by XRPD analysis. Later the sample was subjected to high humidity conditions (RH >95%) followed by XRPD analysis.

The MeOH and DCM solvates of Compound (I) were dried on XRPD plates under vacuum at 45° C. and were analyzed by XRPD the following day.

It was found that both the solvates underwent a form change upon drying which was evident by the XRPD analysis of the dried samples (FIGS. 20 and 21). Both the solvates of Compound (I) upon drying resulted in a new but same XRPD pattern called Pattern D, Form IV. The XRPD plates were later exposed to high humidity conditions (RH >95%) overnight followed by XRPD analysis the following day. No further change in the crystalline form was observed.

The desolvation of MeOH and DCM from Compound (I) solvates was confirmed by $^1$H-NMR.

Example 5

Figure 22:
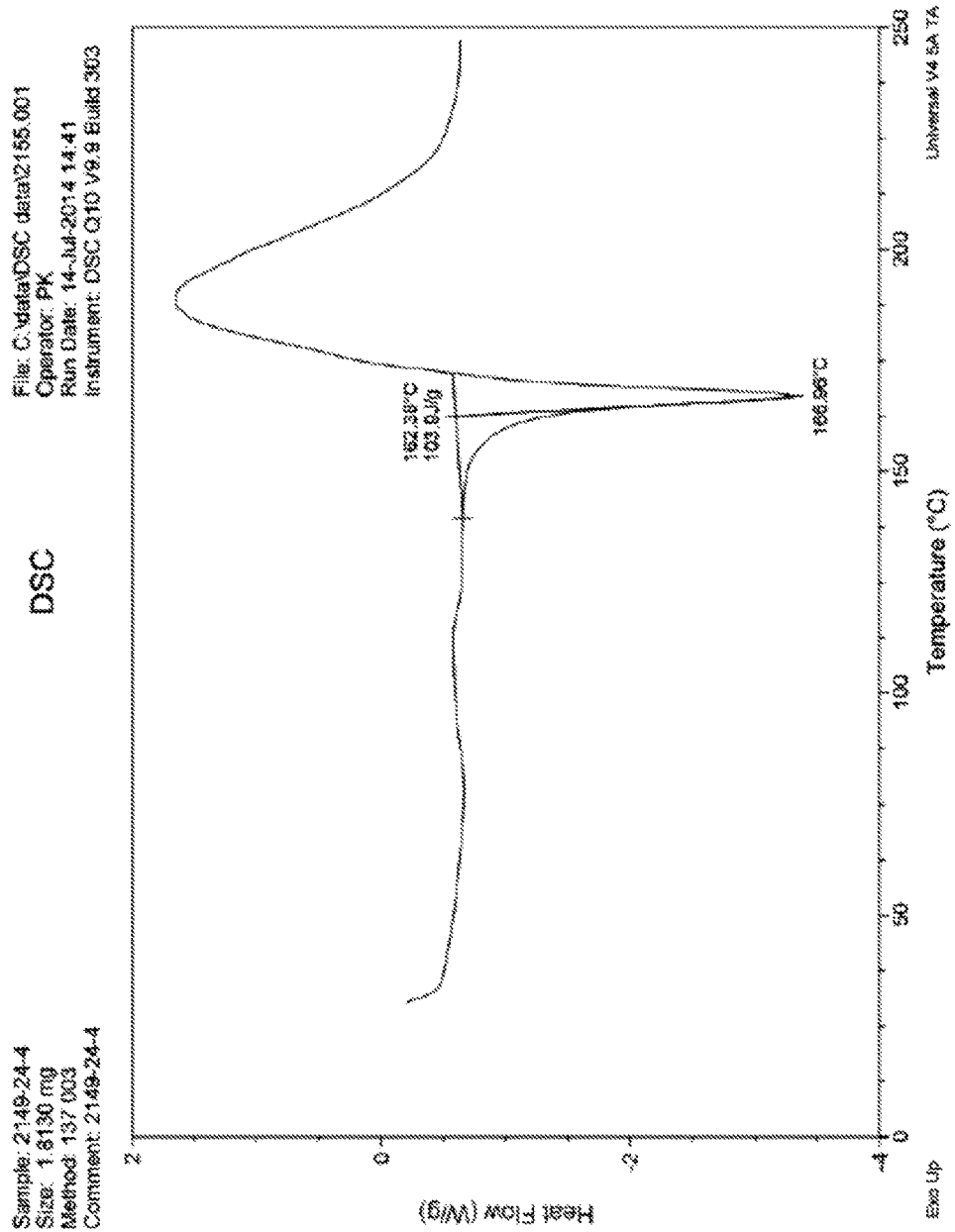
FIG. 22 shows the DSC thermogram of Form V (Pattern E).
Figure 23:
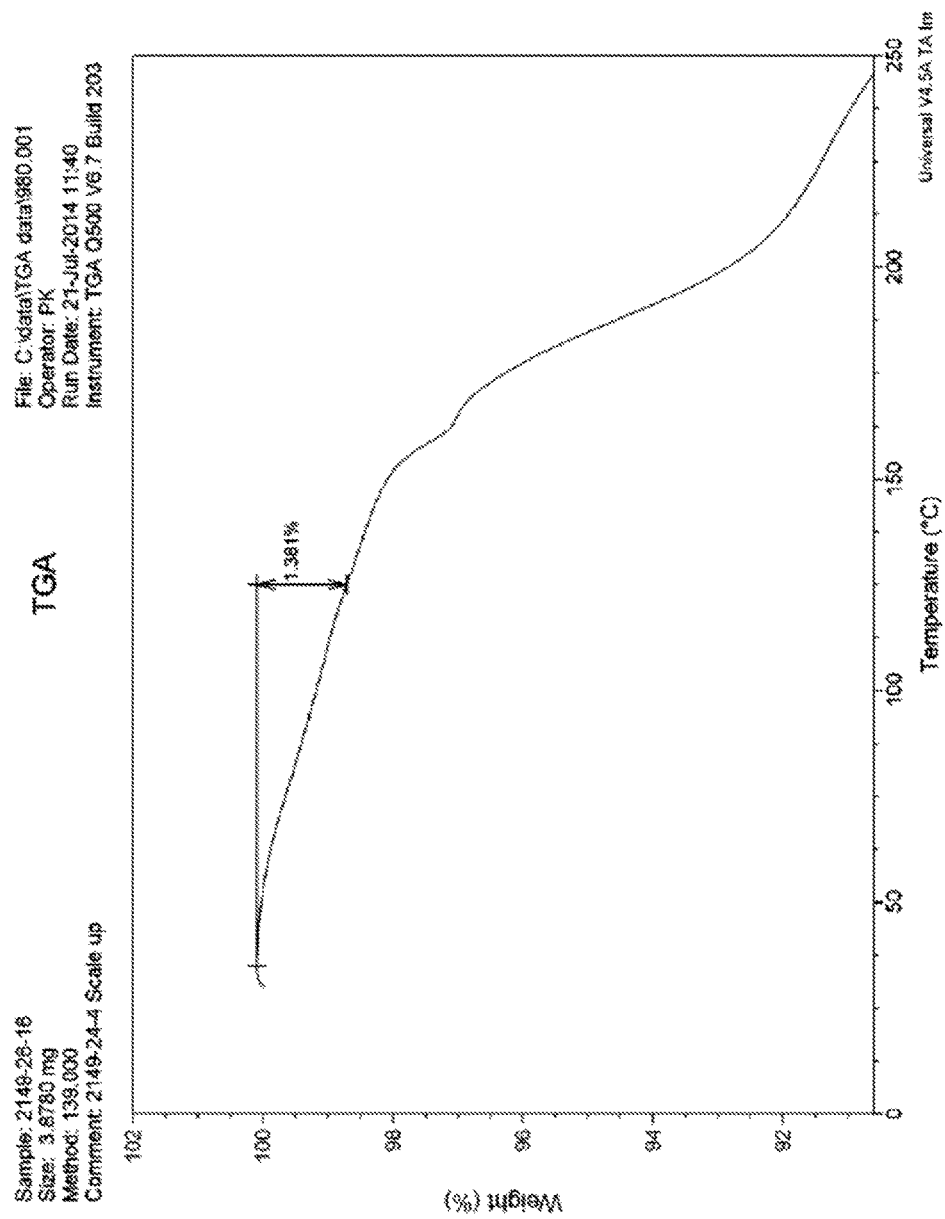
FIG. 23 shows the TGA of Form V (Pattern E).
Figure 24:
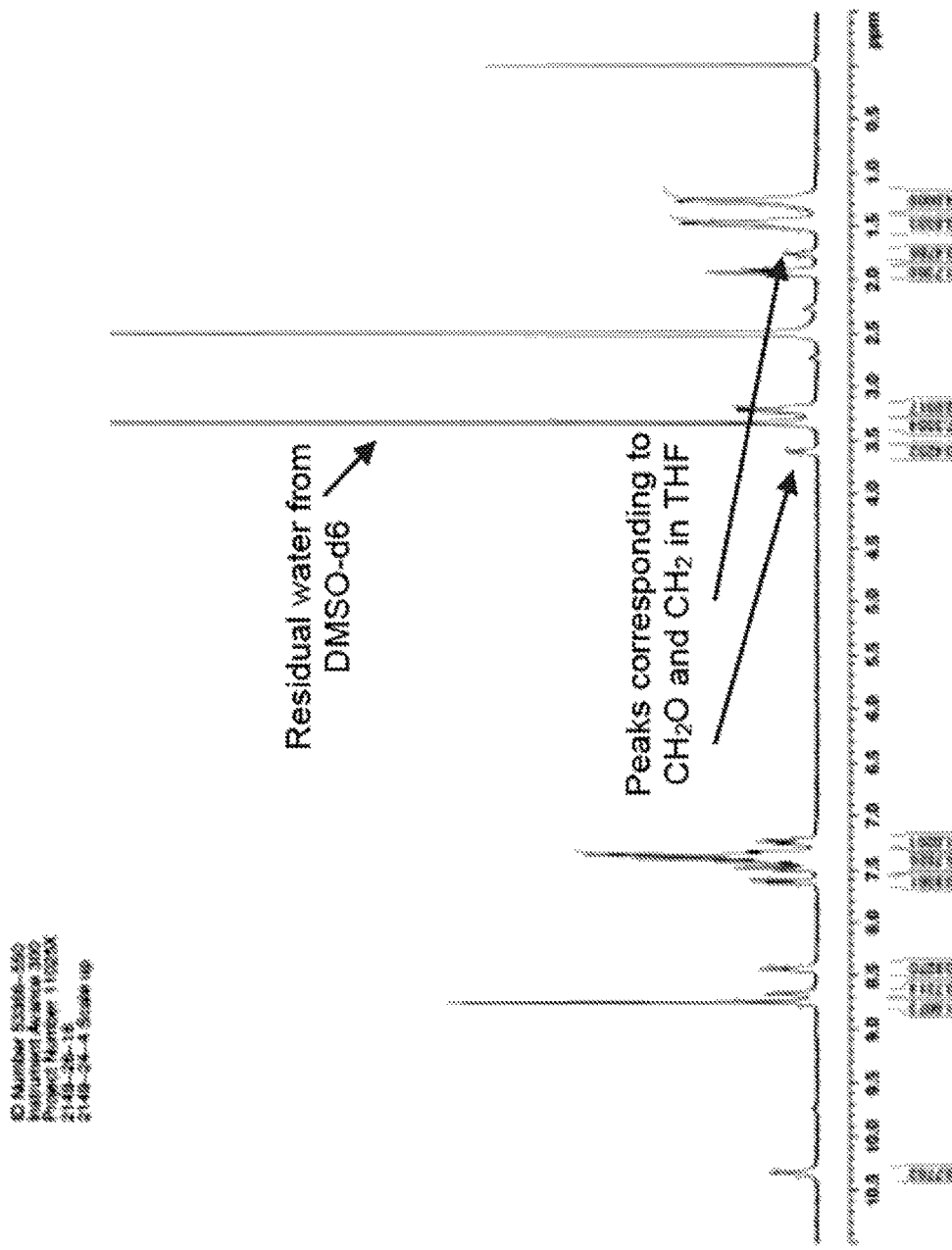
FIG. 24 shows $^1$H-NMR data of Form V (Pattern E)

Scale-up and Characterization of Crystalline Forms of Compound (I), (Form V) Pattern E Pattern E (Form V) was successfully scaled up and characterized by XRPD, optical microscopy, DVS, $^1$H-NMR (FIG. 24), DSC (FIG. 22), TGA (FIG. 23), DVS (FIG. 25) and Karl-Fisher. The molar ratio of THF to Compound (I) was found to be 0.3:1. KF titration revealed the presence of around 0.9% water content in it.

Pattern E was dried at 45° C. under vacuum overnight and analyzed by XRPD. The following day, it was subjected to high humidity conditions (>95%) and later analyzed by XRPD the next day. It was found that drying Form V, Pattern E under vacuum at 45° C. results in a form change which was confirmed by XRPD (Form VI, Pattern F). However, after exposing the sample to high humidity conditions there was no further form change. FIG. 26 illustrates the XRPD comparison of dried and humid samples with Compound (I), Form I, Pattern A.

Figure 25:
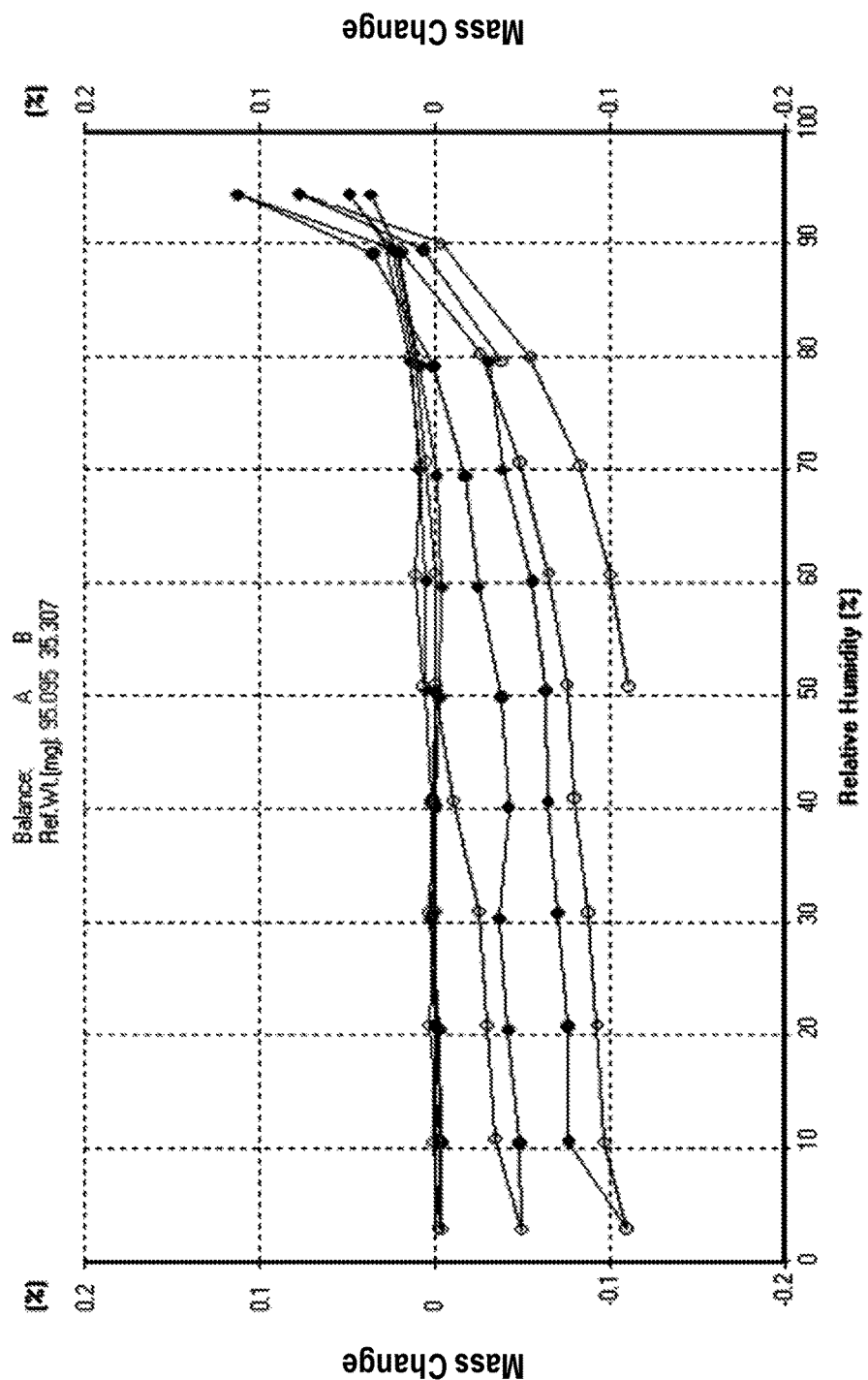
FIG. 25 shows the DVS-Isotherm of Form V, Pattern E.

Pattern E was subjected to a DVS experiment (FIG. 25). It was found that the sample had a moisture uptake of <0.15% when exposed to high humidity conditions. A post DVS sample of Form V, Pattern E revealed a change in the XRPD pattern to that of Pattern F, Form VI. FIG. 26 also illustrates the comparison of XRPDs of pre and post DVS samples.

Example 6

Scale-up and Characterization of Crystalline Forms of Compound (I), Form VII (Pattern G)

The crystalline material of Form VII, Pattern G from both the anti-solvent experiments (see Table 6) was analyzed by optical microscopy. It was found that the samples had two different crystal morphologies (needles and elongated rods).

Initially, 2 of 25 anti-solvent addition experiments of Compound (I) resulted in the isolation of Pattern G (Table 6 and FIG. 11). Attempts to reproduce Pattern G by the previous methods were partially successful.

Using THF/MeCN solvent mixtures, Pattern G was isolated successfully.

However, use of EtOH:H$_2$O (95:5)/MeCN resulted in the isolation of a new XRPD pattern (Pattern I).

Figure 27:
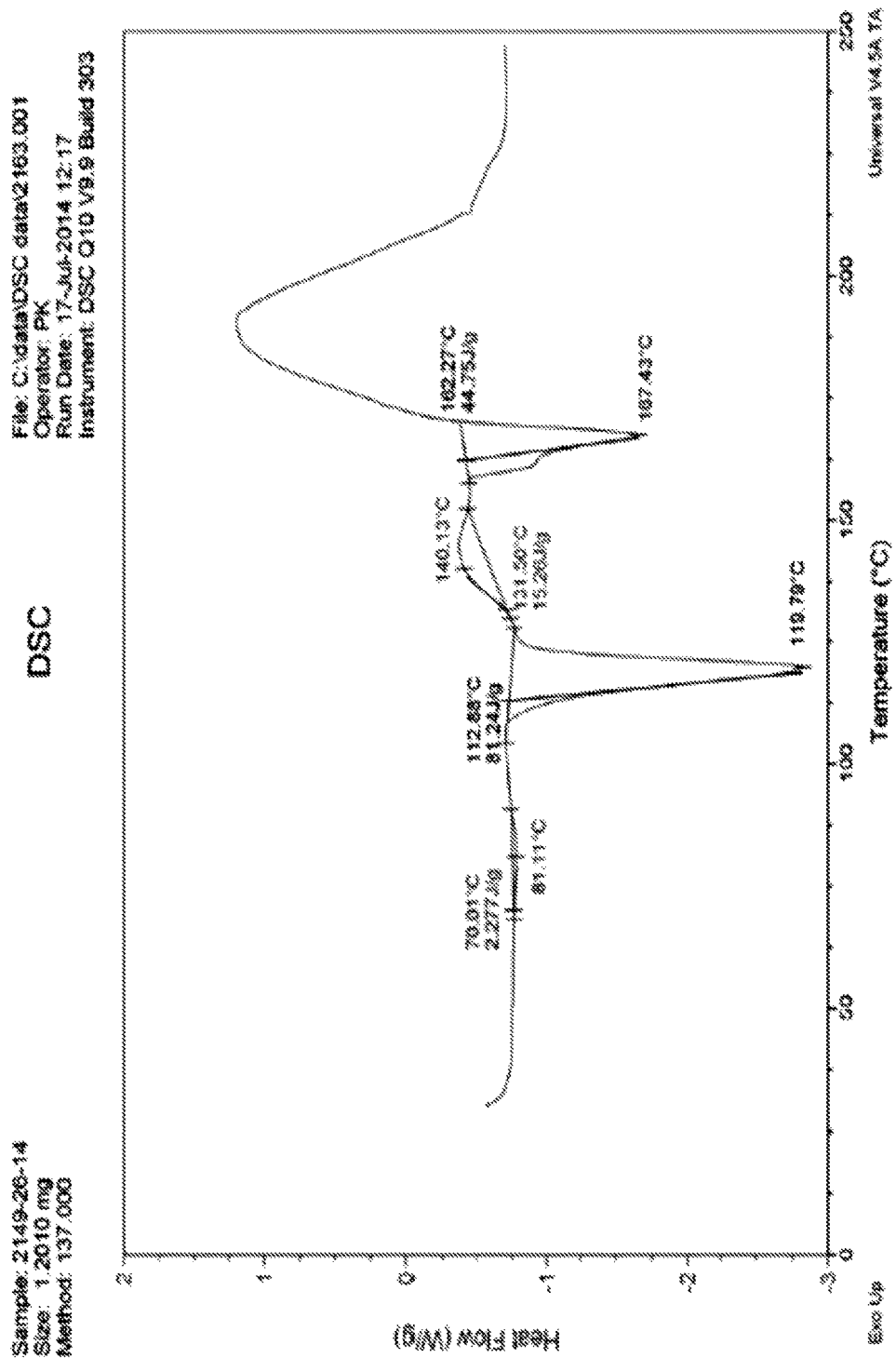
FIG. 27 shows the DSC thermogram of Form VII (Pattern G).
Figure 28:
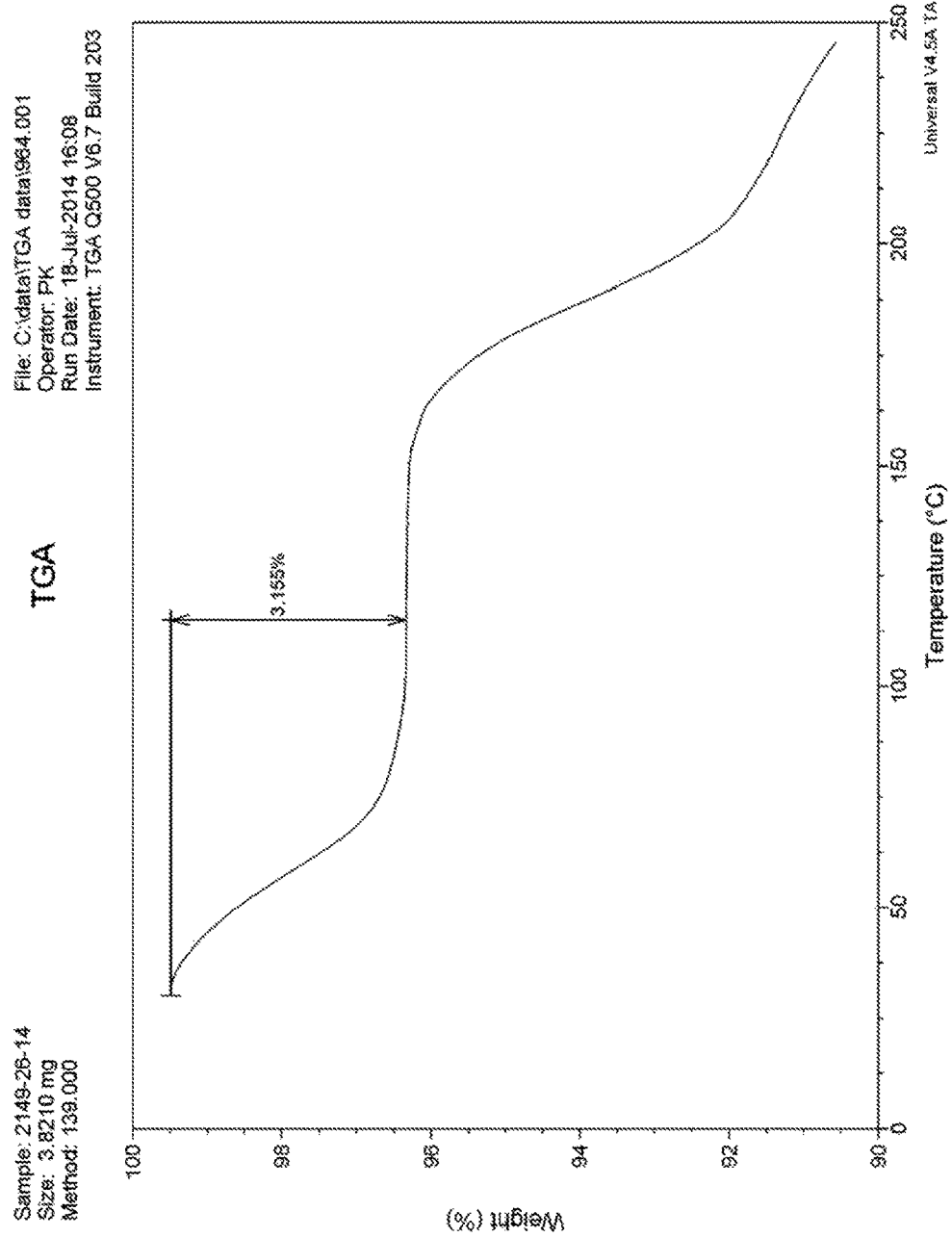
FIG. 28 shows the TGA of Form VII (Pattern G).

The Form VII, Pattern G sample was used for further characterization by DSC (FIG. 27), TGA (FIG. 28), and $^1$H NMR.

Figure 29:
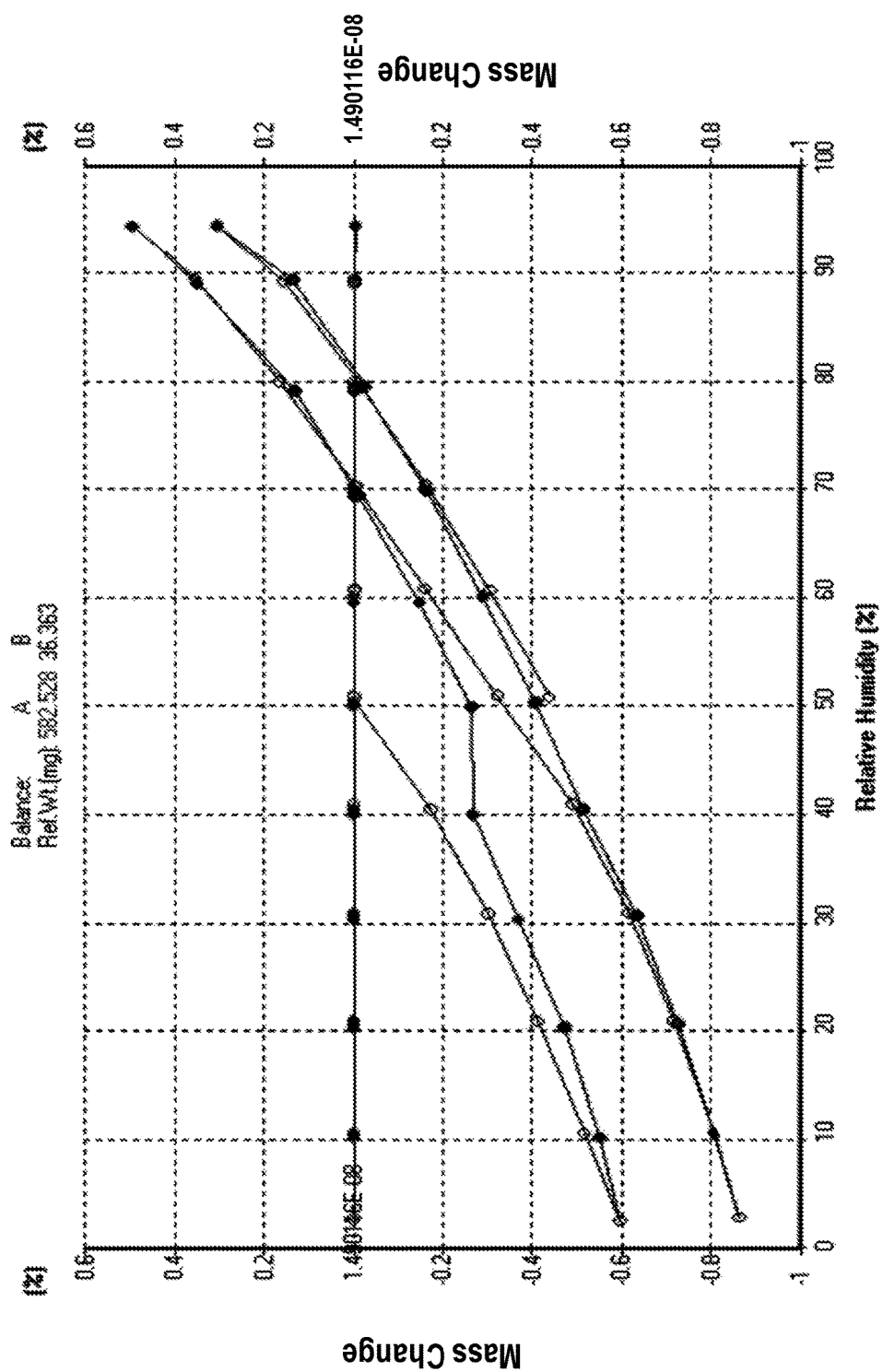
FIG. 29 shows the DVS-Isotherm of Form VII, Pattern G.

After the analysis of sample Form VII, Pattern G by XRPD, the sample was dried under vacuum at 45° C. Further analysis by XRPD confirmed a form change upon drying (Pattern H, see, e.g., FIG. 30). However, after exposing the sample to high humidity conditions there is no further form change. Pattern G was also characterized by DVS (FIG. 29).

The XRPD analysis on the post DVS sample revealed that it undergoes a form change from Pattern G to Pattern H. This is the form which was obtained when Pattern G was dried at 45° C. under vacuum. FIG. 30 illustrates the XRPD comparison of all the phase transformation in Pattern G.

Example 7

Scale-up and Characterization of Crystalline Forms of Compound (I), Form IX (Pattern I)

Figure 31:
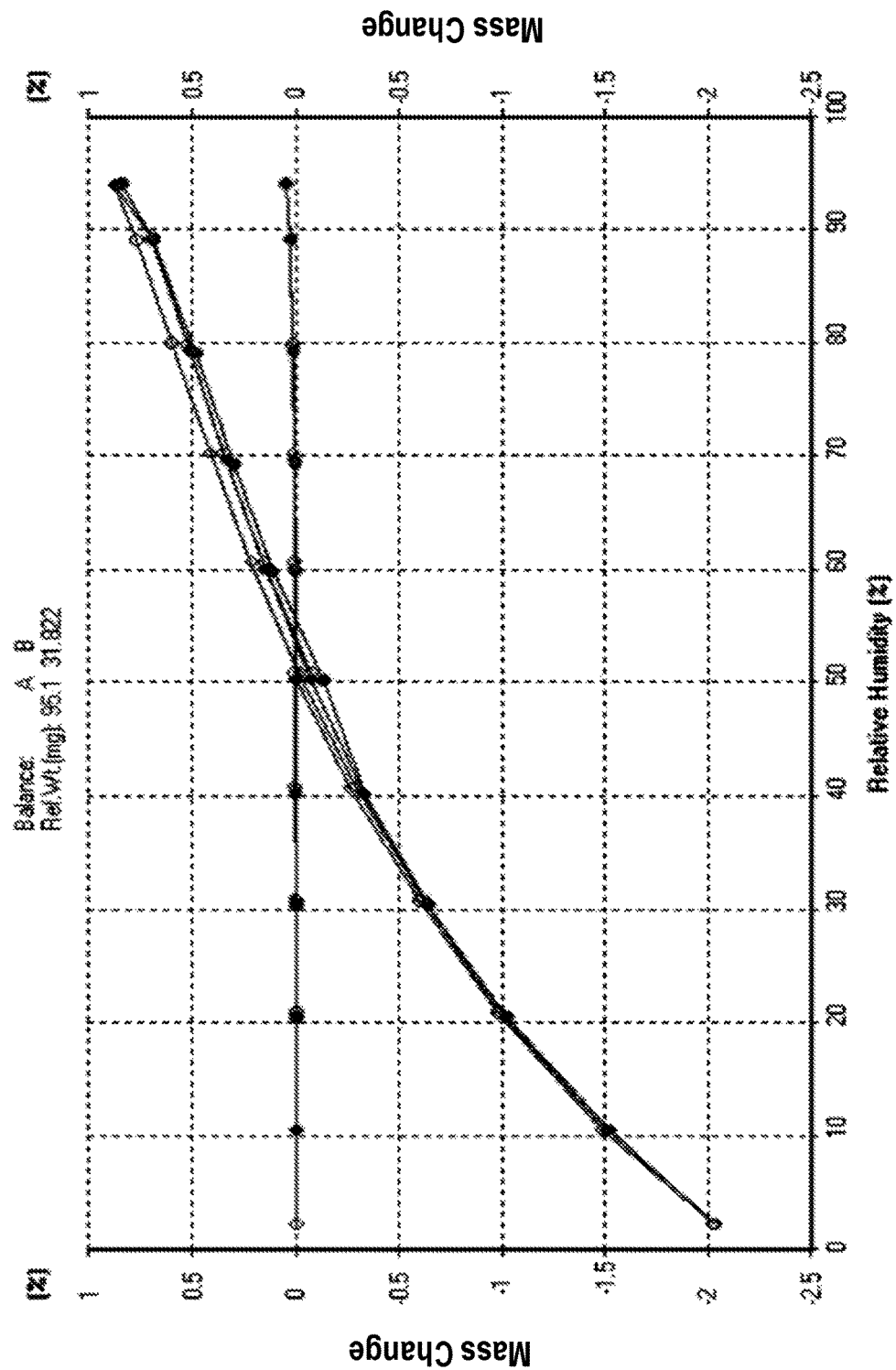
FIG. 31 shows a DVS-Isotherm of Form IX, Pattern I.

Anti-solvent addition experiment using EtOH:H$_2$O (95:5)/MeCN resulted in the isolation of a new XRPD pattern (Pattern I, Form IX). Pattern I or Form IX was characterized by optical microscopy, NMR, DVS (FIG. 31) and KF and thermal analysis was carried out by DSC and TGA.

Pattern I was characterized by XRPD, and the stability was also tested by drying the same sample under vacuum at 45° C. and followed by exposing the sample to high humidity conditions (FIG. 32).

Example 8

Characterization of Crystal Forms Obtained after Drying

I. Patterns B and C

Figure 33:
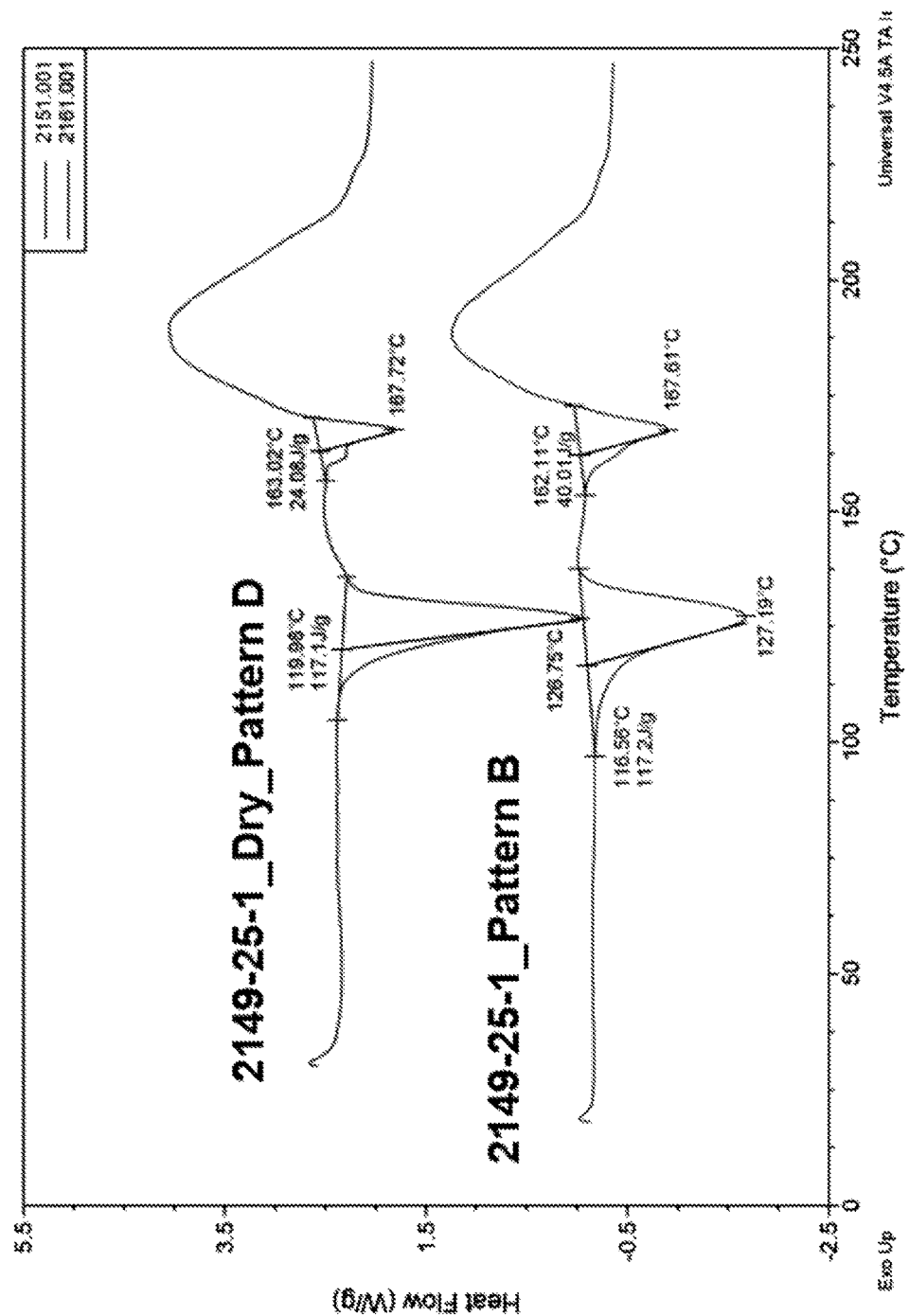
FIG. 33 shows DSC thermograms of Form II (Pattern B) before and after drying at 45° C.
Figure 34:
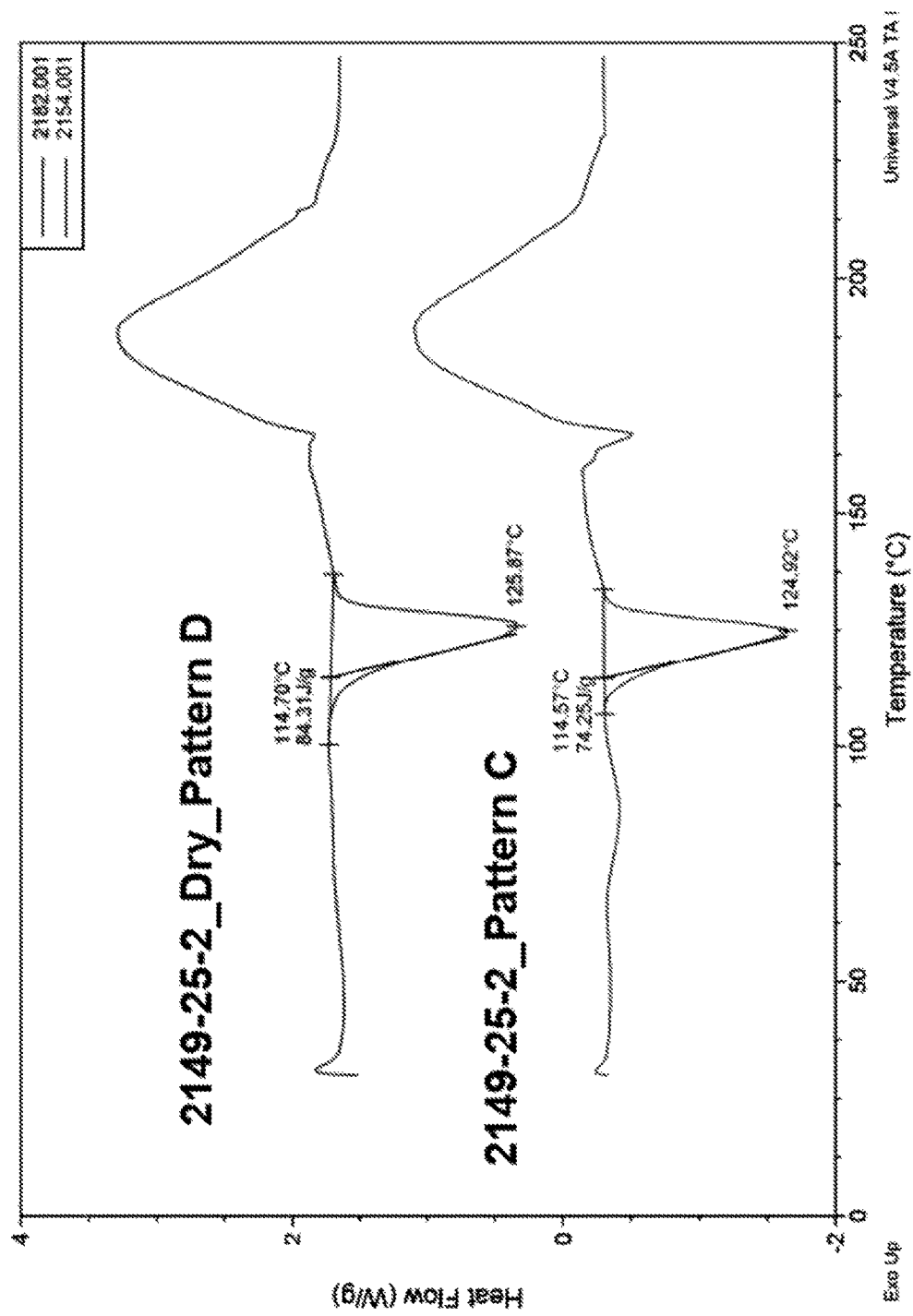
FIG. 34 shows DSC thermograms of Form III (Pattern E) before and after drying at 45° C.

Pattern B and Pattern C after drying at 45° C. under vacuum transforms to Pattern D. Patterns B (FIG. 33) and C (FIG. 34) exhibited two endotherms during the DSC analysis. Endotherm 1 corresponds to the melting point (127° C.: Pattern B, 125° C.: Pattern C) followed by recrystallization after 130° C. and transforming to Pattern A which melts at around 168° C.

Similarly, Pattern D (FIG. 33) also exhibited two endotherms. Endotherm 1 corresponds to the melting point (127° C.) followed by recrystallization after 130° C. and transforming to Pattern A which melts at around 168° C. However, the transformation of Pattern D to A was not observed in FIG. 34.

The TGA analysis of Pattern B revealed a weight loss of around 4.5% from 35 to 145° C. whereas, Pattern D exhibited a weight loss of around 1.1% from 35 to 145° C. The TGA analysis of Pattern C revealed a weight loss of around 5.4% from 35 to 145° C. whereas, Pattern D exhibited a weight loss of around 0.8% from 35 to 145° C.

After heating Form II (Pattern B) at 130° C. for 30 minutes the sample was analyzed by XRPD and it was found that Pattern B transforms to Pattern A.

II. Pattern E on Drying

Figure 35:
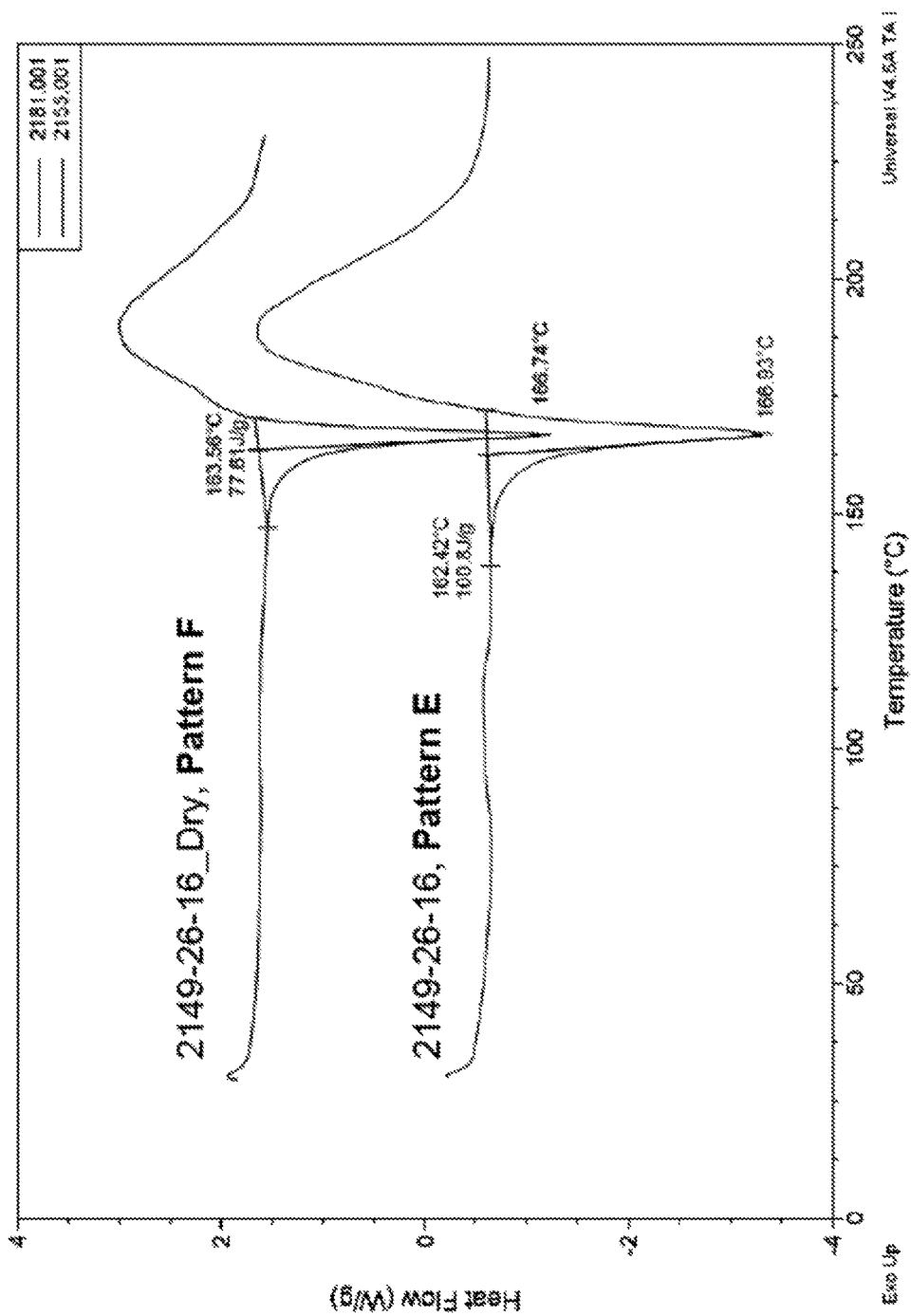
FIG. 35 shows DSC thermograms of Form V (Pattern E) before and after drying at 45° C.

Pattern E (Form V) upon drying resulted in the generation of Pattern F (Form VI). The DSC of Pattern E exhibits an endotherm at around 167° C. and the dried sample (Pattern F) exhibit a melting point close to Pattern E (FIG. 35).

The TGA analysis of Pattern E revealed a weight loss of around 5.4% from 35 to 145° C. whereas Pattern D exhibited a weight loss of around 0.8% from 35 to 145° C.

III. Pattern G on Drying

Figure 36:
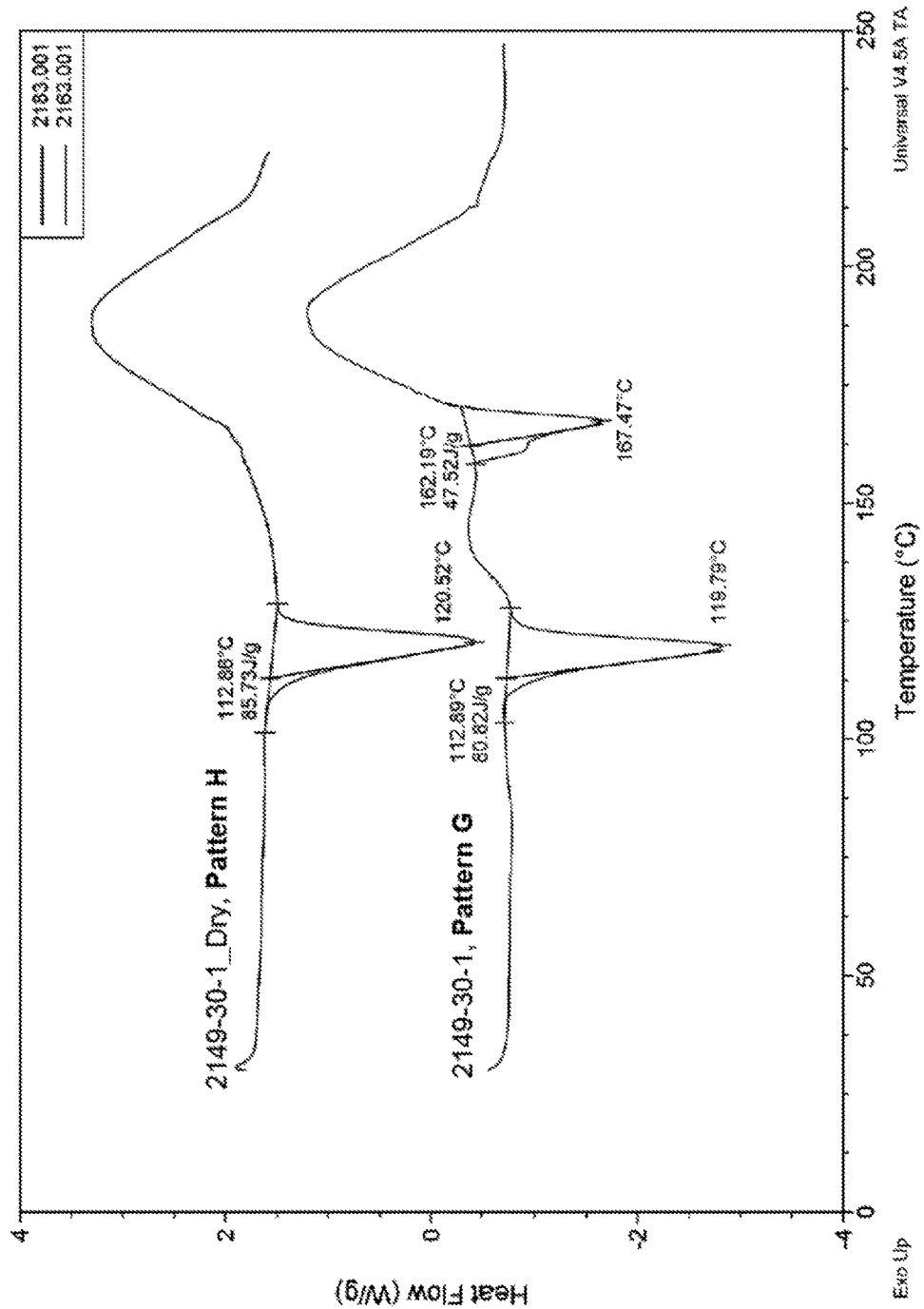
FIG. 36 shows DSC thermograms of VII (Pattern G) before and after drying at 45° C.

Pattern G upon drying resulted in the generation of Pattern H. Pattern G (FIG. 36) exhibited two endotherms and an exotherm at around 135° C. Endotherm 1 corresponds to the melting point (119° C.) followed by the recrystallization at 135° C. and transformation to Pattern A which melts at around 167° C. However, the dried sample revealed the presence of only one endotherm at around 120° C. corresponding to the melting of Pattern H.

The TGA of Pattern G exhibited a weight loss less than 0.3% and the dried sample exhibit a weight loss less than 0.1%.

IV. Pattern I on Drying

Figure 37:
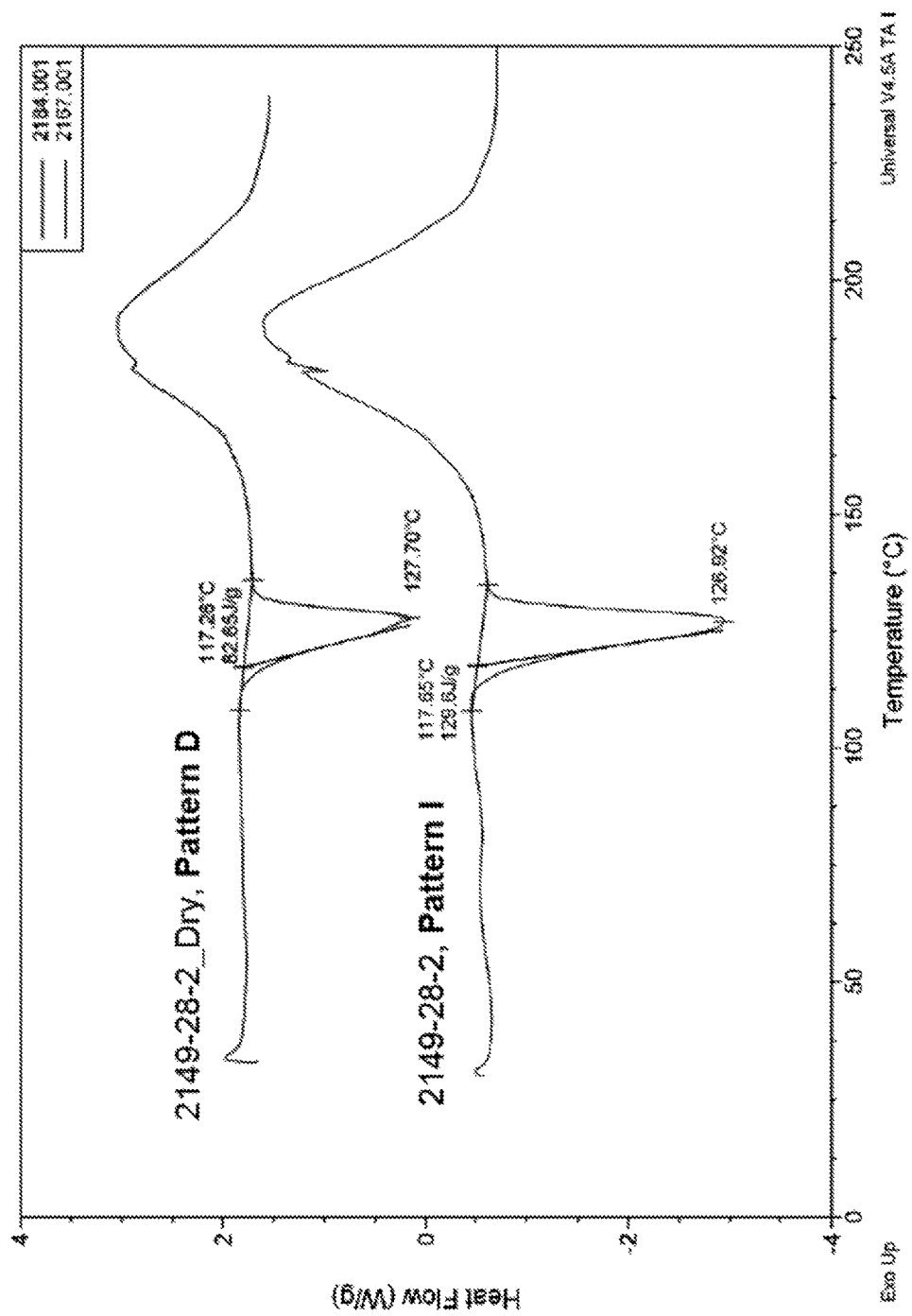
FIG. 37 shows DSC thermograms of Pattern I, Form IX before and after drying at 45° C.

Pattern I upon drying resulted in the generation of Pattern D. The DSC of Patterns I and D (FIG. 37) exhibited an endotherm at around 127-128° C. followed by possible decomposition.

A summary of the Drying Experiments is found in Table 8.

TABLE 8

Summary of the Drying Experiments

| | Before drying | | | After drying at 45° C. (under vacuum) | | |
|---|---|---|---|---|---|---|
| XRPD pattern | DSC | TGA (Wt loss %) | Post DVS XRPD | XRPD pattern | DSC | TGA (Wt loss %) |
| Pattern B | Endotherm at 127° C. Endotherm at 168° C. | 4.54% | Pattern D | Pattern D | Endotherm at 127° C. Endotherm at 168° C. | 1.07% |
| Pattern C | Endotherm at 125° C. Endotherm at 167° C. | 5.44% | Pattern D | Pattern D | Endotherm at 125° C. | 0.78% |
| Pattern E | Endotherm at 167° C. | 0.5% | Pattern F | Pattern F | Endotherm at 167° C. | 0.07% |
| Pattern G | Endotherm at 120° C. Endotherm at 167° C. | 0.27% | Pattern H | Pattern H | Endotherm at 121° C. | 0.05% |
| Pattern I* | Endotherm at 127° C. | 1.7% | Pattern D | Pattern D | Endotherm at 128° C. | 0.02% |

*not reproducible

Example 9

Relative Stability of the Forms

The crystalline forms of Compound (I) listed in Table 9 were used for the competitive slurries at 15 and 60° C. to determine the most stable form of Compound (I) in three different solvents (MeOH, EtOH and acetone:H$_2$O (95:5)).

For the competitive slurries, saturated solutions of Compound (I) in 0.5 mL of MeOH, EtOH and acetone: H₂O (95:5) were prepared (two sets for each solvent).

10 mg of Patterns A, B, C, D, E, F, G and H were added to each solution and stirred at 15 and 60° C. An aliquot from each slurries was drawn and analyzed by XRPD at t=0 min (approximately within a minute of stirring).

TABLE 9

Crystalline forms of Compound (I)

| XRPD Pattern assigned | Form of Compound (I) |
|---|---|
| Pattern A | Form I |
| Pattern B | Form II |
| Pattern C | Form III |
| Pattern D | Form IV |
| Pattern E | Form V |
| Pattern F | Form VI |
| Pattern G | Form VII |
| Pattern H | Form VIII |

Figure 38:
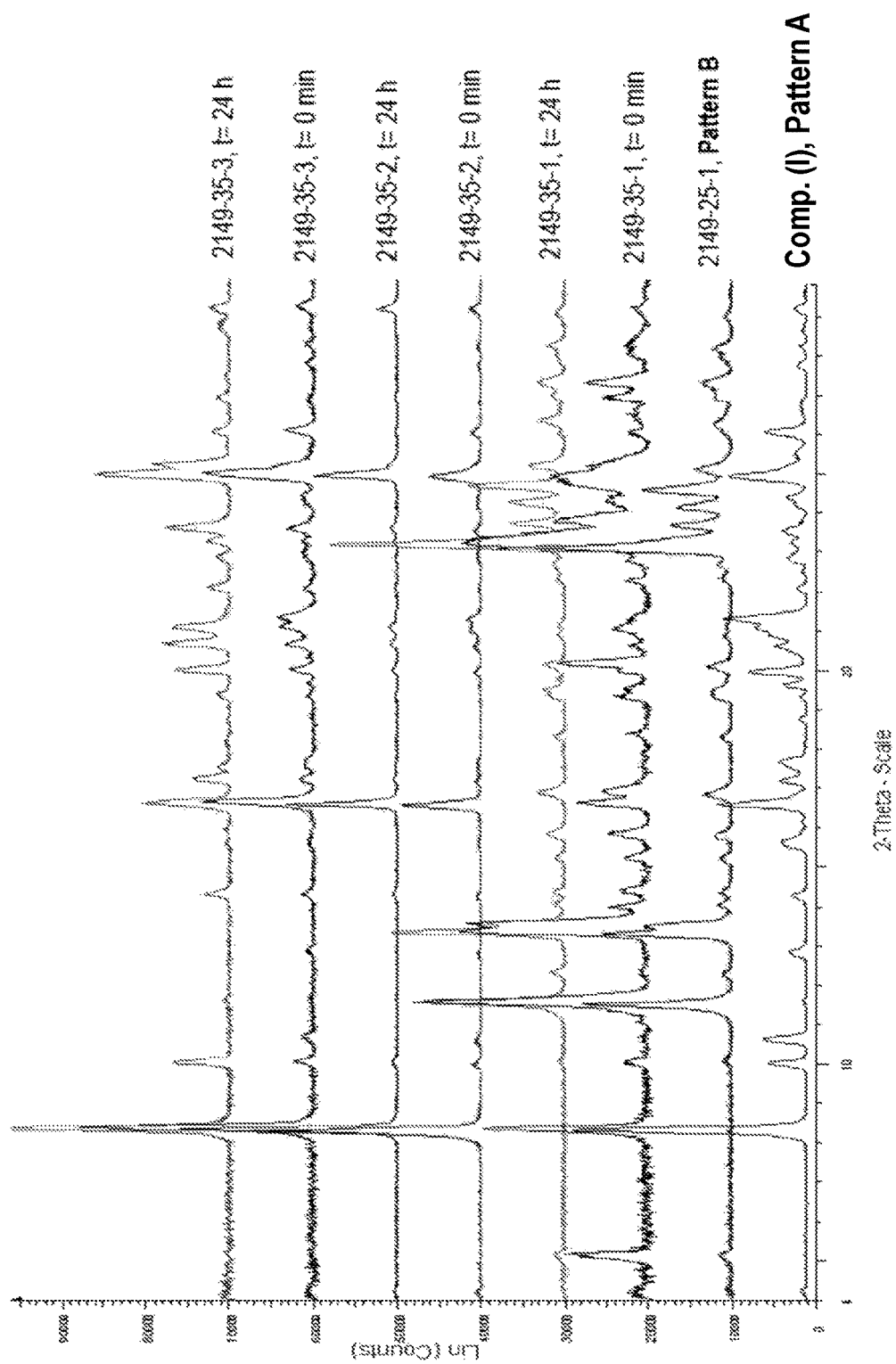
FIG. 38 shows a comparison of XRPD patterns of slurries in MeOH, EtOH and acetone:$H_2O$ (95:5) at 60° C.

FIG. 38 shows the XRPD comparison of samples from competitive slurries at 60° C. in MeOH, EtOH and acetone: H₂O (95:5) drawn at t=0 min and t=24 h.

It was found that the sample prepared in the MeOH slurry after t=0 min (after mixing for 30 seconds) revealed a mixed XRPD pattern of A and B. However, after 24 h slurry, a complete transformation to Pattern B was observed.

The sample prepared in the EtOH slurry and the sample prepared in the acetone:H2O (95:5) slurry transformed to Pattern A after stirring for less than a minute.

Figure 39:
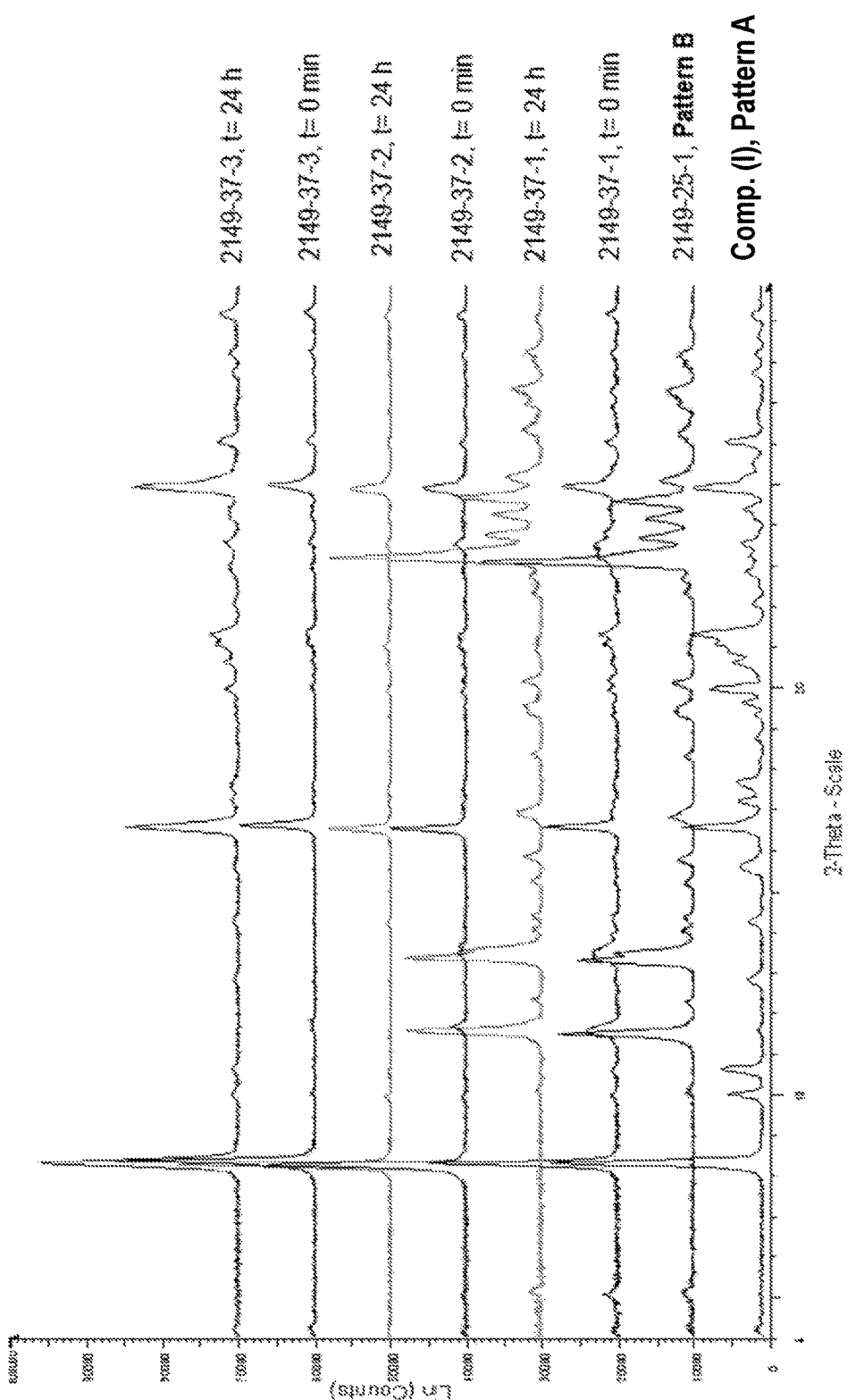
FIG. 39 shows a comparison of XRPD patterns of slurries in MeOH, EtOH and acetone:$H_2O$ (95:5) at 15° C.

Similarly, a XRPD comparison of samples from competitive slurries at 15° C. in MeOH, EtOH and acetone:H₂O (95:5) are illustrated in FIG. 39.

It was found that the samples prepared in the slurry in MeOH, after t=0 min (after mixing for 30 seconds) revealed a mixed XRPD patterns of A and B. However, after 24 h slurry, a complete transformation to Pattern B was observed.

Samples prepared in the slurry in EtOH and samples prepared in a slurry in acetone:H₂O (95:5)) transformed to Pattern A after stirring for less than a minute.

Example 10

Conclusions

The solid form screening experiments for Compound (I) resulted in the isolation of nine new crystalline forms, of which seven were reproducible.

Of the nine isolated forms, two were found to be hemisolvates of Compound (I) with MeOH and DCM.

The thermodynamically stable form of Compound (I) was determined to be Form I by slurry experiments in EtOH and acetone:H₂O (95:5) after 24 h at 15° C. and 60° C. However, in MeOH, Form II (MeOH solvate) was found to be the stable form after 24 h slurry at 15° C. and 60° C.

Example 11

XRPD Pattern A, Form I

XRPD analysis of a solid form of Compound (I) is shown in FIG. 40, the peak list for which is provided in Table 10. This Pattern is designated as "Pattern A" and corresponds to Form I of Compound (I).

TABLE 10

Peak list for Pattern A XRPD, Form I

| Angle (2Θ) degree | Intensity % | d value (Å) |
|---|---|---|
| 8.31 | 100 | 10.626 |
| 10.00 | 15.3 | 8.834 |
| 10.62 | 17.8 | 8.327 |
| 12.82 | 6.4 | 6.898 |
| 15.62 | 9.2 | 5.667 |
| 16.60 | 36.4 | 5.337 |
| 17.20 | 9.4 | 5.152 |
| 17.67 | 9.5 | 5.014 |
| 19.63 | 8.5 | 4.518 |
| 19.99 | 22.7 | 4.438 |
| 20.64 | 10.1 | 4.300 |
| 21.08 | 18.2 | 4.210 |
| 21.33 | 32.4 | 4.162 |
| 24.41 | 7.3 | 3.643 |
| 24.95 | 30.7 | 3.566 |
| 26.08 | 16.1 | 3.413 |

Example 12

XRPD Pattern B, Form II (Compound (I) MeOH Solvate)

XRPD analysis of another solid form of Compound (I) results in the pattern shown in FIG. 41, the peak list for which is provided in Table 11. This Pattern is designated as "Pattern B" and corresponds to Form II of Compound (I).

TABLE 11

Peak list for Pattern B XRPD, Form II

| Angle (2Θ) degree | Intensity % | d value (Å) |
|---|---|---|
| 5.07 | 37.5 | 17.387 |
| 11.58 | 90.9 | 7.632 |
| 13.96 | 18.5 | 6.336 |
| 14.37 | 17.4 | 6.156 |
| 15.86 | 20 | 5.580 |
| 16.93 | 21.9 | 5.230 |
| 19.33 | 13.7 | 4.586 |
| 19.53 | 15.5 | 4.539 |
| 20.16 | 39.7 | 4.400 |
| 22.28 | 13.8 | 3.985 |
| 23.33 | 69.1 | 3.809 |
| 23.80 | 52.6 | 3.734 |
| 24.78 | 31.1 | 3.589 |
| 25.31 | 12.4 | 3.514 |
| 26.94 | 21.4 | 3.301 |
| 27.35 | 37.6 | 3.257 |

Example 13

XRPD Pattern C, Form III (Compound (I) DCM Solvate)

XRPD analysis of another solid form of Compound (I) results in the pattern shown in FIG. 42, the peak list for which is provided in Table 12. This Pattern is designated as "Pattern C" and corresponds to Form III of Compound (I).

TABLE 12

Peak list for Pattern C XRPD, Form III

| Angle (2Θ) degree | Intensity % | d value (Å) |
|---|---|---|
| 5.07 | 40.2 | 17.410 |
| 8.31 | 9.2 | 10.638 |
| 11.69 | 100 | 7.563 |
| 13.52 | 76.7 | 6.545 |
| 13.69 | 66 | 6.462 |
| 14.45 | 8.9 | 6.125 |
| 15.91 | 12.7 | 5.567 |
| 17.05 | 13 | 5.197 |
| 20.26 | 19 | 4.379 |
| 21.10 | 9.7 | 4.208 |
| 23.57 | 64.2 | 3.772 |
| 23.99 | 27.4 | 3.706 |
| 24.58 | 10.1 | 3.618 |
| 25.04 | 19.6 | 3.554 |
| 26.89 | 16.5 | 3.313 |
| 27.3 | 10.8 | 3.264 |

Example 14

XRPD Pattern D, Form IV

XRPD analysis of another solid form of Compound (I) results in the pattern shown in FIG. 43, the peak list for which is provided in Table 13. This Pattern is designated as "Pattern D" and corresponds to Form IV of Compound (I).

TABLE 13

Peak list for Pattern D XRPD, Form IV

| Angle (2Θ) degree | Intensity % | d value (Å) |
|---|---|---|
| 5.13 | 32.9 | 17.212 |
| 11.78 | 100 | 7.508 |
| 13.60 | 61.8 | 6.506 |
| 13.80 | 77.2 | 6.412 |
| 14.48 | 10.4 | 6.112 |
| 16.01 | 15 | 5.532 |
| 17.13 | 19.9 | 5.172 |
| 20.30 | 26.7 | 4.370 |
| 21.16 | 10.6 | 4.195 |
| 23.69 | 82.4 | 3.753 |
| 24.05 | 42.7 | 3.698 |
| 24.70 | 13.3 | 3.601 |
| 25.16 | 25.1 | 3.536 |
| 26.95 | 19 | 3.306 |
| 27.36 | 14.3 | 3.258 |
| 30.61 | 9.1 | 2.918 |

Example 15

XRPD Pattern E, Form V

XRPD analysis of another solid form of Compound (I) results in the pattern shown in FIG. 44, the peak list for which is provided in Table 14. This Pattern is designated as "Pattern E" and corresponds to Form V of Compound (I).

TABLE 14

Peak list for Pattern E XRPD, Form V

| Angle (2Θ) degree | Intensity % | d value (Å) |
|---|---|---|
| 7.55 | 100 | 11.700 |
| 10.48 | 1.4 | 8.436 |
| 15.05 | 12.8 | 5.884 |

TABLE 14-continued

Peak list for Pattern E XRPD, Form V

| Angle (2Θ) degree | Intensity % | d value (Å) |
|---|---|---|
| 15.66 | 2.1 | 5.654 |
| 17.14 | 7.5 | 5.168 |
| 17.73 | 3.6 | 4.998 |
| 18.80 | 4.3 | 4.715 |
| 19.80 | 12.4 | 4.481 |
| 21.14 | 15.4 | 4.199 |
| 21.76 | 1.2 | 4.082 |
| 22.33 | 17.7 | 3.978 |
| 22.59 | 10.3 | 3.933 |
| 24.82 | 30 | 3.585 |
| 25.20 | 10.2 | 3.531 |
| 26.40 | 9.6 | 3.373 |
| 26.86 | 8.6 | 3.317 |

Example 16

XRPD Pattern F, Form VI

XRPD analysis of another solid form of Compound (I) results in the pattern shown in FIG. 45, the peak list for which is provided in Table 15. This Pattern is designated as "Pattern F" and corresponds to Form VI of Compound (I).

TABLE 15

Peak list for Pattern F XRPD, Form VI

| Angle (2Θ) degree | Intensity % | d value (Å) |
|---|---|---|
| 8.24 | 100 | 10.725 |
| 10.00 | 17.1 | 8.836 |
| 14.26 | 2.9 | 6.204 |
| 15.86 | 1.8 | 5.585 |
| 16.59 | 9.9 | 5.339 |
| 17.14 | 14.2 | 5.169 |
| 19.48 | 9.3 | 4.554 |
| 19.96 | 19.1 | 4.446 |
| 20.70 | 5.2 | 4.287 |
| 21.16 | 15.2 | 4.195 |
| 22.22 | 19 | 3.998 |
| 23.14 | 2.7 | 3.841 |
| 24.91 | 35.4 | 3.572 |
| 26.74 | 9.5 | 3.331 |
| 28.79 | 3.8 | 3.099 |

Example 17

XRPD Pattern G, Form VII

XRPD analysis of another solid form of Compound (I) results in the pattern shown in FIG. 46, the peak list for which is provided in Table 16. This Pattern is designated as "Pattern G" and corresponds to Form VII of Compound (I).

TABLE 16

Peak list for Pattern G XRPD, Form VII

| Angle (2Θ) degree | Intensity % | d value (Å) |
|---|---|---|
| 8.15 | 100 | 10.846 |
| 8.52 | 21.6 | 10.369 |

TABLE 16-continued

Peak list for Pattern G XRPD, Form VII

| Angle (2Θ) degree | Intensity % | d value (Å) |
|---|---|---|
| 10.21 | 5.2 | 8.656 |
| 14.11 | 12.5 | 6.274 |
| 16.29 | 45.7 | 5.438 |
| 18.66 | 5 | 4.751 |
| 19.47 | 10 | 4.555 |
| 21.58 | 18.4 | 4.115 |
| 22.72 | 9.3 | 3.911 |
| 24.50 | 9.1 | 3.631 |
| 24.86 | 8.6 | 3.578 |
| 25.80 | 11.8 | 3.451 |
| 26.82 | 9.7 | 3.322 |
| 29.55 | 9.7 | 3.021 |

Example 18

XRPD Pattern H, Form VIII

XRPD analysis of another solid form of Compound (I) results in the pattern shown in FIG. 47, the peak list for which is provided in Table 17. This Pattern is designated as "Pattern H" and corresponds to Form VIII of Compound (I).

TABLE 17

Peak list for Pattern H XRPD, Form VIII

| Angle (2Θ) degree | Intensity % | d value (Å) |
|---|---|---|
| 8.73 | 97.1 | 10.118 |
| 9.43 | 19.9 | 9.369 |
| 10.39 | 33.1 | 8.510 |
| 11.52 | 27.6 | 7.677 |
| 15.66 | 44.2 | 5.656 |
| 16.07 | 25.3 | 5.510 |
| 17.36 | 62.2 | 5.104 |
| 18.92 | 67 | 4.686 |
| 19.23 | 18.7 | 4.612 |
| 19.87 | 77.5 | 4.464 |
| 20.67 | 19.5 | 4.293 |
| 23.67 | 34.8 | 3.755 |
| 26.07 | 95.4 | 3.415 |
| 27.06 | 31.2 | 3.293 |
| 28.53 | 20.8 | 3.126 |
| 31.41 | 34.6 | 2.846 |

Example 19

XRPD Pattern I, Form IX

XRPD analysis of another solid form of Compound (I) results in the pattern shown in FIG. 48, the peak list for which is provided in Table 18. This Pattern is designated as "Pattern I" and corresponds to Form IX of Compound (I).

TABLE 18

Peak list for Pattern I XRPD, Form IX

| Angle (2Θ) degree | Intensity % | d value (Å) |
|---|---|---|
| 5.02 | 74.5 | 17.597 |
| 10.01 | 29.6 | 8.831 |
| 10.71 | 91.6 | 8.257 |
| 11.61 | 18.5 | 7.617 |
| 12.75 | 100 | 6.937 |
| 14.12 | 10.5 | 6.269 |
| 15.24 | 10.7 | 5.810 |
| 16.29 | 15.8 | 5.436 |
| 16.63 | 13.1 | 5.327 |
| 20.06 | 20.4 | 4.423 |
| 21.63 | 65.9 | 4.105 |
| 22.85 | 14.9 | 3.888 |
| 23.37 | 72.3 | 3.804 |
| 26.87 | 18.6 | 3.316 |
| 27.09 | 17.4 | 3.288 |
| 27.73 | 10.2 | 3.215 |

The invention claimed is:

1. A crystalline form of 2-((2-chlorophenyl)(phenyl)amino)-N-(7-(hydroxyamino)-7-oxoheptyl)pyrimidine-5-carboxamide, wherein the crystalline form is characterized by an X-ray powder diffraction pattern having peaks expressed in degrees-2-theta at angles 8.3±0.2°, 10.6±0.2°, 16.6±0.2°, 21.3±0.2°, and 25.0±0.2°.

2. The crystalline form of claim 1, wherein the crystalline form is characterized by a melting point at about 173° C.

3. The crystalline form of claim 1, wherein the crystalline form is characterized by a melting point at 173 ±2° C.

4. A pharmaceutical composition comprising a crystalline form of 2-((2-chlorophenyl)(phenyl)amino)-N-(7-(hydroxyamino)-7-oxoheptyl)pyrimidine-5-carboxamide, and a pharmaceutically acceptable carrier, wherein the crystalline form is characterized by an X-ray powder diffraction pattern having peaks expressed in degrees-2-theta at angles 8.3±0.2°, 10.6±0.2°, 16.6±0.2°, 21.3±0.2°, and 25.0±0.2°.

* * * * *